(12) United States Patent
Maj et al.

(10) Patent No.: US 9,050,319 B2
(45) Date of Patent: *Jun. 9, 2015

(54) PHOSPHOLIPID DRUG ANALOGS

(71) Applicant: Telormedix SA, Bioggio (CH)

(72) Inventors: Roberto Maj, Bioggio (CH); Franco Pattarino, Tornio (IT); Emanuela Mura, Bioggio (CH); Alcide Barberis, Bioggio (CH)

(73) Assignee: TELORMEDIX, SA, Bioggio (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/775,924

(22) Filed: Feb. 25, 2013

(65) Prior Publication Data

US 2013/0273144 A1 Oct. 17, 2013

Related U.S. Application Data

(63) Continuation-in-part of application No. 13/097,838, filed on Apr. 29, 2011.

(60) Provisional application No. 61/330,151, filed on Apr. 30, 2010, provisional application No. 61/708,513, filed on Oct. 1, 2012.

(51) Int. Cl.
| A61K 39/39 | (2006.01) |
| A61K 39/015 | (2006.01) |
| A61K 39/04 | (2006.01) |
| A61K 47/48 | (2006.01) |
| A61K 31/522 | (2006.01) |
| A61K 31/685 | (2006.01) |
| C07F 9/6561 | (2006.01) |
| A61K 39/00 | (2006.01) |

(52) U.S. Cl.
CPC ............... *A61K 39/39* (2013.01); *A61K 39/015* (2013.01); *A61K 39/04* (2013.01); *A61K 47/48053* (2013.01); *A61K 31/522* (2013.01); *A61K 31/685* (2013.01); *C07F 9/65616* (2013.01); *A61K 2039/55511* (2013.01)

(58) Field of Classification Search
CPC ..... A61K 39/39; A61K 39/015; A61K 39/04; A61K 47/48053; A61K 31/521; A61K 31/685; C07F 9/65616
USPC ...................... 424/450, 184.1, 283.1; 544/244
See application file for complete search history.

(56) References Cited

U.S. PATENT DOCUMENTS

| 5,084,269 | A | 1/1992 | Kullenberg |
| 5,624,677 | A | 4/1997 | El-Rashidy et al. |
| 5,785,975 | A * | 7/1998 | Parikh ........................ 424/278.1 |
| 6,329,381 | B1 | 12/2001 | Kurimoto et al. |
| 6,552,192 | B1 | 4/2003 | Hajduch et al. |
| 6,572,861 | B1 | 6/2003 | Roberts et al. |
| 6,716,840 | B2 | 4/2004 | Boyce et al. |

(Continued)

FOREIGN PATENT DOCUMENTS

| CN | 101230064 | 7/2008 |
| CN | 101239980 | 8/2008 |

(Continued)

OTHER PUBLICATIONS

Avanti Polar Lipids Catalog Product No. 850745, Oct. 18, 2006 http://web.archive.org/web/20061018193942/http://www.avantilipids.com/ProductInfo.asp?ProdNum=850745.*

Chan, M., (2009). Synthesis and immunological characterization of toll-like receptor 7 agonistic conjugates. Bioconjugate chemistry, 20(6), 1194-1200.*

Berman et al., "Expression of Fas-receptor on basal cell carcinomas after treatment with imiquimod 5% cream or vehicle" Br. J. Dermatol. (2003) 149 Suppl. 66:59-61.

(Continued)

*Primary Examiner* — Noble Jarrell
*Assistant Examiner* — John Mauro
(74) *Attorney, Agent, or Firm* — Grant IP, Inc.

(57) ABSTRACT

Provided in some embodiments are compositions comprising a compound having a structure according to Formula A or Formula B:

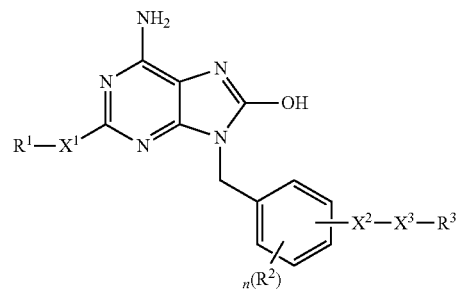

Formula A

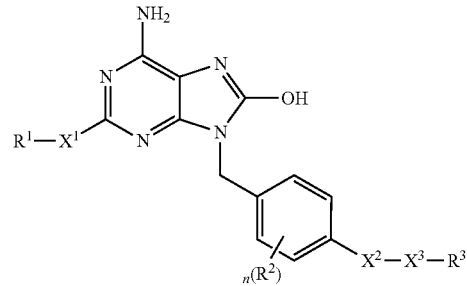

Formula B or a pharmaceutically acceptable salt, tautomer or hydrate thereof, where $X^2$ is a bond or linker, $X^3$ is bond or $—PO_4—$, and $X^1$, $R^1$, $R^2$, $R^3$, and n are described herein. Also provided in some embodiments are methods for making and using such compounds and compositions.

4 Claims, 37 Drawing Sheets

(56) References Cited

U.S. PATENT DOCUMENTS

| | | | |
|---|---|---|---|
| 6,734,187 | B1 | 5/2004 | Amemori et al. |
| 6,960,582 | B2 | 11/2005 | Boyce et al. |
| 7,157,465 | B2 | 1/2007 | Isobe et al. |
| 7,189,727 | B2 | 3/2007 | Boyce et al. |
| 7,241,890 | B2 | 7/2007 | Biamonte et al. |
| 7,521,454 | B2 | 4/2009 | Isobe et al. |
| 8,357,374 | B2 | 1/2013 | Carson et al. |
| 2002/0018808 | A1* | 2/2002 | Alving et al. ............ 424/450 |
| 2002/0193595 | A1 | 12/2002 | Boyce et al. |
| 2003/0187261 | A1 | 10/2003 | Berneman et al. |
| 2003/0191086 | A1 | 10/2003 | Hajduch et al. |
| 2004/0023211 | A1 | 2/2004 | Groen et al. |
| 2004/0132748 | A1 | 7/2004 | Isobe et al. |
| 2004/0248895 | A1 | 12/2004 | Boyce et al. |
| 2004/0265351 | A1 | 12/2004 | Miller et al. |
| 2005/0038027 | A1 | 2/2005 | Boyce et al. |
| 2005/0049263 | A1 | 3/2005 | Biamonte et al. |
| 2005/0054590 | A1 | 3/2005 | Averett et al. |
| 2006/0052403 | A1 | 3/2006 | Fujita et al. |
| 2007/0037832 | A1 | 2/2007 | Isobe et al. |
| 2007/0161582 | A1 | 7/2007 | Hranisavljevic et al. |
| 2007/0173483 | A1 | 7/2007 | Biamonte et al. |
| 2008/0008682 | A1 | 1/2008 | Chong et al. |
| 2008/0125446 | A1 | 5/2008 | Biamonte et al. |
| 2008/0214580 | A1 | 9/2008 | Ansari et al. |
| 2009/0047249 | A1 | 2/2009 | Graupe et al. |
| 2009/0069289 | A1 | 3/2009 | Ansari et al. |
| 2009/0105212 | A1 | 4/2009 | Hashimoto et al. |
| 2009/0118263 | A1 | 5/2009 | Hashimoto et al. |
| 2009/0131458 | A1 | 5/2009 | Lazarides et al. |
| 2009/0202484 | A1 | 8/2009 | Chong et al. |
| 2010/0210598 | A1 | 8/2010 | Carson et al. |
| 2012/0003298 | A1 | 1/2012 | Barberis et al. |
| 2012/0009247 | A1 | 1/2012 | Maj et al. |
| 2012/0083473 | A1 | 4/2012 | Holldack et al. |
| 2012/0148660 | A1 | 6/2012 | Carson et al. |
| 2013/0266635 | A1 | 10/2013 | Maj et al. |
| 2013/0267481 | A1 | 10/2013 | Maj et al. |

FOREIGN PATENT DOCUMENTS

| | | |
|---|---|---|
| EP | 1182208 | 2/2002 |
| EP | 2 674 170 | 12/2013 |
| JP | 11193282 | 7/1999 |
| JP | 2000159767 | 6/2000 |
| JP | 2001213867 | 8/2001 |
| JP | 2004137157 | 5/2004 |
| JP | 2005089334 | 4/2005 |
| WO | WO 99/24432 | 5/1999 |
| WO | WO 99/28321 | 6/1999 |
| WO | WO 00/43394 | 7/2000 |
| WO | WO 01/29320 | 3/2001 |
| WO | WO 01/49688 | 7/2001 |
| WO | WO 02/081443 | 10/2002 |
| WO | WO 02/085905 | 10/2002 |
| WO | WO 03/037860 | 5/2003 |
| WO | WO 2004/029054 | 4/2004 |
| WO | WO 2004/032829 | 4/2004 |
| WO | WO 2005/011708 | 2/2005 |
| WO | WO 2005/020892 | 3/2005 |
| WO | WO 2005/025583 | 3/2005 |
| WO | WO 2005/092892 | 10/2005 |
| WO | WO 2006/087538 | 8/2006 |
| WO | WO 2007/015877 | 2/2007 |
| WO | WO 2007/024707 | 3/2007 |
| WO | WO 2007/034817 | 3/2007 |
| WO | WO 2007/034881 | 3/2007 |
| WO | WO 2007/034882 | 3/2007 |
| WO | WO 2007/034917 | 3/2007 |
| WO | WO 2007/038720 | 4/2007 |
| WO | WO 2007/041863 | 4/2007 |
| WO | WO 2007/142755 | 12/2007 |
| WO | WO 2008/005555 | 1/2008 |
| WO | WO 2008/043031 | 4/2008 |
| WO | WO 2008/045529 | 4/2008 |
| WO | WO 2008/101867 | 8/2008 |
| WO | WO 2008/114008 | 9/2008 |
| WO | WO 2008/114817 | 9/2008 |
| WO | WO 2008/114819 | 9/2008 |
| WO | WO 2008/115319 | 9/2008 |
| WO | WO 2009/005687 | 1/2009 |
| WO | WO 2009/034386 | 3/2009 |
| WO | WO 2010/093436 | 8/2010 |
| WO | WO 2011/017611 | 2/2011 |
| WO | WO 2011/134668 | 11/2011 |
| WO | WO 2011/134669 | 11/2011 |
| WO | WO 2012/038058 | 3/2012 |

OTHER PUBLICATIONS

Dockrell and Kinghorn, "Imiquimod and resiquimod as novel immunomodulators" J. Antimicrob. Chemother. (2001) 48(6):751-5.

Meyer et al., "Induction of apoptosis by Toll-like receptor-7 agonist in tissue cultures" Br. J. Dermatol. (2003) 149 Suppl. 66:9-14.

Schon et al., "Tumor-Selective Induction of Apoptosis and the Small-Molecule Immune Response Modifier Imiquimod", J Natl Cancer Inst, 95(15), (2003), 1138-1149.

Schon et al., "Immune modulation and apoptosis induction: two sides of the antitumoral activity of imiquimod" Apoptosis (2004) 9(3):291-8.

Sidbury et al., "Topically applied imiquimod inhibits vascular tumor growth in vivo" J. Invest. Dermatol. (2003) 121(5):1205-9.

Stary et al., "Tumoricidal activity of TLR7/8-activated inflammatory dendritic cells" J. Exp. Med. (2007) 204(6):1441-51.

Stephanou and Latchman, "Opposing actions of STAT-1 and STAT-3" Growth Factors (2005) 23(3):177-82.

Sullivan et al., "Evaluation of superficial basal cell carcinomas after treatment with imiquimod 5% cream or vehicle for apoptosis and lymphocyte phenotyping" Dermatol. Surg. (2003) 29(12):1181-6.

Vidal et al., "Efficacy of imiquimod for the expression of Bcl-2, Ki67, p53 and basal cell carcinoma apoptosis" Br. J. Dermatol. (2004) 151(3):656-62.

Adams "Toll-like receptor agonists in cancer therapy," (2009) Immunotherapy 1:949-964.

American Cancer Society, "List of Cancers" © 2013, Available from <http://www.cancer.org/canger/showallcancertypes/index>.

Babjuk et al., "EAU guidelines on non-muscle-invasive urothelial carcinoma of the bladder." European Urology Aug. 2008;54(2):303-14.

Boonstra et al., "Macrophages and myeloid dendritic cells, but not plasmacytoid dendritic cells, produce IL-10 in response to MyD88- and TRIF-dependent TLR signals, and TLR-independent signals." Journal of Immunology, 177, 2006, 7551-7558.

Brandau "Thirty years of BCG immunotherapy for non-muscle invasive bladder cancer: A success story with room for improvement," J. Biomedicine & Pharmacotherapy Jul. 2007;61(8):299-305.

Broad et al., "Toll-like receptor (TLR) response tolerance: a key physiological "damage limitation" effect and an important potential opportunity for therapy," (2006) Curr Med Chem 13:2487-2502.

Brooke MS "Conversion of immunological paralysis to immunity by endotoxin." (1965) Nature 206:635-636.

Chan et al., "Synthesis and Immunological Characteristics of Toll-Like Receptor 7 Agonistic Conjugates," Bioconjugate Chemistry, (2009), 20(6), 1194-1200.

Choe JY, et al. "Interleukin 1 receptor dependence of serum transferred arthritis can be circumvented by toll-like receptor 4 signaling." (2003) J Exp Med 197:537-542.

Clarke et al., "Comparison of Rat and Human Response to Toll-like Receptor 7 Activation," Journal of Interferon & Cytokin Research (2009), 29(2), 113-126.

Cros et al., "Human CD14dim monocytes patrol and sense nucleic acids and viruses via TLR7 and TLR8 receptors." Immunity. 2010 33(3):375-86.

Dalpke, et al. "Differential effects of CpG-DNA in Toll-like receptor-2/-4/-9 tolerance and cross-tolerance.," (2005) Immunology 116:203-212.

(56) References Cited

OTHER PUBLICATIONS

Dharmapuri et al., "An oral TLR7 agonist is a potent adjuvant of DNA vaccination in transgenic mouse tumor models," Cancer Gene Therapy, (2009) 16(5), 462-472.
Douagi et al, "Human B cell responses to TLR ligands are differentially modulated by myeloid and plasmacytoid dendritic cells," Journal of Immunology, 182, 2009, 1991-2001.
Gantier et al. "TLR7 is involved in sequence-specific sensing of single-stranded RNAs in human macrophages," J Immunol. Feb. 15, 2008;180(4):2117-24.
Geng et al., "Exploring 9-benzyl purines as inhibitors of glutamate racemase (MurI) in Gram-positive bacteria," Bioorganic & Medicinal Chemistry Letters (2008), 18(15), 4368-4372.
Greisman SE, et al. "Mechanisms of endotoxin tolerance. The role of the spleen.", (1975) J Clin Invest 56:1597-1607.
Hanahan, Donald J. A guide go phospholipid Chemistry, Oxford University Press, New York, 1997. pp. 5-10.
Hanten J. A et al. "Comparison of human B cell activation by TLR7 and TLR9 agonists." (2008) BMC Immunol. 9, 39.
Hayashi et al. Intravesical Toll-like receptor 7 agonist IMIQUIMOD: Optimization of its formulation in an orthotopic mouse model of bladder cancer 1. International Journal of Urology May 2010;17(5):483-90.
Hayashi et al., "Prevention of autoimmune disease by induction of tolerance to Toll-like receptor 7," PNAS USA (2009), 106(8), 2764-2769.
Hayashi et al. "Mast cell-dependent anorexia and hypothermia induced by mucosal activation of Toll-like receptor 7." (2008) Am J Physiol Regul Integr Comp Physiol 295(1):R123-132.
Hemmi et al. Small anti-viral compounds activate immune cells via the TLR7 MyD88-dependent signaling pathway 1. Nature Immunology Feb. 2002;3(2):196-200.
Hendricksen et al., "Evaluation of an orthotopic rat bladder urothelial cell carcinoma model by cystoscopy," Bju International Apr. 2008;101(7):889-93.
Ida, "A whole blood assay to assess peripheral blood dendritic cell function in response to Toll-like receptor stimulation." Journal of Immunol Methods, 310, 2006, 86-99.
Jemal et al., "Cancer Statistics, 2009". Ca-A Cancer Journal for Clinicians Jul. 2009;59(4):225-49.
Kirkali et al. Bladder cancer: Epidemiology, staging and grading, and diagnosis. Urology Dec. 2005;66(6A):4-34.
Lee et al., "Molecular basis for the immunostimulatory activity of guanine nucleoside analogs: Activation of Toll-like receptor 7," PNAS, 100:6646 (2003).
Mantovani A, Sica A, Locati M. Macrophage polarization comes of age. Immunity. 2005; 23:344-346.
Mantovani, A., et al. 2004. The chemokine system in diverse forms of macrophage activation and polarization. Trends Immunol. 25:677-686.
Martinez, F.O., Sica, A., Mantovani, A., and Locati, M. 2008. Macrophage activation and polarization. Front. Biosci. 13:453-461.
Medical News Today. "What is Cancer? What Causes Cancer?" © Jul. 19, 2013 Available from <http://www.medicalnewstoday.com/info/cancer-oncolocy/>.
Medvedev et al., "Tolerance to microbial TLR ligands: molecular mechanisms and relevance to disease." J Endotoxin Res. 2006;12(3):133-50.
Miettinen et al., "Live *Lactobacillus rhamnosus* and *Streptococcus pyogenes* differentially regulate Toll-like receptor (TLR) gene expression in human primary macrophages.," J Leukoc Biol. 2008 84(4):1092-100.
Musmuca et al., "Small-Molecule Interferon Inducers. Toward the Comprehension of the Molecular Determinants through Ligand-Based Approaches," (2009), 49(7) 1777-1786.
Ploeg M, Aben KKH, Kiemeney LA. The present and future burden of urinary bladder cancer in the world 3. World Journal of Urology Jun. 2009;27(3):289-93.

Porta et al., "Tolerance and M2 (alternative) macrophage polarization are related processes orchestrated by p50 NF-kB." PNAS, 2009; 106(35):14978-83.
Prakken et al., "T Cell Repertoire Formation and Molecular Mimicry in Rheumatoid Arthritis," (2001) Curr Dir Autoimmun 3:51-63.
Prinz et al. "Innate immunity mediated by TLR9 modulates pathogenicity in an animal model of multiple sclerosis." (2006) J Clin Invest 116:456-464.
Rahman et al., "The role of toll-like receptors in systemic lupus erythematosus," (2006) Springer Semin Immunopathol 28:131-143.
Ricardo SD, et al. 2008. Macrophage diversity in renal injury and repair. J Clin Invest. 118:3522-3530.
Sato et al. "A variety of microbial components induce tolerance to lipopolysaccharide by differentially affecting MyD88-dependent and -independent pathways,"(2002) Int Immunol 14:782-791.
Seya et al., "Role of toll-like receptors and their adaptors in adjuvant immunotherapy for cancer," J. Anticancer Research Nov. 2003;23(6A):4369-76.
Smith et al. "Antitumor effects of imidazoquinolines in urothelial cell carcinoma of the bladder". Journal of Urology Jun. 2007;177(6):2347-51.
Sospedra et al, "Immunology of Multiple Sclerosis"(2005) Annu Rev Immunol 23:683-747.
Sylvester et al., "Predicting recurrence and progression in individual patients with stage Ta T1 bladder cancer using EORTC risk tables: A combined analysis of 2596 patients from seven EORTC trials." European Urology Mar. 2006;49(3):466-77.
Vultaggio et al., "Modified Adenine (9-Benzyl-2-Butoxy-8-Hydroxyadenine) Redirects Th2-Mediated Murine Lung Inflammation by Triggering TLD7," Journal of Immunology (2009), 182(2), 880-889.
Weterings et al., "2-Azidoalkoxy-7-hydro-8-oxoadenine derivatives as TLR7 agonists inducing dendritic cell maturation," Bioorganic & Medicinal Chemistry Letters (2009), 19(8), 2249-2251.
Witjes et al. "Clinical Practice Recommendations for the Prevention and Management of Intravesical Therapy-Associated Adverse Events," European Urology Supplements Oct. 2008;7(10):667-74.
Wu et al., "Immunotherapeudic activity of a conjugate of a Toll-like receptor 7 Ligand," PNAS USA (2007), 104(10), 3990-3995.
Xiao et al. Characterization of a novel transplantable orthotopic rat bladder transitional cell tumor model 3. British Journal of Cancer Oct. 1999;81(4):638-46.
International Search Report and Written Opinion dated: Jul. 12, 2011 in International Patent Application No. PCT/EP2011/002152 filed Apr. 29, 2011 and published as: WO/2011/134668 on Nov. 3, 2011.
International Preliminary Report on Patentability dated: Nov. 6, 2012 in International Patent Application No. PCT/EP2011/002152 filed Apr. 29, 2011 and published as: WO/2011/134668 on Nov. 3, 2011.
International Search Report and Written Opinion dated: Jul. 27, 2011 in International Patent Application No. PCT/EP2011/002153 filed Apr. 29, 2011 and published as: WO/2011/134669 on Nov. 3, 2011.
International Preliminary Report on Patentability dated: Nov. 6, 2012 in International Patent Application No. PCT/EP2011/002153 filed Apr. 29, 2011 and published as: WO/2011/134669 on Nov. 3, 2011.
International Search Report and Written Opinion dated: Dec. 2, 2011 in International Patent Application No. PCT/EP2011/004694 filed Sep. 20, 2011 and published as: WO/2012/038058 on: Mar. 29, 2012.
International Preliminary Report on Patentability dated: Mar. 26, 2013 in International Patent Application No. PCT/EP2011/004694 filed Sep. 20, 2011 and published as: WO/2012/038058 on: Mar. 29, 2012.
Office Action mailed: Nov. 21, 2013 in U.S. Appl. No. 13/097,838, filed Apr. 29, 2011.
Office Action mailed: Sep. 4, 2013 in U.S. Appl. No. 13/097,850, filed Apr. 29, 2011 and published as: 2012-0003298 on: Jan. 5, 2012.
Blasius et al., "Intracellular toll-like receptors" Immunity (2010) 32:305-315.
Fortin et al., "Trafficking of surface-linked and encapsulated liposomal antigens in macrophages: an immunocytochemical study" Journal of Histochemistry & Cytochemistry (2001) 49(11):1407-1420.

(56) References Cited

OTHER PUBLICATIONS

Russo et al., "Small molecule Toll-like receptor 7 agonists localize to the MHC class II loading compartment of human plasmacytoid dendritic cells" Blood (2011) 117(21):5683-5691.
Office Action dated May 5, 2014 in U.S. Appl. No. 13/097,850, filed Apr. 29, 2011 and published as US 2013-0003298 on Jan. 5, 2012.
Office Action dated May 7, 2014 in U.S. Appl. No. 13/772,253, filed Feb. 20, 2013 and published as US 2013-0266635 on Oct. 10, 2013.
Office Action dated May 8, 2014 in U.S. Appl. No. 13/772,235, filed Feb. 20, 2013 and published as US 2013-0267481 on Oct. 10, 2013.
The American Heritage Medical Dictionary Copyright, Proliferative enteropathy, 2007, 2004, by Houghton Mifflin Company, pp. 1-2, http://medical-dictionary.thefreedictionary.com/proliferative+hemorrhagic+enteropathy; accessed online May 4, 2014.
Belge et al., "Advances in treating psoriasis" F1000 Prime Reports, Faculty of 1000 Ltd. (2014) pp. 1-8.
Ghoreschi et al., "Selectivity and therapeutic inhibition of kinases: to be or not to be?" Nature Immunol. (2009) 10(4):356-360.
Lu et al., "TLR agonists for cancer immunotherapy: tipping the balance between the immune stimulatory and inhibitory effects" Frontiers in Immunology (2014) 5(83):1-4.
NCI, Cancer, Mar. 7, 2014, http://www.cancer.gov/cancertopics/cancerlibrary/what-is-cancer; accessed online May 4, 2014.
NCI, Bladder cancer, Jan. 2, 2014, http://www.cancer.gov/cancertopics/pdg/treatment/bladder/Patient/page4; accessed online May 4, 2014.
WebMD, Bladder Cancer, Apr. 30, 2013, http://www.webmd.com/cancer/bladder-cancer/bladder-cancer-prevention; accessed May 4, 2014.
WebMD, Psoriasis, Jan. 9, 2012, http://www.webmd.com/skin-problems-and-treatments/psoriasis/psoriasis-prevention; accessed May 4, 2014.
Office Action dated Jun. 20, 2014 in U.S. Appl. No. 13/097,838, filed Apr. 29, 2011 and published as US 2012-0009247 on Jan. 12, 2012.
Office Action dated Nov. 7, 2014 in U.S. Appl. No. 13/772,253, filed Feb. 20, 2013 and published as US 2013-0266635 on Oct. 10, 2013.
Office Action dated Nov. 7, 2014 in U.S. Appl. No. 13/772,235, filed Feb. 20, 2013 and published as US 2013-0267481 on Oct. 10, 2013.

* cited by examiner

FIG. 11

PHOSPHOLIPID CONJUGATE SERIES

| NAME | STRUCTURE | M.W. |
|---|---|---|
| COMPOUND A (NON-SATURATED C18 PHOSPHOLIPID CONJUGATE) | 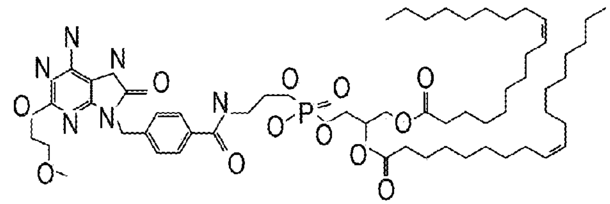 | 1085 |
| SC18 (SATURATED C18 PHOSPHOLIPID CONJUGATE) | 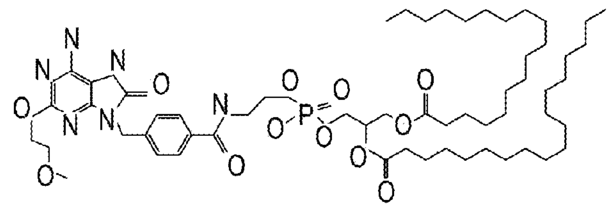 | 1089 |
| SC12 (SATURATED C12 PHOSPHOLIPID CONJUGATE) | 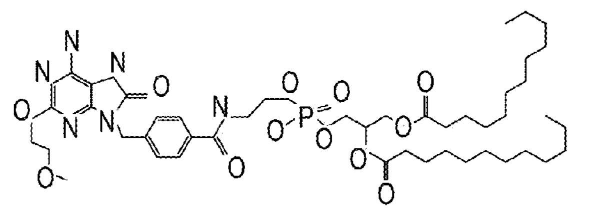 | 921 |
| SC8 (SATURATED C8 PHOSPHOLIPID CONJUGATE) | 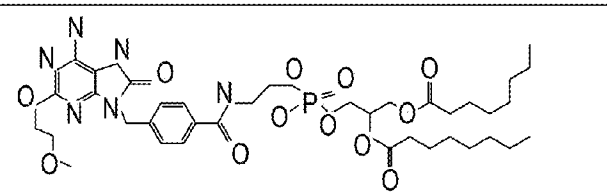 | 809 |

| HLA-DR+ CD123+ CD11C- (pDC) | MFI CD80 | MFI CD86 | MFI CCR7 |
|---|---|---|---|
| UNTREATED | | | |
| UNTREATED (DMSO) | 450 | 2057 | 100 |
| IMIQUIMOD 0.1 uM | 564 | 1781 | 138 |
| IMIQUIMOD 0.5 uM | 882 | 2225 | 266 |
| COMPOUND A 0.1 uM | 1081 | 2972 | 414 |
| COMPOUND A 0.5 uM | 1728 | 4231 | 771 |
| SC12 0.1 uM | 1440 | 4970 | 323 |
| SC12 0.5 uM | 2162 | 4838 | 563 |

| HLA-DR+ CD123- CD11C+ (mDC) | MFI CD80 | MFI CD86 | MFI CCR7 |
|---|---|---|---|
| UNTREATED | | | |
| UNTREATED (DMSO) | 504 | 10129 | 144 |
| IMIQUIMOD 0.1 uM | 910 | 11303 | 172 |
| IMIQUIMOD 0.5 uM | 1136 | 10622 | 842 |
| COMPOUND A 0.1 uM | 4206 | 13919 | 883 |
| COMPOUND A 0.5 uM | 4555 | 9729 | 281 |
| SC12 0.1 uM | 5270 | 10166 | 141 |
| SC12 0.5 uM | 6506 | 8924 | 203 |

| HLA-DR+ CD123+ CD11C- (pDC) | MFI CD80 | MFI CD86 | MFI CCR7 |
|---|---|---|---|
| UNTREATED | 549 | 2338 | 281 |
| UNTREATED (DMSO) | 565 | 2747 | 209 |
| IMIQUIMOD 0.1 uM | 571 | 2443 | 221 |
| IMIQUIMOD 0.5 uM | 1301 | 2079 | 307 |
| COMPOUND A 0.1 uM | 927 | 2234 | 572 |
| COMPOUND A 0.5 uM | 2148 | 4544 | 783 |
| SC12 0.1 uM | 1316 | 2957 | 346 |
| SC12 0.5 uM | 2329 | 4687 | 806 |

| HLA-DR+ CD123- CD11C+ (mDC) | MFI CD80 | MFI CD86 | MFI CCR7 |
|---|---|---|---|
| UNTREATED | 490 | 7765 | 149 |
| UNTREATED (DMSO) | 479 | 7218 | 85 |
| IMIQUIMOD 0.1 uM | 603 | 7057 | 124 |
| IMIQUIMOD 0.5 uM | 686 | 7060 | 205 |
| COMPOUND A 0.1 uM | 1753 | 9048 | 216 |
| COMPOUND A 0.5 uM | 5435 | 9382 | 511 |
| SC12 0.1 uM | 3333 | 8274 | 175 |
| SC12 0.5 uM | 4540 | 5724 | 292 |

| HLA-DR+<br>CD123+<br>CD11C-<br>(pDC) | MFI CD80 | MFI CD86 | MFI CCR7 |
|---|---|---|---|
| UNTREATED | 608 | 2831 | 337 |
| UNTREATED (DMSO) | 608 | 2103 | 535 |
| IMIQUIMOD 0.1 uM | 2745 | 2405 | 2696 |
| IMIQUIMOD 0.5 uM | 5168 | 6129 | 7067 |
| COMPOUND A 0.1 uM | 3241 | 4290 | 2968 |
| COMPOUND A 0.5 uM | 2413 | 5413 | 2910 |
| SC12 0.1 uM | 2799 | 6329 | 2478 |
| SC12 0.5 uM | 3899 | 4118 | 1107 |

| HLA-DR+ CD123- CD11C+ (mDC) | MFI CD80 | MFI CD86 | MFI CCR7 |
|---|---|---|---|
| UNTREATED | 522 | 9459 | 210 |
| UNTREATED (DMSO) | 416 | 10596 | 183 |
| IMIQUIMOD 0.1 uM | 1305 | 9909 | 1789 |
| IMIQUIMOD 0.5 uM | 2404 | 10100 | 2012 |
| COMPOUND A 0.1 uM | 3104 | 11928 | 2023 |
| COMPOUND A 0.5 uM | 5377 | 8739 | 1778 |
| SC12 0.1 uM | 3835 | 10982 | 929 |
| SC12 0.5 uM | 7646 | 8442 | 300 |

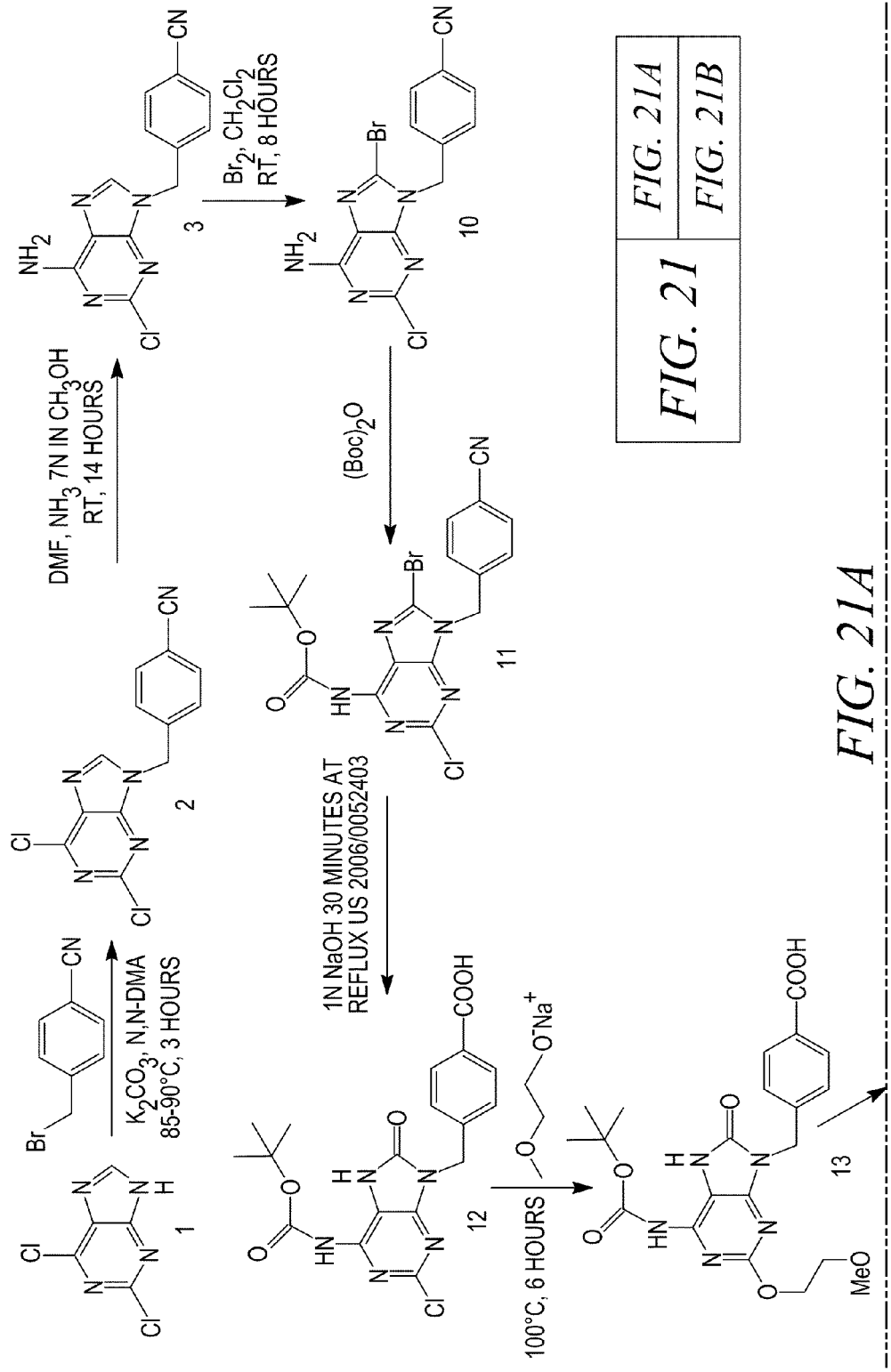

PHOSPHOLIPID DRUG ANALOGS

RELATED PATENT APPLICATIONS

This application is a continuation-in-part of U.S. patent application Ser. No. 13/097,838 filed Apr. 29, 2011, entitled PHOSPHOLIPID DRUG ANALOGS naming Roberto Maj, Franco Pattarino, Emanuela Mura and Alcide Barberis as inventors, which claims the benefit of U.S. provisional patent application No. 61/330,151 filed Apr. 30, 2010, entitled PHOSPHOLIPID DRUG ANALOGS, naming Alcide Barberis et al. as inventors. This application claims the benefit of U.S. provisional patent application No. 61/708,513 filed Oct. 1, 2012, entitled PHOSPHOLIPID DRUG ANALOGS, naming Roberto Maj, Franco Pattarino, Emanuela Mura and Alcide Barberis as inventors. Each of the foregoing patent applications is incorporated herein by reference in its entirety, including all text, tables and drawings.

FIELD

The technology relates in part to phospholipid drug analogs, and methods for manufacturing and using the same.

BACKGROUND

A pharmacophore often is a molecule that can exert a therapeutic effect in a subject. For example, a pharmacophore sometimes can exert an anti-cell proliferation effect, which can be useful for treating cell proliferation conditions such as cancer. A pharmacophore sometimes can stimulate the immune system in a subject, and thereby can generate or enhance an immune response against a particular antigen.

A pharmacophore can be conjugated (e.g., linked) to a phospholipid, or phospholipid-like molecule, in a phospholipid drug analog. A phospholipid, or phospholipid-like component, can impart a function to the analog that differs from the action of the unconjugated pharmacophore.

SUMMARY

Provided in some embodiments are compositions comprising a compound having a structure according to Formula A or Formula B:

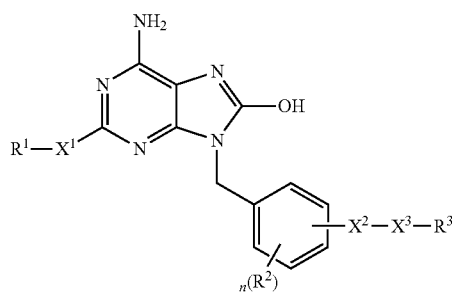

Formula A

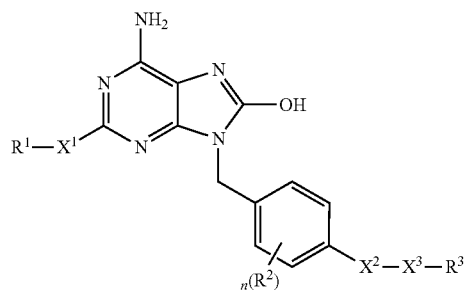

Formula B or a pharmaceutically acceptable salt, tautomer or hydrate thereof, where:

$X^1$ is —O—, —S—, or —$NR^a$—;

$R^a$ is hydrogen, C1-C10 alkyl, or substituted C1-C10 alkyl, or $R^a$ and $R^1$ taken together with the nitrogen atom can form a heterocyclic ring or a substituted heterocyclic ring, where the substituents on the alkyl or heterocyclic groups are hydroxy, C1-C10 alkyl, hydroxyl C1-C10 alkenyl, C1-C6 alkoxy, C3-C6 cycloalkyl, C1-C6 alkoxy C1-C6 alkylene, amino, cyano, halogen or aryl;

$R^1$ is hydrogen, C1-C10 alkyl, substituted C1-C10 alkyl, C1-C10 alkoxy, substituted C1-C10 alkoxy, C3-C9 cycloalkyl, substituted C3-C9 cycloalkyl, C5-C10 aryl, substituted C5-C10 aryl, C5-C9 heterocyclic, substituted C5-C9 heterocyclic, C1-C6 alkanoyl, Het, Het C1-C6 alkyl, or C1-C6 alkoxycarbonyl, where the substituents on the alkyl, cycloalkyl, alkanoyl, alkcoxycarbonyl, Het, aryl or heterocyclic groups are hydroxyl, C1-C10 alkyl, hydroxyl C1-C10 alkylene, C1-C6 alkoxy, C3-C9 cycloalkyl, C5-C9 heterocyclic, C16 alkoxy C16 alkenyl, amino, cyano, halogen or aryl;

each $R^2$ independently is hydrogen, —OH, C1-C6 alkyl, substituted C1-C6 alkyl, C1-C6 alkoxy, substituted C1-C6 alkoxy, —C(O)—C1-C6 alkyl (alkanoyl), substituted —C(O)—C1-C6 alkyl, —C(O)—C6-C10 aryl (aroyl), substituted —C(O)—C6-C10 aryl, —C(O)OH (carboxyl), —C(O)O—C1-C6 alkyl (alkoxycarbonyl), substituted —C(O)O—C1-C6 alkyl, —$NR^aR^b$, —C(O)$NR^bR^c$ (carbamoyl), substituted C(O)$NR^bR^c$, C5-C9 cyclic, substituted C5-C9 cyclic, C5-C9 heterocyclic, substituted C5-C9 heterocyclic, halo, nitro, or cyano, where the substituents on the alkyl, cyclic, aryl or heterocyclic groups are hydroxy, C1-C10 alkyl, hydroxyl C1-C10 alkylene, C1-C6 alkoxy, C3-C6 cycloalkyl, C1-C6 alkoxy C1-C6 alkylene, amino, cyano, halogen or aryl;

each $R^b$ and $R^c$ independently is hydrogen, C1-C10 alkyl, substituted C1-C10 alkyl, C1-C10 alkoxy, substituted C1-C10 alkoxy, C3-C9 cycloalkyl, substituted C3-C9 cycloalkyl, C5-C10 aryl, substituted C5-C10 aryl, C5-C9 heterocyclic, substituted C5-C9 heterocyclic, C1-C6 alkanoyl, Het, Het C1-C6 alkyl, or C1-C6 alkoxycarbonyl, where the substituents on the alkyl, cycloalkyl, alkanoyl, alkcoxycarbonyl, Het, aryl or heterocyclic groups are hydroxyl, C1-C10 alkyl, hydroxyl C1-C10 alkylene, C1-C6 alkoxy, C3-C9 cycloalkyl, C5-C9 heterocyclic, C16 alkoxy C16 alkenyl, amino, cyano, halogen or aryl;

$X^2$ is a bond or a linking group; n is 0, 1, 2, 3 or 4; and $X^3$ is a bond or a —$PO_4$—;

$R^3$ is a C1-C6 alkyl substituted with —OC(O)—$R^d$ and —OC(O)—$R^e$; C1-C6 alkyl substituted with —OC (O)—$R^d$, —OC(O)—$R^e$, and one or more further substituents; C1-C6 alkenyl substituted with —OC(O)—$R^d$ and —OC(O)—$R^e$; or C1-C6 alkenyl substituted with —OC(O)—$R^d$, —OC(O)—$R^e$, and one or more further substituents; where the one or more further substituents independently are hydroxyl, C1-C10 alkyl, hydroxyl C1-C10 alkylene, C1-C6 alkoxy, C3-C9 cycloalkyl, C5-C9 heterocyclic, C16 alkoxy C16 alkylene, amino, cyano, halogen or aryl;

each $R^d$ and $R^e$ independently is a linear C10 to C16 alkyl or linear C10 to C16 alkyl substituted with one or more of hydroxyl, C1-C10 alkyl, hydroxyl C1-C10 alkylene, C1-C6 alkoxy, C3-C6 cycloalkyl, C16 alkoxy C16 alkylene, amino, cyano, epoxy, halogen or aryl.

In certain embodiments, $R^d$ and $R^e$ independently are a linear and saturated C10, C11, C12, C13, C14, C15 or C16 alkyl, and in some embodiments $R^d$ and $R^e$ are the same or different. Non-limiting examples of —OC(O)—$R^d$ and —OC(O)—$R^e$ independently include n-decanoyl (C10, —OC(O)—$(CH_2)_8CH_3$), n-dodecanoyl (C12, lauroyl, —OC(O)—$(CH_2)_{10}CH_3$), n-tetradecanoyl (C14, myristoyl, —OC(O)—$(CH_2)_{12}CH_3$), and n-hexadecanoyl (C16, palmitoyl, —OC(O)—$(CH_2)_{14}CH_3$). $R^d$ and $R^e$, in some embodiments, independently are a linear and saturated C11 to C15 alkyl. Sometimes $R^d$ and $R^e$ independently are a linear and saturated C10, C11, C12, C13, C14, C15 or C16 alkyl. In some embodiments, $R^d$ and $R^e$ independently are a linear and saturated C10-C16 alkyl (e.g., C10, C11, C12, C13, C14, C15 or C16 alkyl), or a linear C10-C16 alkyl substituted with one or more of hydroxyl, C1-C10 alkyl, hydroxyl C1-C10 alkylene, C1-C6 alkoxy, C3-C6 cycloalkyl, C16 alkoxy C16 alkylene, amino, cyano, epoxy, halogen or aryl. In some embodiments, $R^d$ and $R^e$ are linear and saturated (for example, SC12 and SC14), and in some embodiments, $R^d$ and $R^e$ are linear and nonsaturated (for example, Compound A). Each linear C10, C11, C12, C13, C14, C15 or C16 alkyl or substituted variant thereof sometimes is fully saturated and contains no unsaturation (i.e., double bond). Each linear C10, C11, C12, C13, C14, C15 or C16 alkyl is an alkyl moiety having 10, 11, 12, 13, 14, 15 or 16 carbon atoms, respectively.

In specific embodiments, each $R^d$ and $R^e$ is a saturated and linear C1-2 alkyl. In some embodiments, $R^d$ and $R^e$ are not substituted by an epoxy moiety, and sometimes $R^d$ and $R^e$ are not substituted by a hydroxyl moiety. In specific embodiments, $R^d$ and $R^e$ are not substituted by an epoxy moiety or a hydroxyl moiety. In various embodiments, $R^d$ and $R^e$ include no double bond (e.g., no unsaturation).

In some embodiments, —$X^2$—$X^3$—$R^3$ together form a structure according to Formula C:

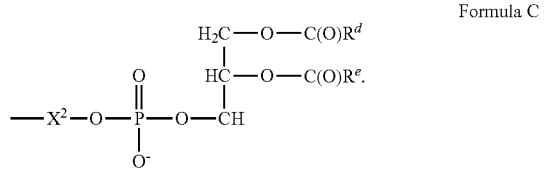

Formula C

In certain embodiments —$X^2$—$X^3$—$R^3$ taken together form a structure according to Formula D:

Formula D

In some embodiments, $X^1$ is O, and sometimes $R^1$ is a C1-C10 alkyl substituted with a C16 alkoxy. In certain embodiments n is 0 and $X^2$ is —C(O)NH—$(CH_2)_2$—. Sometimes $R^3$ is a C3 alkyl substituted with —OC(O)—$R^d$ and —OC(O)—$R^e$, and in certain embodiments, the $R^3$ C3 alkyl is substituted with —OC(O)—$R^d$ at position 3 and —OC(O)—$R^e$ at position 2 of the C3 alkyl (e.g., see Formula C, where the —$PO_4$— moiety is linked to position 1 of the C3 alkyl, the —OC(O)—$R^e$ moiety is at position 2 and the —OC(O)—$R^d$ moiety is at position 3). In specific embodiments, $X^1$ is O, $R^1$ is —$(CH_2)_2$—$OCH_3$, n is 0, $X^2$ is —C(O)NH—$(CH_2)_2$—, $X^3$ is —$PO_4$—, $R^3$ is a C3 alkyl substituted with —OC(O)—$R^d$ and —OC(O)—$R^e$. In some embodiments, $R^d$ and $R^e$ are not substituted by an epoxy moiety and/or are not substituted by a hydroxyl moiety.

In some embodiments, the benzene ring in Formula A or Formula B is replaced with a non-aromatic ring, a heterocyclic non-aromatic ring, or a heterocyclic aromatic ring. Examples of these rings include, for example, those listed herein. Non-limiting examples of non-aromatic rings include any 5- or 6-membered cycloalkyl or heterocyclic moieties. Non-limiting examples of heterocyclic non-aromatic rings include piperidine and piperazine. Non-limiting examples of heterocyclic aromatic rings include, for example, pyridine, pyrazine, pyrimidine, pyridazine, and triazine.

In certain embodiments, a composition comprises a liposome. A composition in some embodiments comprises an antigen.

Provided also in some embodiments are immunostimulatory compositions comprising a compound having a structure described herein. In certain embodiments, the compound functions as an adjuvant, and sometimes an immunostimulatory composition comprises an antigen (e.g., the composition functions as a vaccine). An immunostimulatory composition in some embodiments comprises a vaccine, and in some embodiments an immunostimulatory composition is a primary vaccine or combination vaccine.

Also provided are methods of treating a condition in a subject which comprises administering a composition described herein to a subject in need thereof in an amount effective to treat the condition. In some embodiments the subject is a mammal, such as a human, for example. In some embodiments the condition is a cancer condition, such as a bladder cancer condition, for example. In some embodiments the composition is administered by intravesical instillation or by topical delivery to a bladder. In some embodiments, the condition is a microbial infection. In some embodiments, the condition is a skin precancerous or cancerous condition.

Also provided are methods of inducing an immune response comprising administering to a subject a compound having a structure provided herein. By inducing an immune response is meant inducing an immune response to a specific antigen, or inducing a general immune response (in the absence of a specific antigen). In one embodiment, the compound acts as an adjuvant and so is associated with a specific, not a general immune response. In one embodiment, the compound acts as a general immune stimulator. In one embodiment, the method includes administering to a mammal in need thereof an amount of an antigen and a compound having a structure provided herein effective to prevent, inhibit or treat disorders, including but not limited to bladder cancer or skin cancer. Thus, in certain embodiments, the immune response is an antigen-specific immune response. In some embodiments, the immune response is an antibody response, which sometimes is, for example, a IgG1 or a IgG2a antibody response. In some embodiments, the antigen is a microbial antigen, for example, a Malaria antigen may be administered, in some embodiments, the antigen is an *E. coli* antigen. The antigen and the compound sometimes are in one composition, and in some embodiments the antigen and the compound are in different compositions. The compound and/or antigen in certain embodiments is in association with a liposome. The antigen and the compound may be administered at the same time, or at different times. In some embodiments, the antigen is administered before the compound, in other embodiments, the antigen is administered at the same time as the compound, in other embodiments, the antigen is administered after the compound. In some embodiments, the immune response is an antigen specific immune response. In certain embodiments, the immune response is an antibody response, which sometimes is an IgG2a antibody response.

In some embodiments the subject is a mammal, such as a human, for example. In certain embodiments, the compound is administered to the bladder, such as by intra-vesical instillation/topical delivery, in non-limiting embodiments.

In some embodiments, the compound is administered to the skin, for example, by topical delivery. Also provided in certain embodiments are methods for treating a condition in a subject, which comprise administering a composition described herein to a subject in need thereof in an amount effective to treat the condition. Provided also in some embodiments are methods for treating a condition in a subject, which comprise administering an immunostimulatory composition described herein to a subject in need thereof in an amount effective to treat the condition. The subject sometimes is a mammal, and can be a human in certain embodiments. The condition sometimes is a cancer condition, and the condition can be a microbial infection. In specific embodiments, the condition is a bladder cancer condition, and the composition can be administered by intravesical instillation/topical delivery to the bladder, in certain embodiments. In some embodiments, the cancer is a skin cancer, and the compounds can be administered locally and/or topically, for example, by topical delivery to the skin, in a cream, ointment, gel, lotion or other appropriate vehicle. Skin precancerous conditions and skin cancers that may be treated include, for example, actinic keratosis (AK), basal cell carcinoma (BCC), squamous cell carcinoma (SCC), melanoma and non-melanoma skin cancer.

Certain embodiments are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIG. 11 shows structures and molecular weights of phospholipid analogs SC8, SC12 and SC18.

FIGS. 21A and 21B provide an example of a synthetic scheme for synthesis of compound A and SC12.

FIGS. 24A, 24B and 24C represent PBMCs isolated from human donors 1, 2 and 3 respectively.

FIGS. 25A, 25B and 25C represent PBMCs isolated from human donors 1, 2 and 3 respectively.

DETAILED DESCRIPTION

Figure 1:
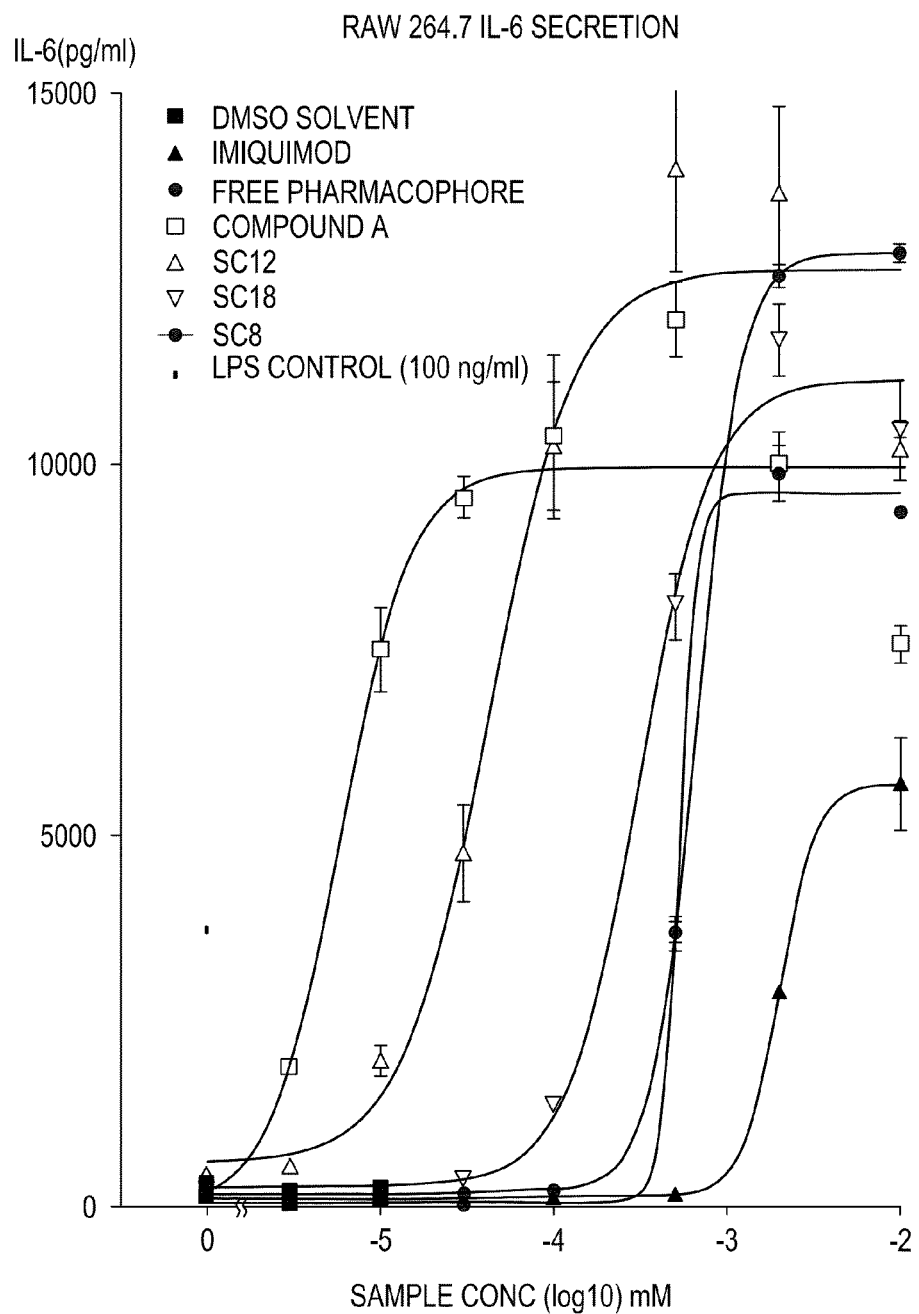
FIG. 1 illustrates cytokine production for compounds in Raw264.7 mouse macrophage cell line studies.

Compositions provided herein may be useful for treating certain conditions, such as cell proliferation conditions, for example. A variety of cell proliferation conditions exist, superficial bladder cancer being an example of one type.

Compositions provided herein also may serve as a vaccine, and compounds described may facilitate an immune response and provide adjuvant activity.

Compositions provided include phospholipid analogs in certain embodiments. A phospholipid analog often includes a pharmocophore portion and a phospholipid, or phospholipid-like, portion conjugated to the pharmacophore portion via a linker.

Without being limited by theory, compositions described herein may modulate an activity of one or more toll-like receptors (e.g., the conjugates are agonists, antagonists, or both). The term "toll-like receptor" (TLR) refers to a member of a family of receptors that bind to pathogen-associated molecular patterns (PAMPs) and facilitate an immune response in a mammal. Ten mammalian TLRs are known, e.g., TLR1-10. The term "toll-like receptor agonist" (TLR agonist) refers to a molecule that interacts with a TLR and stimulates the activity of the receptor. Synthetic TLR agonists are chemical compounds that are designed to interact with a TLR and stimulate the activity of the receptor. The term "toll-like receptor antagonist" (TLR antagonist) refers to a molecule that interacts with a TLR and inhibits or neutralizes the signaling activity of the receptor. Synthetic TLR antagonists are chemical compounds designed to interact with a TLR and interfere with the activity of the receptor. Agonists and/or antagonists of a TLR sometimes modulate the activity of a TLR-7, TLR-3 or TLR-9. Local activation of a TLR may disrupt cancer cell-matrix interactions required for growth and survival of malignant cells and may induce apoptosis.

Also, without being limited by theory, compounds provided herein can be characterized as having an advantageous stability. For example, certain compounds described herein can be characterized as having an advantageous chemical stability and/or metabolic stability under physiologic conditions.

Compounds

As used herein, the terms "alkyl," "alkenyl" and "alkynyl" include straight-chain (referred to herein as "linear"), branched-chain (referred to herein as "non-linear"), cyclic monovalent hydrocarbyl radicals, and combinations of these, which contain only C and H atoms when they are unsubstituted. Non-limiting examples of alkyl moieties include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms it can be represented as 1-10C or as C1-C10 or C1-10. When heteroatoms (N, O and S typically) are allowed to replace carbon atoms as in heteroalkyl groups, for example, the numbers describing the group, though still written as e.g. C1-C6, represent the sum of the number of carbon atoms in the group plus the number of such heteroatoms that are included as replacements for carbon atoms in the backbone of the ring or chain being described. An alkyl that contains only C and H atoms and is unsubstituted sometimes is referred to as "saturated." An alkenyl or alkynyl generally is "unsaturated" as it contains one or more double bonds or triple bonds, respectively. An alkenyl can include any number of double bonds, such as 1, 2, 3, 4 or 5 double bonds, for example. An alkynyl can include any number of triple bonds, such as 1, 2, 3, 4 or 5 triple bonds, for example.

Alkyl, alkenyl and alkynyl substituents sometimes contain 1-10C (alkyl) or 2-10C (alkenyl or alkynyl). They can contain 1-8C (alkyl) or 2-8C (alkenyl or alkynyl) in some embodiments. Sometimes they contain 1-4C (alkyl) or 2-4C (alkenyl or alkynyl). A single group can include more than one type of multiple bond, or more than one multiple bond. Such groups are included within the definition of the term "alkenyl" when they contain at least one carbon-carbon double bond, and are included within the term "alkynyl" when they contain at least one carbon-carbon triple bond.

Alkyl, alkenyl and alkynyl groups often are optionally substituted to the extent that such substitution can be synthesized and can exist. Typical substituents include, but are not limited to, halo, =O, =N—CN, =N—OR, =NR, OR, $NR_2$, SR, $SO_2R$, $SO_2NR_2$, $NRSO_2R$, $NRCONR_2$, NRCOOR, NRCOR, CN, COOR, $CONR_2$, OOCR, COR, and $NO_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halo, =O, =N—CN, =N—OR', =NR', OR', $NR'_2$, SR', $SO_2R'$, $SO_2NR'_2$, $NR'SO_2R'$, $NR'CONR'_2$, NR'COOR', NR'COR', CN, COOR', $CONR'_2$, OOCR', COR', and $NO_2$, wherein each R' is independently H, C1-C8 alkyl, C2-C8 heteroalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group.

"Acetylene" substituents are 2-10C alkynyl groups that are optionally substituted, and are of the formula —C≡C—Ri, wherein Ri is H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C1-2 arylalkyl, or C6-C1-2 heteroarylalkyl, and each Ri group is optionally substituted with one or more substituents selected from halo, =O, =N—CN, =N—OR', =NR', OR', NR'2, SR', $SO_2R'$, $SO_2NR'_2$, $NR'SO_2R'$, $NR'CONR'_2$, NR'COOR', NR'COR', CN, COOR', $CONR'_2$, OOCR', COR', and $NO_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O; and where two R' can be linked to form a 3-7 membered ring optionally containing up to three heteroatoms selected from N, O and S. In some embodiments, Ri of —C≡C—Ri is H or Me.

"Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain one to three O, S or N heteroatoms or combinations thereof within the backbone residue; thus at least one carbon atom of a corresponding alkyl, alkenyl, or alkynyl group is replaced by one of the specified heteroatoms to form a heteroalkyl, heteroalkenyl, or heteroalkynyl group. The typical and preferred sizes for heteroforms of alkyl, alkenyl and alkynyl groups are generally the same as for the corresponding hydrocarbyl groups, and the substituents that may be present on the heteroforms are the same as those described above for the hydrocarbyl groups. For reasons of chemical stability, it is also understood that, unless otherwise specified, such groups do not include more than two contiguous heteroatoms except where an oxo group is present on N or S as in a nitro or sulfonyl group.

While "alkyl" as used herein includes cycloalkyl and cycloalkylalkyl groups, the term "cycloalkyl" may be used herein to describe a carbocyclic non-aromatic group that is connected via a ring carbon atom, and "cycloalkylalkyl" may be used to describe a carbocyclic non-aromatic group that is connected to the molecule through an alkyl linker. Similarly, "heterocyclyl" may be used to describe a non-aromatic cyclic group that contains at least one heteroatom as a ring member and that is connected to the molecule via a ring atom, which may be C or N; and "heterocyclylalkyl" may be used to describe such a group that is connected to another molecule through a linker. The sizes and substituents that are suitable for the cycloalkyl, cycloalkylalkyl, heterocyclyl, and heterocyclylalkyl groups are the same as those described above for alkyl groups. As used herein, these terms also include rings that contain a double bond or two, as long as the ring is not aromatic.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)NR$_2$ as well as —C(=O)-heteroaryl.

Acyl and heteroacyl groups are bonded to any group or molecule to which they are attached through the open valence of the carbonyl carbon atom. Typically, they are C1-C8 acyl groups, which include formyl, acetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

"Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5 membered rings as well as 6 membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. The monocyclic heteroaryls sometimes contain 5-6 ring members, and the bicyclic heteroaryls sometimes contain 8-10 ring members.

Aryl and heteroaryl moieties may be substituted with a variety of substituents including C1-C8 alkyl, C2-C8 alkenyl, C2-C8 alkynyl, C5-C12 aryl, C1-C8 acyl, and heteroforms of these, each of which can itself be further substituted; other substituents for aryl and heteroaryl moieties include halo, OR, NR$_2$, SR, SO$_2$R, SO$_2$NR$_2$, NRSO$_2$R, NRCONR$_2$, NRCOOR, NRCOR, CN, COOR, CONR$_2$, OOCR, COR, and NO$_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C6-C10 aryl, C5-C10 heteroaryl, C7-C12 arylalkyl, or C6-C12 heteroarylalkyl, and each R is optionally substituted as described above for alkyl groups. The substituent groups on an aryl or heteroaryl group may be further substituted with the groups described herein as suitable for each type of such substituents or for each component of the substituent. Thus, for example, an arylalkyl substituent may be substituted on the aryl portion with substituents typical for aryl groups, and it may be further substituted on the alkyl portion with substituents as typical or suitable for alkyl groups.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. A linker often is C1-C8 alkyl or a hetero form thereof. These linkers also may include a carbonyl group, thus making them able to provide substituents as an acyl or heteroacyl moiety. An aryl or heteroaryl ring in an arylalkyl or heteroarylalkyl group may be substituted with the same substituents described above for aryl groups. An arylalkyl group sometimes includes a phenyl ring optionally substituted with the groups defined above for aryl groups and a C1-C4 alkylene that is unsubstituted or is substituted with one or two C1-C4 alkyl groups or heteroalkyl groups, where the alkyl or heteroalkyl groups can optionally cyclize to form a ring such as cyclopropane, dioxolane, or oxacyclopentane. Similarly, a heteroarylalkyl group often includes a C5-C6 monocyclic heteroaryl group optionally substituted with one or more of the groups described above as substituents typical on aryl groups and a C1-C4 alkylene that is unsubstituted. A heteroarylalkyl group sometimes is substituted with one or two C1-C4 alkyl groups or heteroalkyl groups, or includes an optionally substituted phenyl ring or C5-C6 monocyclic heteroaryl and a C1-C4 heteroalkylene that is unsubstituted or is substituted with one or two C1-C4 alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on the alkyl or heteroalkyl portion or on the aryl or heteroaryl portion of the group. The substituents optionally present on the alkyl or heteroalkyl portion sometimes are the same as those described above for alkyl groups, and the substituents optionally present on the aryl or heteroaryl portion often are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl includes pyridylmethyl, phenoxy, and N-pyrrolyl methoxy.

"Alkylene" as used herein refers to a divalent hydrocarbyl group. Because an alkylene is divalent, it can link two other groups together. An alkylene often is referred to as —(CH$_2$)$_n$— where n can be 1-20, 1-10, 1-8, or 1-4, though where specified, an alkylene can also be substituted by other groups, and can be of other lengths, and the open valences need not be at opposite ends of a chain. Thus —CH(Me)— and —C(Me)$_2$— may also be referred to as alkylenes, as can a cyclic group such as cyclopropan-1,1-diyl. Where an alkylene group is substituted, the substituents include those typically present on alkyl groups as described herein.

A suitable linker can be utilized to construct a phospholipid analog (e.g., X$^2$), and multiple linkers are known. Non-limiting examples of linkers include —(Y)$_y$—, —(Y)$_y$—C(O)N—(Z)$_z$—, —(CH$_2$)$_y$—C(O)N—(CH$_2$)$_z$—, —(Y)$_y$—NC(O)—(Z)$_z$—, —(CH$_2$)$_y$—NC(O)—(CH$_2$)$_z$—, where each y (subscript) and z (subscript) independently is 0 to 20 and each Y and Z independently is C1-C10 alkyl, substituted C1-C10 alkyl, C1-C10 alkoxy, substituted C1-C10 alkoxy, C3-C9 cycloalkyl, substituted C3-C9 cycloalkyl, C5-C10 aryl, substituted C5-C10 aryl, C5-C9 heterocyclic, substituted C5-C9 heterocyclic, C1-C6 alkanoyl, Het, Het C1-C6 alkyl, or C1-C6 alkoxycarbonyl, wherein the substituents on the alkyl, cycloalkyl, alkanoyl, alkcoxycarbonyl, Het, aryl or heterocyclic groups are hydroxyl, C1-C10 alkyl, hydroxyl C1-C10 alkylene, C1-C6 alkoxy, C3-C9 cycloalkyl, C5-C9 heterocyclic, C16 alkoxy C16 alkenyl, amino, cyano, halogen or aryl. In certain embodiments, a linker sometimes is a —C(Y')(Z')—C(Y")(Z")— linker, where each Y', Y", Z' and Z" independently is hydrogen C1-C10 alkyl, substituted C1-C10 alkyl, C1-C10 alkoxy, substituted C1-C10 alkoxy, C3-C9 cycloalkyl, substituted C3-C9 cycloalkyl, C5-C10 aryl, substituted C5-C10 aryl, C5-C9 heterocyclic, substituted C5-C9 heterocyclic, C1-C6 alkanoyl, Het, Het C1-C6 alkyl, or C1-C6 alkoxycarbonyl, wherein the substituents on the alkyl, cycloalkyl, alkanoyl, alkcoxycarbonyl, Het, aryl or heterocyclic groups are hydroxyl, C1-C10 alkyl, hydroxyl C1-C10 alkylene, C1-C6 alkoxy, C3-C9 cycloalkyl, C5-C9 heterocyclic, C16 alkoxy C16 alkenyl, amino, cyano, halogen or aryl. Certain non-limiting examples of linkers that can be utilized include the following:

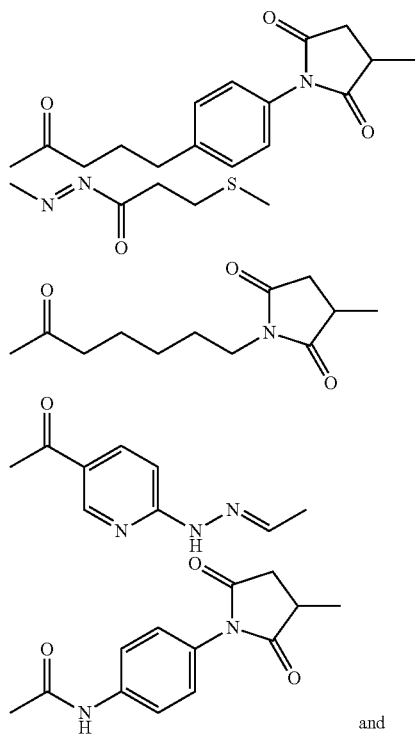

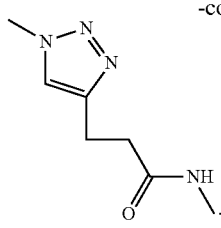

and

In some embodiments, a linker is selected that results in a suitable plasma stability. A suitable stability sometimes is about 60% or more (e.g., about 65%, 70%, 75%, 80%, 85%, 90%) of the conjugate analog present after contact with human plasma for about 300 minutes.

In general, any alkyl, alkenyl, alkynyl, acyl, or aryl or arylalkyl group, or any heteroform of one of these groups, that is contained in a substituent may itself optionally be substituted by additional substituents. The nature of these substituents is similar to those recited with regard to the primary substituents themselves if the substituents are not otherwise described. Thus, where an embodiment of, for example, R$^1$ is alkyl, this alkyl may optionally be substituted by the remaining substituents listed as embodiments for R$^1$ where this makes chemical sense, and where this does not undermine the size limit provided for the alkyl per se; e.g., alkyl substituted by alkyl or by alkenyl would simply extend the upper limit of carbon atoms for these embodiments, and is not included. However, alkyl substituted by aryl, amino, alkoxy, =O, and the like would be included within the scope of the invention, and the atoms of these substituent groups are not counted in the number used to describe the alkyl, alkenyl, etc. group that is being described. Where no number of substituents is specified, each such alkyl, alkenyl, alkynyl, acyl, or aryl group may be substituted with a number of substituents according to its available valences; in particular, any of these groups may be substituted with fluorine atoms at any or all of its available valences, for example.

"Heteroform" as used herein refers to a derivative of a group such as an alkyl, aryl, or acyl, wherein at least one carbon atom of the designated carbocyclic group has been replaced by a heteroatom selected from N, O and S. Thus the heteroforms of alkyl, alkenyl, alkynyl, acyl, aryl, and arylalkyl are heteroalkyl, heteroalkenyl, heteroalkynyl, heteroacyl, heteroaryl, and heteroarylalkyl, respectively. It is understood that no more than two N, O or S atoms are ordinarily connected sequentially, except where an oxo group is attached to N or S to form a nitro or sulfonyl group. A heteroform moiety sometimes is referred to as "Het" herein.

"Halo" or "halogen," as used herein includes fluoro, chloro, bromo and iodo. Fluoro and chloro are often preferred. "Amino" as used herein refers to NH$_2$, but where an amino is described as "substituted" or "optionally substituted", the term includes NR'R" wherein each R' and R" is independently H, or is an alkyl, alkenyl, alkynyl, acyl, aryl, or arylalkyl group or a heteroform of one of these groups, and each of the alkyl, alkenyl, alkynyl, acyl, aryl, or arylalkyl groups or heteroforms of one of these groups is optionally substituted with the substituents described herein as suitable for the corresponding group. The term also includes forms wherein R' and R" are linked together to form a 3-8 membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

As used herein, the term "carbocycle" refers to a cyclic compound containing only carbon atoms in the ring, whereas a "heterocycle" refers to a cyclic compound comprising a heteroatom. The carbocyclic and heterocyclic structures encompass compounds having monocyclic, bicyclic or multiple ring systems. As used herein, the term "heteroatom" refers to any atom that is not carbon or hydrogen, such as nitrogen, oxygen or sulfur. Illustrative examples of heterocycles include but are not limited to tetrahydrofuran, 1,3 dioxolane, 2,3 dihydrofuran, pyran, tetrahydropyran, benzofuran, isobenzofuran, 1,3 dihydro isobenzofuran, isoxazole, 4,5 dihydroisoxazole, piperidine, pyrrolidine, pyrrolidin 2 one, pyrrole, pyridine, pyrimidine, octahydro pyrrolo[3,4b] pyridine, piperazine, pyrazine, morpholine, thiomorpholine, imidazole, imidazolidine 2,4 dione, 1,3 dihydrobenzimidazol 2 one, indole, thiazole, benzothiazole, thiadiazole, thiophene, tetrahydro thiophene 1,1 dioxide, diazepine, triazole, guanidine, diazabicyclo[2.2.1]heptane, 2,5 diazabicyclo[2.2.1] heptane, 2,3,4,4a,9,9a hexahydro 1H beta carboline, oxirane, oxetane, tetrahydropyran, dioxane, lactones, aziridine, azetidine, piperidine, lactams, and may also encompass heteroaryls. Other illustrative examples of heteroaryls include but are not limited to furan, pyrrole, pyridine, pyrimidine, imidazole, benzimidazole and triazole.

In some cases, compounds described herein contain one or more chiral centers. The technology includes each of the isolated stereoisomeric forms as well as mixtures of stereoisomers in varying degrees of chiral purity, including racemic mixtures. It also encompasses the various diastereomers and tautomers that can be formed. A compound described herein also may exist in one or more tautomeric forms. For example, when R is —OH, a compound described herein may exist in one or more tautomeric forms. A compound described herein can exist as a particular salt. Non-limiting examples of pharmaceutically acceptable salts are described herein.

The term "optionally substituted" as used herein indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. Where an optional substituent is attached via a double bond, such as a carbonyl oxygen (═O), the group takes up two available valences, so the total number of substituents that may be included is reduced according to the number of available valences.

Phospholipid Analog Pharmacophores

Provided in certain embodiments are compositions comprising a compound according to Formula E:

$$P^1—X^2—X^3—R^3 \qquad \text{Formula E}$$

or a pharmaceutically acceptable salt or hydrate thereof, where $X^2$, $X^3$ and $R^3$ are as described above, and $P^1$ is a pharmacophore.

In some embodiments, provided also are compositions comprising a compound according to Formula F or Formula G:

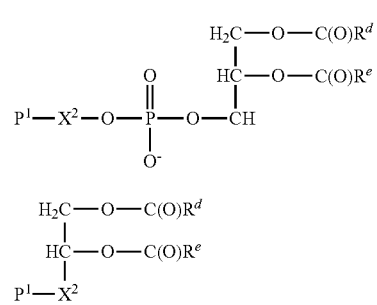

Formula F

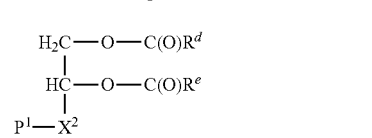

Formula G or a pharmaceutically acceptable salt or hydrate thereof, where $X^2$, $X^3$, $R^3$, $R^d$ and $R^e$ are as described above, and $P^1$ is a pharmacophore.

With regard to compounds having a structure according to Formula E, F or G, $R^d$ and $R^e$ independently are a linear and saturated C6-C30 alkyl in certain embodiments. In some embodiments $R^d$ and $R^e$ independently are a C10 to C16 alkyl. In some embodiments $R^d$ and $R^e$ independently are a C10 to C15, C10 to C14, C10 to C13, C10 to C12 or C10 to C11 alkyl. Sometimes $R^d$ and $R^e$ independently are a C11 to C16 alkyl, C11 to C15, C11 to C14, C11 to C13 or C11 to C12 alkyl. Sometimes $R^d$ and $R^e$ independently are a C12 to C16, C12 to C15, C12 to C14 or C12 to C13 alkyl. Sometimes $R^d$ and $R^e$ independently are a C13 to C16, C13 to C15, C13 to C14, C14 to C16, C14 to C15 or C15 to C16 alkyl. Sometimes $R^d$ and $R^e$ independently are a C10 (e.g., a decyle group), C11 (e.g., an undecyle group), C12 (e.g., a dodecyle group), C13 (e.g., a tridecyle group), C14 (e.g., a tetradecyle group), C15 (e.g., a pentadecyle group) or C16 alkly (e.g., a hexadecyle group). Sometimes $R^d$ and $R^e$ independently are a C1-4 alkyl. Each $R^d$ and $R^e$ often is a linear alkyl group, and each $R^d$ and $R^e$ often is a saturated alkyl group. In some embodiments $R^d$ and $R^e$ are the same or different. In some embodiments, $R^d$ and $R^e$ independently include 1, 2, 3, 4 or 5 double bonds (e.g., unsaturations). In certain embodiments, $R^d$ and $R^e$ are not substituted by an epoxy moiety, and sometimes $R^d$ and $R^e$ are not substituted by a hydroxyl moiety. In specific embodiments, $R^d$ and $R^e$ are not substituted by an epoxy moiety or a hydroxyl moiety. In various embodiments, $R^d$ and $R^e$ include no double bond (e.g., no unsaturation).

With regard to compounds having a structure according to Formula E, F or G, a pharmacophore $P^1$ can by any molecule that exhibits an immunostimulatory activity. In certain embodiments, a pharmacophore $P^1$ has a structure according to Formula H:

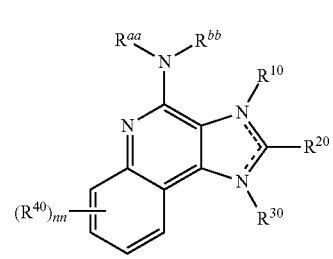

Formula H or a pharmaceutically acceptable salt thereof, where a phospholipid, or a phospholipid-like, structure is linked to the pharmacophore at any suitable linkage point, and where:

$R^{10}$, $R^{20}$, and $R^{30}$ in Formula H are each independently hydrogen; cyclic alkyl of three, four, or five carbon atoms; straight chain or branched chain alkyl containing one to about ten carbon atoms and substituted straight chain or branched chain alkyl containing one to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; fluoro- or chloroalkyl containing from one to about ten carbon atoms and one or more fluorine or chlorine atoms; straight chain or branched chain alkenyl containing two to about ten carbon atoms and substituted straight chain or branched chain alkenyl containing two to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; hydroxyalkyl of one to about six carbon atoms; alkoxyalkyl wherein the alkoxy moiety contains one to about four carbon atoms and the alkyl moiety contains one to about six carbon atoms; acyloxyalkyl wherein the acyloxy moiety is alkanoyloxy of two to about four carbon atoms or benzoyloxy, and the alkyl moiety contains one to about six carbon atoms, with the proviso that any such alkyl, substituted alkyl, alkenyl, substituted alkenyl, hydroxyalkyl, alkoxyalkyl, or acyloxyalkyl group does not have a fully carbon substituted carbon atom bonded directly to the nitrogen atom; benzyl; (phenyl)ethyl; and phenyl; said benzyl, (phenyl)ethyl or phenyl substituent being optionally substituted on the benzene ring by one or two moieties independently selected from the group consisting of alkyl of one to about four carbon atoms, alkoxy of one to about four carbon atoms, and halogen, with the proviso that when said benzene ring is substituted by two of said moieties, then the moieties together contain no more than six carbon atoms; —CHR$_x$R$_y$, wherein R$_y$ is hydrogen or a carbon-carbon bond, with the proviso that when R$_y$ is hydrogen R$_x$ is alkoxy of one to about four carbon atoms, hydroxyalkoxy of one to about four carbon atoms, 1-alkynyl of two to about ten carbon atoms, tetrahydropyranyl, alkoxyalkyl wherein the alkoxy moiety contains one to about four carbon atoms and the alkyl moiety contains one to about four carbon atoms, 2-, 3-, or 4-pyridyl, and with the further proviso that when R$_y$ is a carbon-carbon bond R$_y$ and R$_x$ together form a tetrahydrofuranyl group optionally substituted with one or more substituents independently selected from the group consisting of hydroxy or hydroxyalkyl of one to about four carbon atoms; straight chain or branched chain alkyl containing one to about eight carbon atoms, straight chain or branched chain hydroxyalkyl containing one to about six carbon atoms, morpholinomethyl, benzyl, (phenyl)ethyl and phenyl, the benzyl, (phenyl)ethyl or phenyl substituent being optionally substituted on the benzene ring by a moiety selected from the group consisting of methyl, methoxy, or halogen; or —C(R$_S$)(R$_T$)(X) wherein R$_S$ and R$_T$ are independently selected from the group consisting of hydrogen, alkyl of one to about four carbon atoms, phenyl, and substituted phenyl wherein the substituent is selected from the group consisting of alkyl of one to about four carbon atoms, alkoxy of one to about four carbon atoms, and halogen; and X is alkoxy containing one to about four carbon atoms, alkoxyalkyl wherein the alkoxy moiety contains one to about four carbon atoms and the alkyl moiety contains one to about four carbon atoms, haloalkyl of one to about four carbon atoms, alkylamido wherein the alkyl group contains one to about four carbon atoms, amino, substituted amino wherein the substituent is alkyl or hydroxyalkyl of one to about four carbon atoms, azido, alkylthio of one to about four carbon atoms, or morpholinoalkyl wherein the alkyl moiety contains one to about four carbon atoms;

R$^{40}$ in Formula H is hydrogen, C$_{1-8}$ alkyl, C$_{1-8}$ alkoxy, or halo;

nn in Formula H is 1, 2, 3, or 4;

R$^{aa}$ and R$^{bb}$ in Formula H are each independently hydrogen, (C$_1$-C$_6$)alkyl, hydroxy(C$_1$-C$_6$)alkyl, adamantyl, adamantyl(C$_1$-C$_6$)alkyl, amino(C$_1$-C$_6$)alkyl, aminosulfonyl, (C$_1$-C$_6$)alkanoyl, aryl, or benzyl; or R$^{aa}$ and R$^{bb}$ together with the nitrogen to which they are attached form a pyrrolidino, piperidino, or morpholino group; and the dashed lines in the five membered ring of Formula H denote an optional bond that connects a nitrogen of the five membered ring to the carbon that is between the two nitrogens of the five membered ring, and when the bond is present, either R$^{10}$ or R$^{30}$ is absent.

In some embodiments, one of R$^{aa}$ or R$^{bb}$ in Formula H independently is —X$^2$—X$^3$—R$^3$, or has a structure according to Formula C or Formula D, and the other R$^{aa}$ or R$^{bb}$ is hydrogen, C1-C6 alkyl or C1-C6 alkoxy.

In certain embodiments, a pharmacophore P$^1$ has a structure according to Formula I:

Formula I

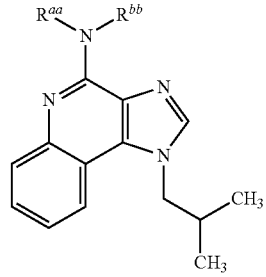

or a pharmaceutically acceptable salt thereof, where a phospholipid, or a phospholipid-like, structure is linked to the pharmacophore at any suitable linkage point, and where R$^{aa}$ and R$^{bb}$ are as defined above. In some embodiments, one of R$^{aa}$ or R$^{bb}$ in Formula I is —X$^2$—X$^3$—R$^3$, or has a structure according to Formula C or Formula D, and the other R$^{aa}$ or R$^{bb}$ is hydrogen, C1-C6 alkyl or C1-C6 alkoxy.

Also with regard to compounds having a structure according to Formula E, F or G, a pharmacophore P$^1$, in certain embodiments, has a structure according to Formula J or Formula K:

Formula J

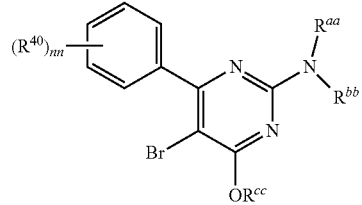

-continued

Formula K

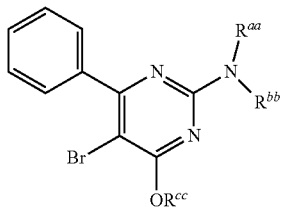

or a pharmaceutically acceptable salt thereof, where a phospholipid, or a phospholipid-like, structure is linked to the pharmacophore at any suitable linkage point, where $R^{40}$, nn, $R^{aa}$ and $R^{bb}$ are as defined above, and where $R^{cc}$ is hydrogen, C1-C6 alkyl or C1-C6 alkoxy. In some embodiments, one of $R^{aa}$ or $R^{bb}$ in Formula J or Formula K is —$X^2$—$X^3$—$R^3$, or has a structure according to Formula C or Formula D, and the other $R^{aa}$ or $R^{bb}$ is hydrogen, C1-C6 alkyl or C1-C6 alkoxy. In the latter embodiments $R^{cc}$ sometimes is hydrogen. In certain embodiments, $R^{cc}$ n Formula J or Formula K is —$X^2$—$X^3$—$R^3$, or has a structure according to Formula C or Formula D. In the latter embodiments, $R^{aa}$ or $R^{bb}$ independently are hydrogen, C1-C6 alkyl or C1-C6 alkoxy.

Pharmaceutical Compositions and Formulations

A compound described herein can be prepared as a pharmaceutically acceptable salt. As used herein, the term "pharmaceutically acceptable salt" refers to a derivative of the disclosed compounds where the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. Pharmaceutically acceptable salts include conventional non-toxic salts or quaternary ammonium salts of the parent compound formed, for example, from non-toxic inorganic or organic acids. For example, conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. In other examples, conventional non-toxic salts include those derived from bases, such as potassium hydroxide, sodium hydroxide, ammonium hydroxide, caffeine, various amines, and the like. Pharmaceutically acceptable salts can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., p. 1418 (1985), the disclosure of which is hereby incorporated by reference.

The term "pharmaceutically acceptable" as used herein refers to compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The terms "stable compound" and "stable structure" are meant to indicate a compound that is sufficiently robust to survive isolation to a useful degree of purity from a reaction mixture, and formulation into an efficacious therapeutic agent. Stable compounds are contemplated herein for use in treatment methods described.

A compound described herein can be formulated in combination with one or more other agents. The one or more other agents can include, without limitation, another compound described herein, an anti-cell proliferative agent (e.g., chemotherapeutic), an anti-inflammatory agent, and an antigen.

A compound described herein can be formulated as a pharmaceutical composition and administered to a mammalian host, such as a human patient or nonhuman animal, in a variety of forms adapted to the chosen route of administration. Non-limiting examples of routes of administration include oral, parenteral, intravenous, intramuscular, topical, instillation (e.g., bladder instillation), subcutaneous, intradermal routes. In certain embodiments, a composition is locally administered, e.g., intravesicularly. A composition sometimes includes a diluent and sometimes an adjuvant, carrier (e.g., assimilable, editable), buffer, preservative and the like. A compound can be administered also in a liposomal composition or as a microemulsion, in certain embodiments. Various sustained release systems for drugs have also been devised, and can be applied to a compound described herein. See, for example, U.S. Pat. No. 5,624,677, the methods of which are incorporated herein by reference.

For administration to the bladder of a subject, in some embodiments, a concentration of about 10 nM to about 1000 nM, or about 100 nM to about 10,000 nM, of a compound described herein may be delivered. In certain embodiments, a composition described herein is administered in conjunction with locally applied ultrasound, electromagnetic radiation or electroporation or other electrically based drug delivery technique, local chemical abrasion, or local physical abrasion. In some embodiments, a composition described herein includes, or is administered with, a surfactant (e.g., a locally applied) to enhance permeability of a compound described herein across the bladder mucosa. In certain embodiments, a composition herein provides enhanced endosomal uptake, which can result from particle size, receptor multimerization or sustained release, for example.

Compounds described herein may be enclosed in hard or soft shell gelatin capsules, may be compressed into tablets, or may be incorporated directly with the food of the patient's diet. For oral therapeutic administration, an active compound may be combined with one or more excipients and used in the form of ingestible tablets, buccal tablets, troches, capsules, elixirs, suspensions, syrups, wafers, and the like. Such compositions and preparations sometimes contain at least 0.1% of active compound. The percentage of the compositions and preparations may be varied and sometimes are about 2% to about 60% of the weight of a given unit dosage form. The amount of active compound in such therapeutically useful compositions is such that an effective dosage level will be obtained.

Tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added.

When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

An active compound may be administered by infusion or injection. Solutions of an active compound or a pharmaceutically acceptable salt thereof can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations sometimes contain a preservative to prevent the growth of microorganisms.

A pharmaceutical dosage form can include a sterile aqueous solution or dispersion or sterile powder comprising an active ingredient, which are adapted for the extemporaneous preparation of sterile solutions or dispersions, and optionally encapsulated in liposomes. The ultimate dosage form sometimes is a sterile fluid and stable under the conditions of manufacture and storage. A liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. An isotonic agent, for example, a sugar, buffer or sodium chloride is included in some embodiments. Prolonged absorption of an injectable composition can be brought about by the use in the compositions of agents delaying absorption, for example, aluminum monostearate and gelatin. Sterile solutions -often are prepared by incorporating an active compound in a required amount in an appropriate solvent, sometimes with one or more of the other ingredients enumerated above, followed by filter sterilization. In the case of sterile powders for the preparation of sterile injectable solutions, preparation methods sometimes utilized are vacuum drying and the freeze drying techniques, which yield a powder of an active ingredient in addition to any additional desired ingredient present in the previously sterile-filtered solutions.

For topical administration, a compound herein may be applied in pure form, e.g., when in liquid form. However, it is generally desirable to administer a compound as a composition or formulation, in combination with an acceptable carrier, which may be a solid or a liquid. Useful solid carriers include finely divided solids such as talc, clay, microcrystalline cellulose, silica, alumina and the like. Useful liquid carriers include water, alcohols or glycols or water-alcohol/glycol blends, or phospholipids in propylenglycol/ethylenglycol, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

The ability of a compound herein to act as a TLR agonist or TLR antagonist may be determined using pharmacological models which are known, including the procedures disclosed by Lee et al., PNAS, 100:6646 (2003).

Useful dosages of compounds can be determined by comparing their in vitro activity, and in vivo activity in animal models. Methods for the extrapolation of effective dosages in mice, and other animals, to humans are known to the art. In some embodiments, the concentration of a compound described herein in a liquid composition is about 0.1-25 wt-%, and sometimes about 0.5-10 wt-%. The concentration in a semi-solid or solid composition such as a gel or a powder sometimes is about 0.1-5 wt-%, and sometimes about 0.5-2.5 wt-%.

The amount of the compound, or an active salt or derivative thereof, required for use in treatment varies not only with a particular salt selected but also with the route of administration, the nature of the condition being treated and the age and condition of the patient and will be ultimately at the discretion of the attendant physician or clinician. In general a suitable dose sometimes is in the range of from about 0.5 to about 100 mg/kg, e.g., from about 10 to about 75 mg/kg of body weight per day, such as 3 to about 50 mg per kilogram body weight of the recipient per day, and often is in the range of 6 to 90 mg/kg/day, or about 15 to 60 mg/kg/day. A suitable dose, in general, sometimes is in the range of from about 1 to 150 mg/kg body weight of the recipient per day, e.g. from about 10 to about 130 mg/kg, from about 40 to about 120 mg/kg, from about 50 to about 100 mg/kg, from about 60 to 90 mg/kg, from about 65 to 85 mg/kg, or, for example, about 80 mg/kg/day. A compound may be conveniently administered in unit dosage form, and for example, contain 5 to 1000 mg, or 10 to 750 mg, or 50 to 500 mg of active ingredient per unit dosage form. An active ingredient can be administered to achieve peak plasma concentrations of an active compound of from about 0.01 to about 100 pM, about 0.5 to about 75 pM, about 1 to 50 pM, or about 2 to about 30 pM. Such concentrations may be achieved, for example, by the intravenous injection of a 0.05 to 5% solution of an active ingredient, optionally in saline, or orally administered as a bolus containing about 1-100 mg of an active ingredient. Desirable blood levels may be maintained by continuous infusion to provide about 0.01-5.0 mg/kg/hr or by intermittent infusions containing about 0.4-15 mg/kg of the active ingredient(s). A desired dose may conveniently be presented in a single dose or as divided doses administered at appropriate intervals, for example, as two, three, four or more sub-doses per day. A sub-dose itself may be further divided, e.g., into a number of discrete loosely spaced administrations; such as multiple inhalations from an insufflator or by application of a plurality of drops into the eye.

Treatments

Compositions provided may be useful for the treatment or prevention of certain conditions in a subject. Such conditions include, for example, proliferative conditions such as cancers, microbial infections, heart conditions and obesity conditions; inflammation conditions and autoimmune conditions in certain embodiments.

The terms "treat" and "treating" as used herein refer to (i) preventing a pathologic condition from occurring (e.g. prophylaxis); (ii) inhibiting the pathologic condition or arresting its development; (iii) relieving the pathologic condition; and/or (iv) ameliorating, alleviating, lessening, and removing symptoms of a disease or condition. A candidate molecule or compound described herein may be in a therapeutically effective amount in a formulation or medicament, which is an amount that can lead to a biological effect (e.g., inhibiting inflammation), or lead to ameliorating, alleviating, lessening, relieving, diminishing or removing symptoms of a disease or condition, for example. The terms also can refer to reducing or stopping a cell proliferation rate (e.g., slowing or halting tumor growth) or reducing the number of proliferating cancer cells (e.g., removing part or all of a tumor). A molecule described herein can be administered to a subject in need thereof to potentially treat a melanoma. In such treatments, the terms "treating," "treatment" and "therapeutic effect" can refer to reducing or stopping a cell proliferation rate (e.g., slowing or halting tumor growth), reducing the number of proliferating cancer cells (e.g., ablating part or all of a tumor) and alleviating, completely or in part, a melanoma condition.

A drug, which can be a prophylactic or therapeutic agent, can be administered to any appropriate subject having a melanoma as described herein. Non-limiting examples of a subject include mammal, human, ape, monkey, ungulate (e.g., equine, bovine, caprine, ovine, porcine, buffalo, camel and the like), canine, feline, rodent (e.g., murine, mouse, rat) and the like. A subject may be male or female, and a drug can be administered to a subject in a particular age group, including, for example, juvenile, pediatric, adolescent, adult and the like.

The term "therapeutically effective amount" as used herein refers to an amount of a compound provided herein, or an amount of a combination of compounds provided herein, to treat or prevent a disease or disorder, or to treat a symptom of the disease or disorder, in a subject. As used herein, the terms "subject" and "patient" generally refers to an individual who will receive or who has received treatment (e.g., administration of a compound described herein) according to a method described herein.

A proliferative condition sometimes is a cancer. Cancers and related disorders sometimes are of an epithelial cell origin. In some embodiments, a proliferative condition is associated with blood, such as leukemia. Non-limiting examples of leukemias and other blood conditions include acute leukemia, acute lymphocytic leukemia, acute myelocytic leukemia (e.g., myeloblastic, promyelocytic, myelomonocytic, monocytic, and erythroleukemia leukemias) and myelodysplastic syndrome; chronic leukemias, such as but not limited to, chronic myelocytic (granulocytic) leukemia, chronic lymphocytic leukemia, hairy cell leukemia; and polycythemia vera.

In certain embodiments, a proliferative condition presents as a lymphoma. Non-limiting examples of lymphomas include Hodgkin's disease and non-Hodgkin's disease. A proliferative condition sometimes is a multiple myeloma, non-limiting examples of which include smoldering multiple myeloma, nonsecretory myeloma, osteosclerotic myeloma, plasma cell leukemia, solitary plasmacytoma and extramedullary plasmacytoma. A proliferative condition in some embodiments presents as Waldenstrom's macroglobulinemia; monoclonal gammopathy of undetermined significance; benign monoclonal gammopathy; or heavy chain disease.

A proliferative condition in some embodiments presents as a sarcoma (e.g., in bone or connective tissue). Non-limiting examples of sarcomas include bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma.

In some embodiments, a proliferative condition presents as a condition of the brain (e.g., brain tumor). Non-limiting examples of proliferative conditions of the brain include glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma.

A proliferative condition in some embodiments is a breast cancer. Non-limiting breast cancers include ductal carcinoma, adenocarcinoma, lobular (small cell) carcinoma, intraductal carcinoma, medullary breast cancer, mucinous breast cancer, tubular breast cancer, papillary breast cancer, Paget's disease, and inflammatory breast cancer. In certain embodiments, a proliferative condition presents as an adrenal cancer. Non-limiting examples of adrenal cancer include pheochromocytom and adrenocortical carcinoma. A proliferative condition sometimes presents as a thyroid cancer, including, but not limited to papillary or follicular thyroid cancer, medullary thyroid cancer and anaplastic thyroid cancer.

In certain embodiments, a proliferative condition presents as a pancreatic cancer, including, but not limited to, insulinoma, gastrinoma, glucagonoma, vipoma, somatostatin-secreting tumor, and carcinoid or islet cell tumor. A proliferative condition in some embodiments presents as a pituitary cancer, non-limiting examples of which include Cushing's disease, prolactin-secreting tumor, acromegaly, and diabetes insipius. In some embodiments, a proliferative condition presents as an eye cancer, including but not limited to, ocular melanoma such as iris melanoma, choroidal melanoma, and cilliary body melanoma, and retinoblastoma.

A proliferative condition in certain embodiments presents as a vaginal cancer or vulvar cancer, which can include without limitation squamous cell carcinoma, adenocarcinoma, melanoma, squamous cell carcinoma, melanoma, adenocarcinoma, basal cell carcinoma, sarcoma, and Paget's disease. In some embodiments, a proliferative condition presents as a cervical cancers, which can include, but is not limited to, squamous cell carcinoma and adenocarcinoma. Uterine cancers also are a form of certain proliferative conditions, including, but not limited to, endometrial carcinoma and uterine sarcoma. A proliferative condition sometimes is an ovarian cancer, non-limiting examples of which include ovarian epithelial carcinoma, borderline tumor, germ cell tumor, and stromal tumor.

In some embodiments, a proliferative condition is an esophageal cancer, non-limiting examples of which include squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma. A proliferative condition sometimes presents as a stomach cancer, including, but not limited to, adenocarcinoma, fungating (polypoid), ulcerating, superficial spreading, diffusely spreading, malignant lymphoma, liposarcoma, fibrosarcoma, and carcinosarcoma. A proliferative condition sometimes presents as colon cancer or a rectal cancers. In some embodiments, a proliferative condition is a liver cancer, non-limiting examples of which include hepatocellular carcinoma and hepatoblastoma.

A proliferative condition in certain embodiments presents as a gallbladder cancer, including, but not limited to, adenocarcinoma. In certain embodiments, a proliferative condition presents as bile duct cancer, such as cholangiocarcinomas (e.g., papillary, nodular, and diffuse) for example.

A proliferative condition in some embodiments is a lung cancer. Non-limiting examples of lung cancers include non-small cell lung cancer, squamous cell carcinoma (epidermoid carcinoma), adenocarcinoma, large-cell carcinoma and small-cell lung cancer. In certain embodiments, a proliferative condition presents as a testicular cancer, such as a germinal tumor, seminoma, anaplastic, classic (typical), spermatocytic, nonseminoma, embryonal carcinoma, teratoma carcinoma or choriocarcinoma (yolk-sac tumor). A proliferative condition in some embodiments is a prostate cancer, including, but not limited to, prostatic intraepithelial neoplasia, adenocarcinoma, leiomyosarcoma, and rhabdomyosarcoma. In certain embodiments, a proliferative condition is a penal cancer.

A proliferative condition sometimes is an oral cancer, non-limiting examples of which include squamous cell carcinoma; basal cancers; salivary gland cancers such as but not limited to adenocarcinoma, mucoepidermoid carcinoma, and adenoidcystic carcinoma. In some embodiments, a proliferative condition is a pharynx cancers, including, but not limited to squamous cell cancer and verrucous. A proliferative condition sometimes presents as a skin cancer, non-limiting examples of which include basal cell carcinoma, squamous cell carcinoma, melanoma, superficial spreading melanoma, nodular melanoma, lentigo malignant melanoma, and acral lentiginous melanoma.

In some embodiments, a proliferative condition is a kidney cancer such as a renal cell carcinoma, adenocarcinoma, hypemephroma, fibrosarcoma, transitional cell cancer (renal pelvis and/or uterer), and Wilms' tumor. In certain embodiments, a proliferative condition is a bladder cancer, non-limiting examples of which include superficial bladder cancer, transitional cell carcinoma, squamous cell cancer, adenocarcinoma and carcinosarcoma.

In certain embodiments, a proliferative condition is a cancer selected from myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas; carcinoma, including that of the bladder, breast, colon, kidney, liver, lung, ovary, pancreas, stomach, cervix, thyroid and skin (e.g., squamous cell carcinoma); hematopoietic tumors of lymphoid lineage, including leukemia, acute lymphocytic leukemia, acute lymphoblastic leukemia, B-cell lymphoma, T-cell lymphoma, Burkitt's lymphoma; hematopoictic tumors of myeloid lineage, including acute and chronic myelogenous leukemias and promyclocytic leukemia; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xeroderma pigmentosum, keratoactanthoma, seminoma, thyroid follicular cancer and teratocarcinoma. It is also contemplated that cancers caused by aberrations in apoptosis can be addressed by compositions described herein. Such cancers may include but not be limited to follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, may be treated or prevented in the skin, lung, colon, breast, prostate, bladder, kidney, pancreas, ovary, or uterus.

Cell proliferative conditions also include viral diseases, including for example, acquired immunodeficiency syndrome, adenoviridae infections, alphavirus Infections, arbovirus Infections, Borna disease, bunyaviridae Infections, caliciviridae Infections, chickenpox, Coronaviridae Infections, coxsackievirus Infections, cytomegalovirus Infections, dengue, DNA Virus Infections, eethyma, contagious, encephalitis, arbovirus, Epstein-Barr virus infections, erythema infectiosum, hantavirus infections, hemorrhagic fevers, viral, hepatitis, viral, human, herpes simplex, herpes zoster, herpes zoster oticus, herpesviridae infections, infectious mononucleosis, influenza, e.g., in birds or humans, Lassa fever, measles, Molluscum contagiosum, mumps, oaramyxoviridae Infections, phlebotomus fever, polyomavirus infections, rabies, respiratory syncytial virus Infections, Rift Valley fever, RNA Virus Infections, rubella, slow virus diseases, smallpox, subacute sclerosing panencephalitis, tumor virus infections, warts, West Nile fever, virus diseases and Yellow Fever. For example, Large T antigen of the SV40 transforming virus acts on UBF, activates it and recruits other viral proteins to Pol I complex, and thereby stimulates cell proliferation to ensure virus propagation. Cell proliferative conditions also include conditions related to angiogenesis (e.g., cancers) and obesity caused by proliferation of adipocytes and other fat cells.

Cell proliferative conditions include microbial infections. Non-limiting examples of microbes include viruses, bacteria, yeast and fungus. Examples of certain microbes that may be treated by a composition described are listed herein.

Cell proliferative conditions also include cardiac conditions resulting from cardiac stress, such as hypertension, balloon angioplasty, valvular disease and myocardial infarction. For example, cardiomyocytes are differentiated muscle cells in the heart that constitute the bulk of the ventricle wall, and vascular smooth muscle cells line blood vessels. Although both are muscle cell types, cardiomyocytes and vascular smooth muscle cells vary in their mechanisms of contraction, growth and differentiation. Cardiomyocytes become terminally differentiated shortly after heart formation and thus loose the capacity to divide, whereas vascular smooth muscle cells are continually undergoing modulation from the contractile to proliferative phenotype. Under various pathophysiological stresses such as hypertension, balloon angioplasty, valvular disease and myocardial infarction, for example, the heart and vessels undergo morphologic growth-related alterations that can reduce cardiac function and eventually manifest in heart failure. Thus, provided herein are methods for treating cardiac cell proliferative conditions by administering a compound described herein in an effective amount to treat the cardiac condition. A compound may be administered before or after a cardiac stress has occurred or has been detected, and the compound or nucleic acid may be administered after occurrence or detection of hypertension, balloon angioplasty, valvular disease or myocardial infarction, for example. Administration of such a compound may decrease proliferation of vascular muscle cells and/or smooth muscle cells.

A cell proliferation condition also may pertain to obesity. In some embodiments, a cell proliferative condition is abnormal proliferation of adipocytes.

A compound described herein can be administered to a subject in need thereof to induce an immune response in the subject. The immune response may be generated automatically by the subject against a foreign antigen (e.g., pathogen infection) in certain embodiments. In some embodiments, an antigen is co-administered with a compound described herein, where an immune response is mounted in the subject against the antigen. An antigen may be specific for a particular cell proliferative condition (e.g., specific cancer antigen) or particular pathogen (e.g., gram positive bacteria wall antigen; *S. aureus* antigen), in certain embodiments. An immunostimulatory composition may be administered in a vaccine or combination vaccine, in some embodiments. An immunostimulatory composition may be administered as an adjuvant composition in certain embodiments, and may be administered in conjunction with an antigen (e.g., sequential administration or co-administration with antigen) in certain embodiments.

A compound described herein can be administered to a subject in need thereof to potentially prevent, inhibit or treat one or more inflammation disorders. As used hereinafter, the terms "treating," "treatment" and "therapeutic effect" can refer to reducing, inhibiting or stopping (preventing) an inflammation response (e.g., slowing or halting antibody production or amount of antibodies to a specific antigen), reducing the amount of inflamed tissue and alleviating, completely or in part, an inflammation condition. Inflammation disorders include, without limitation, allergy, asthma, autoimmune disorder, chronic inflammation, chronic prostatitis, glomerulonephritis, hypersensitivities, inflammatory bowel diseases, myopathy (e.g., in combination with systemic sclerosis, dermatomyositis, polymyositis, and/or inclusion body myositis), pelvic inflammatory disease, reperfusion injury, rheumatoid arthritis, transplant rejection, vasculitis, and leukocyte disorders (e.g., Chediak-Higashi syndrome, chronic granulomatous disease). Certain autoimmune disorders also are inflammation disorders (e.g., rheumatoid arthritis). In some embodiments, the inflammation disorder is selected from the group consisting of chronic inflammation, chronic prostatitis, glomerulonephritis, a hypersensitivity, myopathy, pelvic inflammatory disease, reperfusion injury, transplant rejection, vasculitis, and leukocyte disorder. In certain embodiments, an inflammation condition includes, but is not limited to, bronchiectasis, bronchiolitis, cystic fibrosis, acute lung injury, acute respiratory distress syndrome (ARDS), atherosclerosis, and septic shock (e.g., septicemia with multiple organ failure). In some embodiments, an inflammation disorder is not a condition selected from the group consisting of allergy, asthma, ARDS and autoimmune disorder. In certain embodiments, an inflammation disorder is not a condition selected from the group consisting of gastrointestinal tract inflammation, brain inflammation, skin inflammation and joint inflammation. In certain embodiments, the inflammation disorder is a neutrophil-mediated disorder. In some embodiments, an inflammatory condition also is a cell proliferation condition, such as, for example, inflammation conditions of the skin (e.g., eczema), discoid lupus erythematosus, lichen planus, lichen sclerosus, mycosis fungoides, photodermatoses, pityriasis rosea and psoriasis.

A compound described herein can be administered to a subject in need thereof to potentially treat one or more autoimmune disorders. In such treatments, the terms "treating," "treatment" and "therapeutic effect" can refer to reducing, inhibiting or stopping an autoimmune response (e.g., slowing or halting antibody production or amount of antibodies to a specific antigen), reducing the amount of inflamed tissue and alleviating, completely or in part, an autoimmune condition. Autoimmune disorders, include, without limitation, autoimmune encephalomyelitis, colitis, autoimmune insulin dependent diabetes mellitus (IDDM), and Wegener granulomatosis and Takayasu arteritis. Models for testing compounds for such diseases include, without limitation, (a) (i) C5BL/6 induced by myelin oligodendrocyte glycoprotein (MOG) peptide, (ii) SJL mice PLP139-151, or 178-191 EAE, and (iii) adoptive transfer model of EAE induced by MOG or PLP peptides for autoimmune encephalomyelitis; (b) non-obese diabetes (NOD) mice for autoimmune IDDM; (c) dextran sulfate sodium (DSS)-induced colitis model and trinitrobenzene sulfonic acid (TNBS)-induced colitis model for colitis; and (d) systemic small vasculitis disorder as a model for Wegener granulomatosis and Takayasu arteritis. A compound described herein may be administered to a subject to potentially treat one or more of the following disorders: Acute disseminated encephalomyelitis (ADEM); Addison's disease; alopecia greata; ankylosing spondylitis; antiphospholipid antibody syndrome (APS); autoimmune hemolytic anemia; autoimmune hepatitis; autoimmune inner ear disease; bullous pemphigoid; celiac disease; Chagas disease; chronic obstructive pulmonary disease; Crohns disease (one of two types of idiopathic inflammatory bowel disease "IBD"); dermatomyositis; diabetes mellitus type 1; endometriosis; Goodpasture's syndrome; Graves' disease; Guillain-Barré syndrome (GBS); Hashimoto's disease; hidradenitis suppurativa; idiopathic thrombocytopenic purpura; interstitial cystitis; lupus erythematosus; mixed connective tissue disease; morphea; multiple sclerosis (MS); myasthenia gravis; narcolepsy; neuromyotonia; pemphigus vulgaris; pernicious anaemia; polymyositis; primary biliary cirrhosis; rheumatoid arthritis; schizophrenia; scleroderma; Sjögren's syndrome; temporal arteritis (also known as "giant cell arteritis"); ulcerative colitis (one of two types of idiopathic inflammatory bowel disease "IBD"); vasculitis; vitiligo; and Wegener's granulomatosis. In some embodiments, the autoimmune disorder is not a condition selected from the group consisting of Crohns disease (or Crohn's disease), rheumatoid arthritis, lupus and multiple sclerosis.

In some embodiments, a compound described herein is utilized in combination with administration of one or more other therapies that include, but are not limited to, chemotherapies, radiation therapies, hormonal therapies, and/or biological therapies (e.g. immunotherapies). An agent that can be used in combination with a compound described herein can include, but is not limited to, a proteinaceous molecule, including, but not limited to, peptide, polypeptide, protein, including post-translationally modified protein, antibody and the like; small molecule (less than 1000 daltons); inorganic or organic compounds; nucleic acid molecule, including, but not limited to, double-stranded or single-stranded DNA, or double-stranded or single-stranded RNA, and triple helix nucleic acid molecules. An agent used in combination with a compound described herein can be derived from any known organism (including, but not limited to, animals, plants, bacteria, fungi, and protista, or viruses) or from a library of synthetic molecules. An agent that may be utilized in combination with a compound described herein includes a protein kinase inhibitor (e.g., a receptor protein kinase inhibitor) and an angiogenesis inhibitor.

Immunostimulatory Compositions

Compounds described herein may have immunostimulatory activity, and can enhance the level of an immune response against an antigen. Accordingly, a compound described herein may be useful as an adjuvant that can be administered in conjunction with an antigen. Accordingly, a compound described herein can be incorporated as part of a vaccine composition that contains an antigen in some embodiments, and can be administered separately from an antigen in an adjuvant composition in certain embodiments.

Vaccine compositions and adjuvant compositions are referred to collectively herein as "immunostimulatory compositions."

Immunostimulatory Composition Components

A compound described herein can be utilized in an immunostimulatory composition in any effective amount. In certain embodiments, a compound described herein can be used in an amount of about 1 micrograms to about 100,000 micrograms per dose. A compound described herein also can be used in an amount of about 1 micrograms to about 50,000 micrograms per dose, about 1 micrograms to about 25,000 micrograms per dose, about 1 micrograms to about 5,000 micrograms per dose, about 1 micrograms to about 4,000 micrograms per dose, about 1 micrograms to about 3,000 micrograms per dose, about 1 micrograms to about 2,000 micrograms per dose, and about 1 micrograms to about 1,000 micrograms per dose. A compound described herein also may be used in an amount of about 5 micrograms to about 750 micrograms per dose, about 5 micrograms to about 500 micrograms per dose, about 5 micrograms to about 200 micrograms per dose, about 5 micrograms to about 100 micrograms per dose, about 15 micrograms to about 100 micrograms per dose, and in an amount of about 30 micrograms to about 75 micrograms per dose, in some embodiments.

In addition to a compound described herein, an immunostimulatory composition can include one or more other components. For example, a triterpenoid can be included in an immunostimulatory composition. Triterpenoids suitable for use in an immunostimulatory composition can come from many sources (e.g., plant derived or synthetic equivalents), including but not limited to, *Quillaja saponaria*, tomatine, ginseng extracts, mushrooms, and an alkaloid glycoside structurally similar to steroidal saponins. Thus, triterpenoids suitable for use in an immunostimulatory composition include saponins, squalene, and lanosterol. The amount of a triterpenoid suitable for use in an immunostimulatory composition depends upon the nature of the triterpenoid used. However, they are generally used in an amount of about 1 micrograms to about 5,000 micrograms per dose. They also can be used in an amount of about 1 micrograms to about 4,000 micrograms per dose, about 1 micrograms to about 3,000 micrograms per dose, about 1 micrograms to about 2,000 micrograms per dose, and about 1 micrograms to about 1,000 micrograms per dose. They also may be used in an amount of about 5 micrograms to about 750 micrograms per dose, about 5 micrograms to about 500 micrograms per dose, about 5 micrograms to about 200 micrograms per dose, about 5 micrograms to about 100 micrograms per dose, about 15 micrograms to about 100 micrograms per dose, and in an amount of about 30 micrograms to about 75 micrograms per dose.

If a saponin is used, an immunostimulatory composition often contains an immunologically active saponin fraction from the bark of *Quillaja saponaria*. The saponin may be, for example, Quil A or another purified or partially purified saponin preparation, which can be obtained commercially. Thus, saponin extracts can be used as mixtures or purified individual components such as QS-7, QS-17, QS-18, and QS-21. In some embodiments the Quil A is at least 85% pure. In other embodiments, the Quil A is at least 90%, 91%, 92%, 93%, 94%, 95%, 96%, 97%, 98%, or 99% pure.

CpG oligodeoxynucleic acids are characterized by the presence of an unmethylated CG dinucleotide in specific base-sequence contexts (CpG motif), and can confer immunostimulatory properties. These immunostimulatory properties include induction of a Th1-type response with prominent release of IFN-, IL-12, and IL-18. CpG ODNs (18-24 bp in length). A carrier such as QCDC, QCDCR and other combinations can facilitate uptake of CpG oligodeoxynucleic acids. The amount of CpG for use in an immunostimulatory composition depends upon the nature of the CpG used and the intended species. However, they often are used in an amount of about 1 micrograms to about 20 mg per dose. They also can be used in an amount of about 1 micrograms to about 10 mg per dose, about 1 micrograms to about 5 mg per dose, about 1 micrograms to about 4 mg per dose, about 1 micrograms to about 3 mg per dose, about 1 micrograms to about 2 mg per dose, and about 1 micrograms to about 1 mg per dose. They are can be used in an amount of about 5 micrograms to about 750 micrograms per dose, about 5 micrograms to about 500 micrograms per dose, about 5 micrograms to about 200 micrograms per dose, about 5 micrograms to about 100 micrograms per dose, 10 micrograms to about 100 micrograms per dose, about 15 micrograms to about 100 micrograms per dose, and in an amount of about 30 micrograms to about 75 micrograms per dose.

Sterols also can be used in an immunostimulatory composition, and sterols suitable for use include beta-sitosterol, stigmasterol, ergosterol, ergocalciferol, and cholesterol. These sterols are known in the art and can be purchased commercially. The amount of sterols suitable for use in an immunostimulatory composition depends upon the nature of the sterol used. However, they are often used in an amount of about 1 micrograms to about 5,000 micrograms per dose. They also can be used in an amount of about 1 micrograms to about 4,000 micrograms per dose, about 1 micrograms to about 3,000 micrograms per dose, about 1 micrograms to about 2,000 micrograms per dose, and about 1 micrograms to about 1,000 micrograms per dose. They also can be used in an amount of about 5 micrograms to about 750 micrograms per dose, about 5 micrograms to about 500 micrograms per dose, about 5 micrograms to about 200 micrograms per dose, about 5 micrograms to about 100 micrograms per dose, about 15 micrograms to about 100 micrograms per dose, and about 30 micrograms to about 75 micrograms per dose.

An immunostimulatory composition can further include one or more immunomodulatory agents, non-limiting examples of which include quaternary ammonium compounds (e.g., DDA), and interleukins, interferons, or other cytokines. These materials can be purchased commercially. The amount of an immunomodulator suitable for use in an immunostimulatory composition depends upon the nature of the immunomodulator used and the subject. However, they often are used in an amount of about 1 micrograms to about 5,000 micrograms per dose. They also can be used in an amount of about 1 micrograms to about 4,000 micrograms per dose, about 1 micrograms to about 3,000 micrograms per dose, about 1 micrograms to about 2,000 micrograms per dose, and about 1 micrograms to about 1,000 micrograms per dose. They also can be used in an amount of about 5 micrograms to about 750 micrograms per dose, about 5 micrograms to about 500 micrograms per dose, about 5 micrograms to about 200 micrograms per dose, about 5 micrograms to about 100 micrograms per dose, about 15 micrograms to about 100 micrograms per dose, and in an amount of about 30 micrograms to about 75 micrograms per dose. In a specific example, an immunostimulatory composition containing DDA can be prepared by simply mixing an antigen solution with a freshly prepared solution of DDA.

An immunostimulatory composition can further include one or more polymers, non-limiting examples of which include DEAE Dextran, polyethylene glycol, and polyacrylic acid and polymethacrylic acid (eg, CARBOPOL®). The amount of polymer suitable for use in an immunostimulatory composition depends upon the nature of the polymers used.

However, they often are used in an amount of about 0.0001% volume to volume (v/v) to about 75% v/v. In some embodiments, they are used in an amount of about 0.001% v/v to about 50% v/v, of about 0.005% v/v to about 25% v/v, of about 0.01% v/v to about 10% v/v, of about 0.05% v/v to about 2% v/v, and of about 0.1% v/v to about 0.75% v/v. In certain embodiments, they are used in an amount of about 0.02 v/v to about 0.4% v/v. DEAE-dextran can have a molecular size in the range of 50,000 Da to 5,000,000 Da, or it can be in the range of 500,000 Da to 2,000,000 Da. Such material may be purchased commercially or prepared from dextran.

In some embodiments, a polymer utilized is polyacrylic acid (e.g., the CARBOPOL® polymers), which has an average equivalent weight of 76. Polyacrylic acids often are produced from primary polymer particles of about 0.2 to 6.0 microns in average diameter. The CARBOPOL® polymers swell in water up to 1000 times their original volume and ten times their original diameter to form a gel when exposed to a pH environment greater than the pKa of the carboxylate group. At a pH greater than the pKa of carboxylate group, the carboxylate groups ionize resulting in repulsion between the negative charges, which adds to the swelling of the polymer.

An immunostimulatory composition can further include one or more Th2 stimulants such as, for example, Bay R1005® and aluminum. The amount of Th2 stimulants suitable for use in an immunostimulatory composition depends upon the nature of the Th2 stimulant used. However, a Th2 stimulant often is used in an amount of about 0.01 mg to about 10 mg per dose. In some embodiments, such stimulants are used in an amount of about 0.05 mg to about 7.5 mg per dose, of about 0.1 mg to about 5 mg per dose, of about 0.5 mg to about 2.5 mg per dose, and of 1 mg to about 2 mg per dose. A specific example is Bay R1005®, a glycolipid with the chemical name "N-(2-deoxy-2-L-leucylamino-.beta.-D-glucopyranosyl)-N-octadecyldodecanam-ide acetate." It can be synthesized according to the procedure known in the art. It often is stored at 2-8 degrees Celsius in an airtight container. Its chemical or physical properties are that it is slightly hygroscopic, does not form polymorphs, is chemically stable in air and light at temperatures up to 50 degrees Celsius and in aqueous solvents at pH 2-12 at ambient temperature. It is an amphiphilic molecule which forms micelles in aqueous solution.

Antigens

An immunostimulatory composition can contain one or more antigens. The antigen can be any of a wide variety of substances capable of producing a desired immune response in a subject. Although Quil A alone is virucidal, Quil A is detoxified with the addition of cholesterol when forming helical micelles. An immunostimulatory composition can be non-viricidal, and non-hemolytic or membranolytic. Thus, an antigens used with a immunostimulatory composition can be one or more of viruses (inactivated, attenuated, and modified live), bacteria, parasites, nucleotides, polynucleotides, peptides, polypeptides, recombinant proteins, synthetic peptides, protein extract, cells (including tumor cells), tissues, polysaccharides, carbohydrates, fatty acids, teichioc acid, peptidoglycans, lipids, or glycolipids, individually or in any combination thereof. An antigen also can include immunogenic fragments of nucleotides, polynucleotides, peptides, polypeptides, that can be isolated from the organisms referred to herein. An antigen in some embodiments is a cancer-specific molecule, such as a protein, peptide, lipid, nucleic acid, carbohydrate and the like.

Live, modified-live, and attenuated viral strains that do not cause disease in a subject can be isolated in non-virulent form or can be attenuated using methods known in the art, including serial passage in a suitable cell line or exposure to ultraviolet light or a chemical mutagen. Inactivated or killed viral strains are those that have been inactivated by methods known in the art, including treatment with formalin, betapropriolactone (BPL), binary ethyleneimine (BEI), sterilizing radiation, heat, and the like.

Two or more antigens can be combined to produce a polyvalent composition that can protect a subject against a wide variety of diseases caused by pathogens. Antigens can be combined in a single composition comprising a compound described herein, in some embodiments. In certain embodiments, a composition comprising multiple antigens is administered in conjunction with a separate adjuvant composition comprising a compound described herein (e.g., concurrently or sequentially).

An immunostimulatory composition can include a microbe as an antigen (e.g., inactivated or attenuated bacteria, virus) or microbe component. Non-limiting examples of bacteria that can be selected include *Aceinetobacter calcoaceticus, Acetobacter paseruianus, Actinobacillus pleuropneumoniae, Aeromonas hydrophila, Alicyclobacillus acidocaldarius, Arhaeglobus fulgidus, Bacillus anthracis, Bacillus pumilus, Bacillus stearothermophillus, Bacillus subtilis, Bacillus thermocatenulatus, Bordetella bronchiseptica, Burkholderia cepacia, Burkholderia glumae, Campylobacter coli, Campylobacter fetus, Campylobacter jejuni, Campylobacter hyointestinalis, Chlamydia psittaci, Chlamydia trachomatis, Chlamydophila* spp., *Chromobacterium viscosum, Erysipelothrix rhusiopathieae, Listeria monocytogenes, Ehrlichia canis, Escherichia coli, Haemophilus influenzae, Haemophilus somnus, Helicobacter suis, Lawsonia intracellularis, Legionella pneumophilia, Moraxellsa* sp., *Mycobactrium bovis, Mycoplasma hyopneumoniae, Mycoplasma mycoides* subsp. *mycoides* LC, *Clostridium perfringens, Odoribacter denticanis, Pasteurella (Mannheimia) haemolytica, Pasteurella multocida, Photorhabdus luminescens, Porphyromonas gu/ae, Porphyromonas gingivalis, Porphyromonas salivosa, Propionibacterium acnes, Proteus vulgaris, Pseudomonas wisconsinensis, Pseudomonas aeruginosa, Pseudomonas fluorescens* C9, *Pseudomonas fluorescens* SIKW1, *Pseudomonas fragi, Pseudomonas luteola, Pseudomonas oleovorans, Pseudomonas* sp B11-1, *Alcaliges eutrophus, Psychrobacter immobilis, Rickettsia prowazekii, Rickettsia rickettsiag, Salmonella typhimurium, Salmonella bongori, Salmonella enterica, Salmonella dublin, Salmonella typhimurium, Salmonella choleraseuis, Salmonella newport, Serratia marcescens, Spirlina platensis, Staphlyoccocus aureus, Staphyloccocus epidermidis, Staphylococcus hyicus, Streptomyces albus, Streptomyces cinnamoneus, Streptococcus suis, Streptomyces exfoliates, Streptomyces scabies, Sulfolobus acidocaldarius, Syechocystis* sp., *Vibrio cholerae, Borrelia burgdorferi, Treponema denticola, Treponema minutum, Treponema phagedenis, Treponema refringens, Treponema vincentii, Treponema palladium,* and *Leptospira* species, such as the known pathogens *Leptospira canicola, Leptospira grippotyposa, Leptospira hardjo, Leptospira borgpetersenii hardjo-bovis, Leptospira borgpetersenii hardjo-prajitno, Leptospira interrogans, Leptospira icterohaemorrhagiae, Leptospira pomona,* and *Leptospira bratislava,* and combinations thereof.

An inactivated virus, attenuated live virus, and/or portion of a virus may be used in an immunostimulatory composition. Some examples of viruses which can be used for antigen production include, but are not limited to, Avian herpesviruses, Bovine herpesviruses, Canine herpesviruses, Equine herpesviruses, Feline viral rhinotracheitis virus, Marek's disease virus, Ovine herpesviruses, Porcine herpesviruses, Pseudorabies virus, Avian paramyxoviruses, Bovine respiratory syncytial virus, Canine distemper virus, Canine parainfluenza virus, canine adenovirus, canine parvovirus, Bovine Parainfluenza virus 3, Ovine parainfluenza 3, Rinderpest virus, Border disease virus, Bovine viral diarrhea virus (BVDV), BVDV Type I, BVDV Type II, Classical swine fever virus, Avian Leukosis virus, Bovine immunodeficiency virus, Bovine leukemia virus, Bovine tuberculosis, Equine infectious anemia virus, Feline immunodeficiency virus, Feline leukemia virus (FeLV), Newcastle Disease virus, Ovine progressive pneumonia virus, Ovine pulmonary adenocarcinoma virus, Canine coronavirus (CCV), pantropic CCV, Canine respiratory coronavirus, Bovine coronavirus, Feline Calicivirus, Feline enteric coronavirus, Feline infectious peritonitis, virus, Porcine epidemic diarrhea virus, Porcine hemagglutinating encephalomyletitis virus, Porcine parvovirus, Porcine Circovirus (PCV) Type I, PCV Type II, Porcine Reproductive and Respiratory Syndrome (PRRS) Virus, Transmissible gastroenteritis virus, Turkey coronavirus, Bovine ephemeral fever virus, Rabies, Rotovirus, Vesicular stomatitis virus, lentivirus, Avian influenza, Rhinoviruses, Equine influenza virus, Swine influenza virus, Canine influenza virus, Feline influenza virus, Human influenza virus, Eastern Equine encephalitis virus (EEE), Venezuelan equine encephalitis virus, West Nile virus, Western equine encephalitis virus, human immunodeficiency virus, human papilloma virus, varicella zoster virus, hepatitis B virus, rhinovirus, and measles virus, and combinations thereof.

Non-limiting examples of peptide antigens include *Bordetella bronchiseptica* p68, GnRH, IgE peptides, Fel d1, and cancer antigens, and combinations thereof. Examples of other antigens include nucleotides, carbohydrates, lipids, glycolipids, peptides, fatty acids, and teichioc acid, and peptidoglycans, and combinations thereof.

Non-limiting examples of parasites that can be used for preparation of antigens with an immunostimulatory composition include *Anaplasma, Fasciola hepatica* (liver fluke), *Coccidia, Eimeria* spp., *Neospora caninum, Toxoplasma gondii, Giardia, Dirofilaria* (heartworms), *Ancylostoma* (hookworms), *Trypanosoma* spp., *Leishmania* spp., *Trichomonas* spp., *Cryptosporidium parvum, Babesia, Schistosoma, Taenia, Strongyloides, Ascaris, Trichinella, Sarcocystis, Hammondia*, and *Isopsora*, and combinations thereof. Also contemplated are external parasites including, but not limited to, ticks, including *Ixodes, Rhipicephalus, Dermacentor, Amblyomma, Boophilus, Hyalomma*, and *Haemaphysalis* species, and combinations thereof.

The amount of antigen used to induce an immune response can vary considerably depending on the antigen used, the subject, and the level of response desired, and can be determined as known in the art. For vaccines containing modified live viruses or attenuated viruses, a therapeutically effective amount of the antigen sometimes ranges from about $10^2$ Tissue Culture Infective Dose (TCID)$_{50}$ to about $10^{10}$ TCID$_{50}$, inclusive. For many such viruses, a therapeutically effective dose is sometimes in the range of about $10^2$ TCID$_{50}$ to about $10^8$ TCID$_{50}$, inclusive. In some embodiments, the ranges of therapeutically effective doses are about $10^3$ TCID$_{50}$ to about $10^6$ TCID$_{50}$, inclusive. In certain embodiments, the ranges of therapeutically effective doses are about $10^4$ TCID$_{50}$ to about $10^5$ TCID$_{50}$, inclusive.

For vaccines containing inactivated viruses, a therapeutically effective amount of the antigen sometimes is at least about 100 relative units per dose, and often in the range from about 1,000 to about 4,500 relative units per dose, inclusive. In some embodiments, a therapeutically effective amount of the antigen is in a range from about 250 to about 4,000 relative units per dose, inclusive, from about 500 to about 3,000 relative units per dose, inclusive, from about 750 to about 2,000 relative units per dose, inclusive, or from about 1,000 to about 1,500 relative units per dose, inclusive.

A therapeutically effective amount of antigen in vaccines containing inactivated viruses also can be measured in terms of Relative Potency (RP) per mL. A therapeutically effective amount often is in the range from about 0.1 to about 50 RP per mL, inclusive. In some embodiments, a therapeutically effective amount of the antigen is in a range from about 0.5 to about 30 RP per mL, inclusive, from about 1 to about 25 RP per mL, inclusive, from about 2 to about 20 RP per mL, inclusive, from about 3 to about 15 RP per mL, inclusive, or from about 5 to about 10 RP per mL, inclusive.

The number of cells for certain bacterial antigens administered in a vaccine ranges from about $1 \times 10^6$ to about $5 \times 10^{10}$ colony forming units (CFU) per dose, inclusive, in certain embodiments. In some embodiments, the number of cells ranges from about $1 \times 10^7$ to $5 \times 10^{10}$ CFU/dose, inclusive, or from about $1 \times 10^8$ to $5 \times 10^{10}$ CFU/dose, inclusive. In various embodiments, the number of cells ranges from about $1 \times 10^2$ to $5 \times 10^{10}$ CFU/dose, inclusive, or from about $1 \times 10^4$ to $5 \times 10^9$ CFU/dose, inclusive, or from about $1 \times 10^5$ to $5 \times 10^9$ CFU/dose, inclusive, or from about $1 \times 10^6$ to $5 \times 10^9$ CFU/dose, inclusive, or from about $1 \times 10^6$ to $5 \times 10^8$ CFU/dose, inclusive, or from about $1 \times 10^7$ to $5 \times 10^9$ CFU/dose, inclusive.

The number of cells for certain parasite antigens administered in a vaccine ranges from about $1 \times 10^2$ to about $1 \times 10^{10}$ per dose, inclusive, in certain embodiments. In some embodiments, the number of cells ranges from about $1 \times 10^3$ to about $1 \times 10^9$ per dose, inclusive, or from about $1 \times 10^4$ to about $1 \times 10^8$ per dose, inclusive, or from about $1 \times 10^5$ to about $1 \times 10^7$ per dose, inclusive, or from about $1 \times 10^6$ to about $1 \times 10^8$ per dose, inclusive.

Excipients

Aqueous immunostimulatory compositions can provide certain advantages. They are readily formulated and administered, and can induce few or less serious injection site reactions. However, aqueous immunostimulatory compositions with an antigen tend to diffuse from the injection site, are cleared by the subject's liver, and generate an undesirable non-specific immune response.

Oil, when added as a component of an adjuvant, generally provides a long and slow release profile. Oils that can be utilized are metabolizable oils or non-metabolizable oils. An oil can be in the form of an oil-in-water, a water-in-oil, or a water-in-oil-in-water emulsion. An oil-in-water emulsion can be provided in some embodiments, and can be composed of an AMPHIGEN® formulation. This formulation comprises an aqueous component, lecithin, mineral oil, and surfactants. Patents describing the components of the formulation include U.S. Pat. No. 5,084,269 and U.S. Pat. No. 6,572,861. An oil component can be present in an amount from 1% to 50% by volume, or in an amount of 10% to 45%; or in an amount from 20% to 40% in some embodiments.

Suitable oils can include alkanes, alkenes, alkynes, and their corresponding acids and alcohols, the ethers and esters thereof, and mixtures thereof. Individual compounds of the oil often are light hydrocarbon compounds, i.e., such components often have 6 to 30 carbon atoms. The oil can be synthetically prepared or purified from petroleum products. The moiety may have a straight or branched chain structure. It may be fully saturated or have one or more double or triple bonds. Some non-metabolizable oils for use in the present invention include mineral oil, paraffin oil, and cycloparaffins, for example. A "light mineral oil" can be selected for use in an immunostimulatory composition. One type of oil utilized is obtained by distillation of petrolatum, and has a slightly lower specific gravity than white mineral oil.

Metabolizable oils include metabolizable, non-toxic oils. This type of oil can be any vegetable oil, fish oil, animal oil or synthetically prepared oil that can be metabolized by the body of the subject to which an immunostimulatory composition is administered and is not toxic to the subject. Sources for vegetable oils include nuts, seeds and grains.

Other components of an immunostimulatory composition can include pharmaceutically acceptable excipients, such as carriers, solvents, and diluents, isotonic agents, buffering agents, stabilizers, preservatives, vaso-constrictive agents, antibacterial agents, antifungal agents, and the like. Non-limiting examples of carriers, solvents, and diluents include water, saline, dextrose, ethanol, glycerol, oil, and the like. Examples of isotonic agents include sodium chloride, dextrose, mannitol, sorbitol, lactose, and the like. Useful stabilizers include gelatin, albumin, and the like.

A surfactant can be used to assist in stabilization of an emulsion and can be selected to act as a carrier for an adjuvant and/or antigen. Surfactants suitable for use include natural biologically compatible surfactants and non-natural synthetic surfactants, in some embodiments. Biologically compatible surfactants include phospholipid compounds or a mixture of phospholipids. An example of a phospholipid is phosphatidylcholine (lecithin), such as soy or egg lecithin. Lecithin can be obtained as a mixture of phosphatides and triglycerides by water-washing crude vegetable oils, and separating and drying the resulting hydrated gums. A refined product can be obtained by fractionating the mixture for acetone insoluble phospholipids and glycolipids remaining after removal of the triglycerides and vegetable oil by acetone washing. Alternatively, lecithin can be obtained from various commercial sources. Other suitable phospholipids include phosphatidylglycerol, phosphatidylinositol, phosphatidylserine, phosphatidic acid, cardiolipin, and phosphatidylethanolamine. The phospholipids may be isolated from natural sources or conventionally synthesized.

Non-natural, synthetic surfactants that can be used include, without limitation, sorbitan-based non-ionic surfactants, e.g. fatty-acid-substituted sorbitan surfactants (commercially available under the name SPAN® or ARLACEL®); fatty acid esters of polyethoxylated sorbitol (TWEEN®); polyethylene glycol esters of fatty acids from sources such as castor oil (EMULFOR®); polyethoxylated fatty acid (e.g., stearic acid available under the name SIMULSOL M-53®); polyethoxylated isooctylphenol/formaldehyde polymer (TYLOXAPOL®); polyoxyethylene fatty alcohol ethers (BRIJ®); polyoxyethylene nonphenyl ethers (TRITON® N), polyoxyethylene isooctylphenyl ethers (TRITON® X). In some embodiments, a surfactant, or combination of surfactants, is present in an emulsion in an amount of 0.01% to 10% by volume, sometimes 0.1% to 6.0%, and at times 0.2% to 5.0%.

A pharmaceutically-acceptable carrier includes any and all solvents, dispersion media, coatings, stabilizing agents, diluents, preservatives, antibacterial and antifungal agents, isotonic agents, adsorption delaying agents, and the like. Carrier(s) generally are compatible with other components of an immunostimulatory composition and not deleterious to a subject when administered. A carrier often is sterile and pyrogen-free, and selected based on the mode of administration used, and a carrier utilized often is approved, or will be approved, by an appropriate government agency that oversees development and use of pharmaceuticals. An immunostimulatory composition can include, in certain embodiments, a compatible pharmaceutically acceptable (i.e., sterile or non-toxic) liquid, semisolid, or solid diluent that serves as a pharmaceutical vehicle, excipient, or medium. A diluent can include water, saline, dextrose, ethanol, glycerol, and the like, for example. An isotonic agent can include sodium chloride, dextrose, mannitol, sorbitol, and lactose, among others. A stabilizer can include albumin, among others. An immunostimulatory composition can include, in some embodiments, an antibiotic or preservative, including, for example, gentamicin, merthiolate, or chlorocresol.

Preparation of Immunostimulatory Compositions

A compound described herein can be used in the manufacture of an immunostimulatory composition. Each dose can contain a therapeutically effective amount of an antigen or antigens (e.g., vaccine) that can vary depending on the age and general condition of the subject, the route of administration, the nature of the antigen, and other factors. The amounts and concentrations of other components in the immunostimulatory composition may be adjusted to modify the physical and chemical properties of the composition, and can be determined. An immunostimulatory composition can be homogenized or microfluidized as described hereafter.

An immunostimulatory composition can be prepared as an immune stimulating complex (ISCOM). An ISCOM can be prepared by combining a saponin, a sterol, and a phospholipid. For example, an ISCOM can contain 5% to 10% by weight Quil A, 1% to 5% cholesterol and phospholipids, and the remainder protein. The ratio of saponin to sterol in the adjuvant formulations sometimes is in the order of from 1:100 weight to weight (w/w) to 5:1 w/w. In some embodiments, excess sterol is present and the ratio of saponin to sterol can be at least 1:2 w/w, or 1:5 w/w. In certain embodiments, saponin is in excess in relation to the sterol, and a ratio of saponin to sterol of about 5:1 w/w is used. ISCOM and ISCOMATRIX are commercially available (e.g., Isconova AB (Sweden)).

In some embodiments, CARBOPOL® is used in combination with DDA in an amount of at least 0.1 part by weight of CARBOPOL® per part by weight of DDA. In certain embodiments, at least 0.5 part by weight of CARBOPOL® per part by weight of DDA is used. In various embodiments, at least 1 part by weight of CARBOPOL® per part by weight of DDA is used. The combination of CARBOPOL® and DDA often forms a complex whereby the DDA tertiary amine functional group immunofunctionalizes the carboxylic acid side groups on the polymer. This complex allows for specific immune cells to target an antigen and adjuvant simultaneously and co-deliver the antigen and adjuvant together at the optimal time and concentration to the said cells.

In some embodiments, a compound described herein is not formulated with a specific carrier, and sometimes is formulated in an aqueous or other pharmaceutically acceptable buffer for preparation of an immunostimulatory composition. In some embodiments, an immunostimulatory composition is presented in a suitable vehicle, such as for example, additional liposomes, microspheres or encapsulated antigen particles. An antigen, if present in an immunostimulatory composition, can be contained within the vesicle membrane or contained outside the vesicle membrane. Soluble antigens often are inside and hydrophobic or lipidated antigens often are contained within the membrane.

An immunostimulatory composition can be made in various forms depending upon the route of administration, storage requirements, and the like. For example, they can be made in the form of sterile aqueous solutions or dispersions suitable for injectable use, or made in lyophilized forms using freeze-drying, vacuum-drying, or spray-drying techniques. Lyophilized compositions can be reconstituted prior to use in a stabilizing solution, e.g., saline or HEPES. Thus, an immunostimulatory composition can be used as a solid, semi-solid, or liquid dosage form.

Phosphate buffered saline (PBS) may be used as an aqueous buffer medium, where the pH of the buffer may be neutral or slightly alkaline or slightly acidic. Accordingly, the pH can be in a range of pH 6 to 8, and a pH of about 7.0 to about 7.3 can be used in certain embodiments. The pH can be adjusted using a base (e.g., NaOH) or base (e.g., HCl) as needed. Typical concentrations include from 1N to 10N HCl and 1N to 10N NaOH, for example. The strength of the buffer can be between 10 to 50 mM PO.sub.4 and between 10 to 150 mM PO.sub.4 in some embodiments. In certain embodiments, a composition forms particles, for example nanoparticles, of about 10 nanometers to about 1000 nanometers, and sometimes, a composition forms particles with a mean, average or nominal size of about 100 nanometers to about 400 nanometers.

An immunostimulatory composition can be homogenized or microfluidized, in some embodiments. An immunostimulatory composition may be subjected to a primary blending process, such as by passage one or more times through one or more homogenizers, in certain embodiments. Any commercially available homogenizer can be used for this purpose, e.g., Ross emulsifier (Hauppauge, N.Y.), Gaulin homogenizer (Everett, Mass.), or Microfluidics (Newton, Mass.). In some embodiments, an immunostimulatory composition homogenized for three minutes at 10,000 rpm. Microfluidization can be achieved by use of a commercial microfluidizer, such as model number 11OY available from Microfluidics, (Newton, Mass.); Gaulin Model 30CD (Gaulin, Inc., Everett, Mass.); and Rainnie Minilab Type 8.30H (Miro Atomizer Food and Dairy, Inc., Hudson, Wis.). These microfluidizers operate by forcing fluids through small apertures under high pressure, such that two fluid streams interact at high velocities in an interaction chamber to form compositions with droplets of a submicron size. In certain embodiments, the formulations are microfluidized by passage through a 200 micron limiting dimension chamber at 10,000.+/−.500 psi.

Administration of Immunostimulatory Compositions

Dose size of an immunostimulatory composition can range from about 1 mL to about 5 mL, inclusive, depending on the subject and the antigen. For example, for a canine or feline, a dose of about 1 mL is typically used, while in cattle a dose of about 2-5 mL is typically used. However, an immunostimulatory composition can be formulated in a microdose, where doses of about 100 microliters can be used.

Non-limiting routes of administration for an immunostimulatory composition include parenteral, oral, oronasal, intranasal, intratracheal, topical, injection and intradermal. Any suitable device may be used to administer the compositions, including syringes, droppers, needleless injection devices, patches, pump, particles (e.g., gold microparticles), electrotransduction, electroporation and the like. The route and device selected for use will depend on the composition of the adjuvant, the antigen, and the subject, as known in the art. In some embodiments, an immunostimulatory composition is administered by intravesical instillation.

An immune response can be monitored after an immunostimulatory composition is administered to a subject. Methods for assessing an immune response are known in the art, and include methods provided herein such as, for example, assaying antibody titer, either specific or non-specific, and measuring serum cytokine levels In some embodiments, an antigen-specific immune response (e.g., antigen-specific antibodies, antigen-specific cytotoxic T-cells (CTLs)) is assessed after an immunostimulatory composition is delivered. In some embodiments, an IgG1 and/or IgG2 (e.g., IgG2a) antibody response is induced. An immune response can be assessed after an immunostimulatory composition is delivered. In some embodiments, a composition described herein induces little to no side effects (e.g., splenomegaly) when administered to a subject.

EXAMPLES

The examples set forth below illustrate certain embodiments and do not limit the technology.

Example 1

Synthesis of 4-((6-amino-2-(2-methoxyethoxy)-8-oxo-7H-purin-9(8H)-yl)methyl)benzoic acid (compound 7)

This Example details methods by which compound A and SC12 can be prepared, and includes the following methods and data:
  a method for preparation of 4-((6-amino-2-(2-methoxyethoxy)-8-oxo-7H-purin-9(8H)-yl)methyl)benzoic acid (compound 7) and its conjugation with 1,2-dioleoyl-sn-glycero-3-phosphoethanolamine (DOPE)
  conditions for preparation of compound 7 and scale-up of the preparation on multi-gram scale
  a method of conjugation of compound 7 with 1,2-dioleoyl-sn-glycero-3-phosphoethanolamine (DOPE) to obtain compound A
  a method for preparation of compound A on multi-gram scale
  analytical methods for intermediates and for the conjugated compound
  stability study of compound A
  a method for preparation of SC12, also known as SC12, a conjugated derivative of 7 with 1,2-dilauroyl-sn-glycero-3-phosphoethanolamine (DLPE))
  stability study of SC12

The following schemes present an example of methods that may be used to prepare compound A and SC12. Other synthetic methods may be used to prepare compound A and SC12, examples of these other synthetic methods are provided in FIGS. 20-23.

Scheme 1

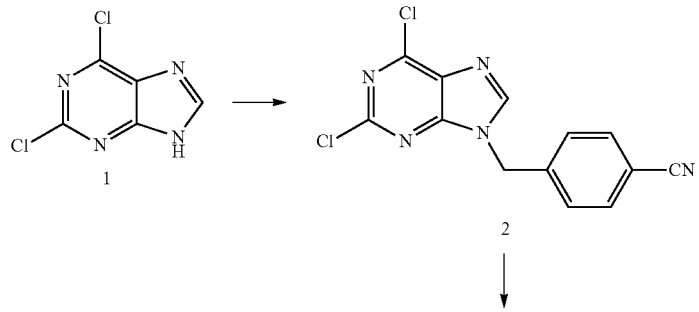

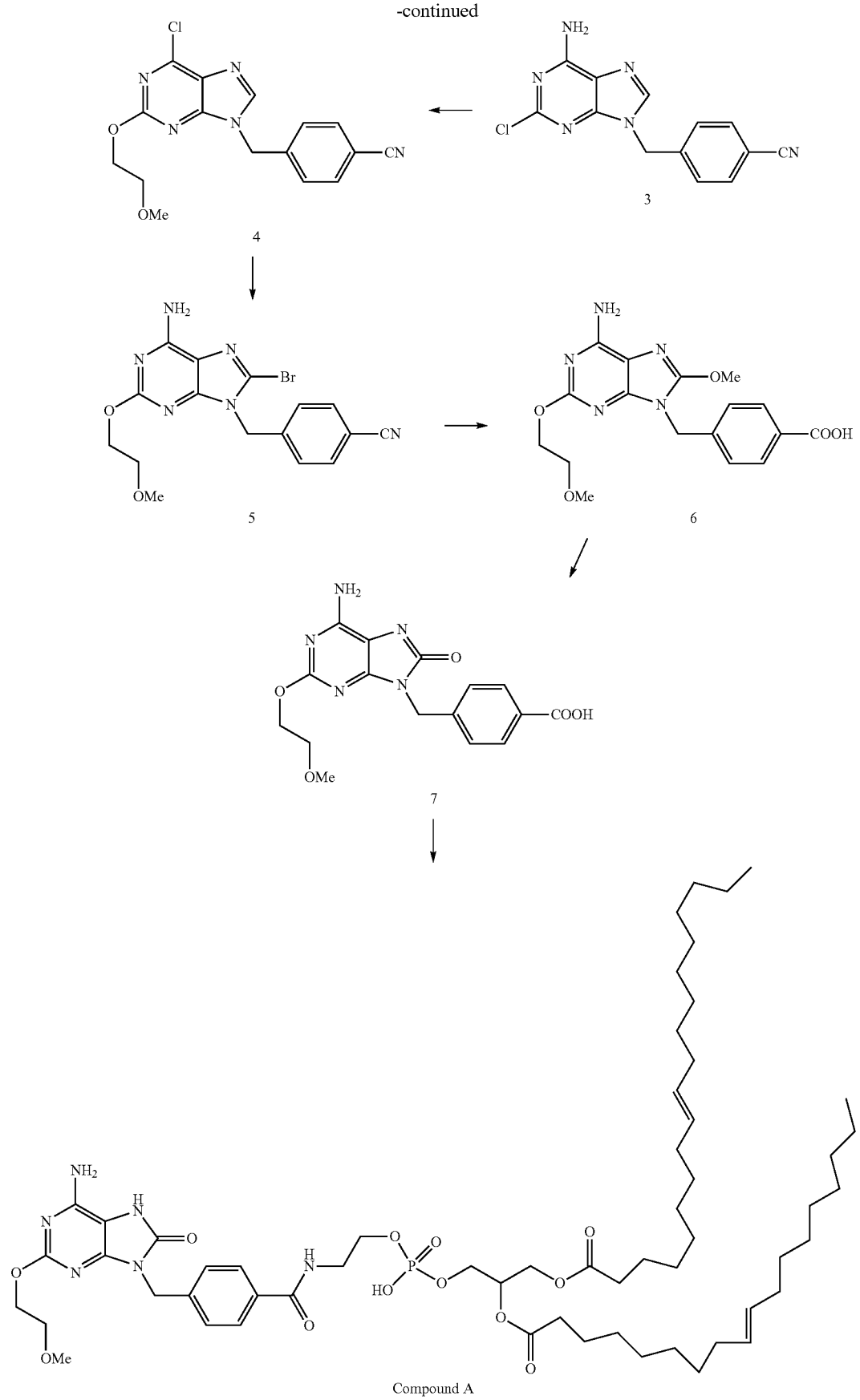

A. Preparation of 4-((6-amino-2-(2-methoxyethoxy)-8-oxo-7H-purin-9(8H)-yl)methyl)benzoic acid 7

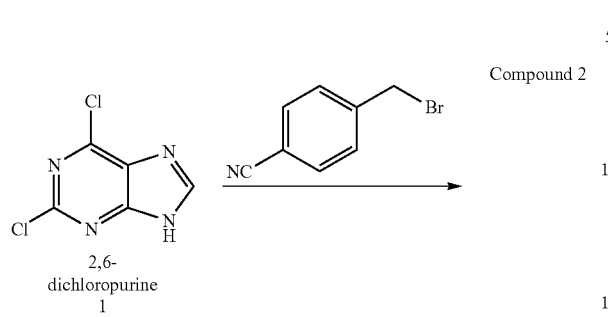

Compound 2

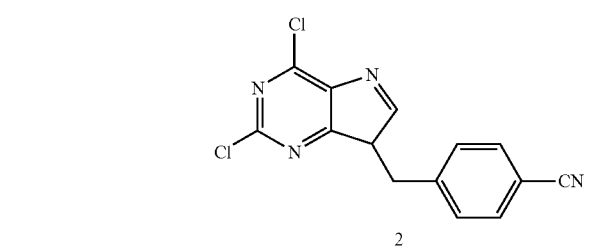

2,6-dichloropurine (100 g, 0.53 mol) is charged in a four necked round bottomed flask, 3 L, equipped with mechanical stirrer, oil bath, thermometer, dropping funnel, reflux condenser and nitrogen inlet. N,N-dimethylacetamide (1 L) is added, followed by solid bromomethyl-benzonitrile (114.6 g, 0.58 mol, 1.1 eqv.) and potassium carbonate (109.7 g, 0.79 mol, 1.5 eqv.). The mixture is vigorously stirred and heated at 85-90° C. for 3 hrs, then it is allowed to cool to room temperature and added with water (2 L). A yellow abundant solid immediately is formed; the mixture is stirred for 30 min, then it is filtered in a Buchner funnel, washed with water (2×200 mL) and ethyl acetate and dried at 65° C. in vacuum until constant weight is observed (about 5 hs). Intermediate 2, batch CH730/2/1 is obtained as a pale yellow solid, with the following sample amount and purity: 160 g; 99% Y; 90.2% HPLC purity. NMR and MS analysis conforms to the structure.

The reaction is scaled up and repeated starting from 600 g of 2,6-dichloropurine. Intermediate 2 batch CH730/3/1 is obtained, with the following sample amount and purity: 950 g; 98.3% Y; 92% HPLC purity.

Compound 3

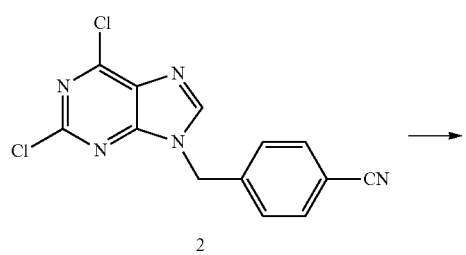

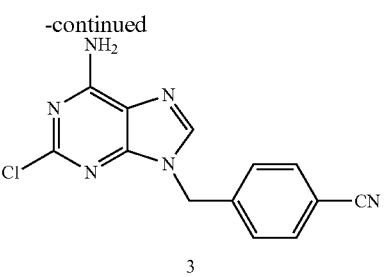

Intermediate 2 (100 g, 0.33 mol) is charged in a four necked round bottomed flask, 3 L, equipped with mechanical stirrer, oil bath, thermometer, dropping funnel, reflux condenser and nitrogen inlet. Dry dimethylformamidegg (700 mL) is added, followed by ammonia solution 7 N in methanol (100 mL, 0.66 mol, 2 eqv.). The mixture is vigorously stirred at room temperature. After 2 hours a brown solution is obtained, then an abundant solid precipitated. The mixture is further stirred for 12 hours, then the solid is filtered on a Buchner funnel and washed with ethyl acetate (200 mL). The product is dried at 65° C. in vacuum until constant weight is observed (about 6 hs). Intermediate 3 batch CH730/3/2 is obtained as a whitish solid with the following sample amount and purity: 66 g; 71% Y; 92.9% HPLC purity, NMR and MS analysis conforms to the structure.

The reaction is scaled up and repeated on 900 g of intermediate 2. Intermediate 3 batch CH730/6/2 is obtained, with the following sample amount and purity: 680 g; 77% Y; 91% HPLC purity.

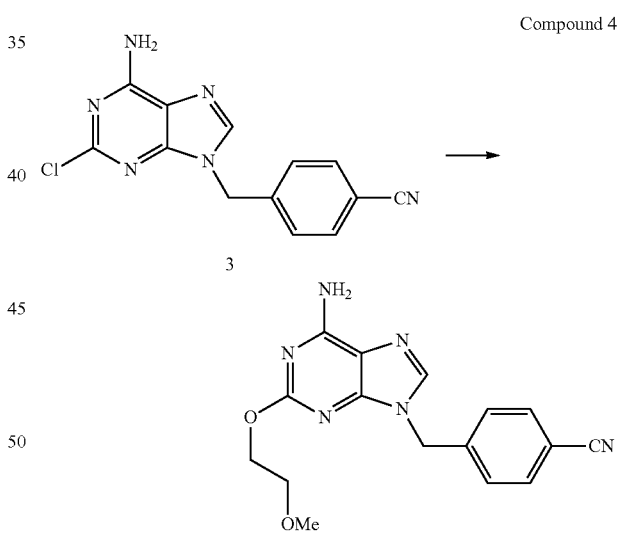

Compound 4

A four necked round bottomed flask, 1 L, equipped with mechanical stirrer, oil bath, thermometer, dropping funnel, reflux condenser and nitrogen inlet is charged with 2-methoxy ethanol (500 mL). Sodium (6 g, 0.26 mol, 1.5 eqv) is added in small pieces at room temperature and under Argon atmosphere. Intermediate 3 (50 g, 0.175 mol) is added in one portion. The reaction mixture is stirred and heated to 100° C. for 6 hours, then it is allowed to cool to room temperature. Water (1 L) is added and the mixture is stirred at room temperature for 30 min. The solid is filtered on a Buchner funnel, washed with water (200 mL) and dried in vacuum at 65° C.

until constant weight (about 8 hours). Intermediate 4, batch CH730/2/3 is obtained as a whitish solid with the following sample amount and purity: 40 g; 70% Y; 95% % HPLC purity. NMR and MS analysis conform to the structure.

The reaction is scaled up and repeated on 550 g of compound 3. Intermediate 4 batch CH730/6/3 is obtained with the following sample amount and purity: 532 g; 78% Y. 94% HPLC purity.

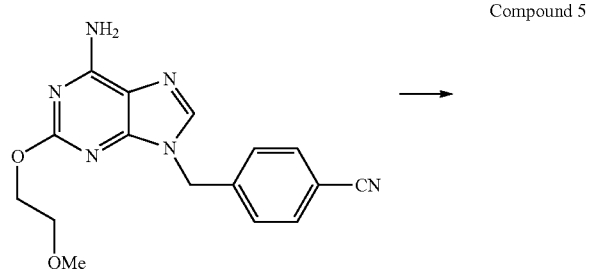

Compound 5

4

Intermediate 4 (100 g, 0.3 mol) is charged into a four necked round bottomed flask, 2 L, equipped with mechanical stirrer, oil bath, thermometer, dropping funnel, reflux condenser and nitrogen inlet Dichloromethane (1.5 L) is added and the mixture is vigorously stirred at room temperature. Bromine (19 mL, 0.37 mol, 1.2 eqv.) is added drop wise at room temperature. After stirring for 8 hs, the solid is filtered and washed with dichloromethane (300 mL) to give crude compound 5 as a yellow solid. It is crystallized with acetone (500 mL) to give intermediate 5 as a pale yellow solid with the following sample amount and purity: Batch CH730/3/4; 109 g; 88% Y. 82% HPLC purity.

The reaction is repeated on 150 g of compound 4; intermediate 5, batch CH730/4/4 is obtained; with the following sample amount and purity: 170 g; 92% Y; 81% HPLC purity. A third preparation is made; intermediate 5, batch CH730/11/4 is obtained; with the following sample amount and purity: 80 g; 91% HPLC purity.

Compound 7

5

A four necked round bottomed flask, 3 L, equipped with mechanical stirrer, oil bath, thermometer, dropping funnel, reflux condenser and nitrogen inlet is charged with methanol (700 mL). Sodium (11.9 g, 0.52 mol, 3 eqv.) is added in small pieces. Intermediate 5 (70 g, 0.17 mol) is added to the solution in one portion. The suspension is vigorously stirred at reflux-untilagg clear solution is obtained (about 6 hours). The mixture is allowed to cool to room temperature, then water is added (500 mL) followed by sodium hydroxide (34 g, 0.85 mol). The mixture is again heated to reflux for 8 hours, then it is cooled to room temperature. Concentrated hydrochloric acid is added (120 mL); a white solid precipitates from the reaction mixture. After stirring for 1 hr, the solid is filtered on a Buchner funnel. After drying in vacuum at 65° C. (about 8 hs), crude compound 6 (50 g) is obtained. It is suspended in acetonitrile (500 mL) and added with Sodium Iodide (Aldrich, 34 g, 0.23 mol). After the drop wise addition of chlorotrimethylsilaneg (Aldrich, 29 mL, 0.23 mol), the mixture is vigorously stirred and heated to 50° C. for 3 hours. After cooling to room temperature, a saturated solution of sodium hydrogen carbonate is added, to obtain pH 6 into the reaction mixture. The solid precipitated is filtered on a Buchner funnel and washed first with water (100 mL), then with methanol (50 mL). Crude compound 7 is obtained as a pale yellow solid; batch CH730/18/6b, with the following sample amount and purity: 40 g, HPLC purity 89%

It is crystallized twice with glacial acetic acid (600 mL each time). After drying in vacuum at 65° C. for 8 hours, compound 7 batch CH730/18/6c is obtained; with the following sample amount and purity: 34 g; 55% Y from 5; 93.6% HPLC purity.

The reaction is repeated on 70 g of intermediate 5; compound 7, batch CH730/16/6b is obtained; with the following sample amount and purity: 38 g; 61% Y; 92% HPLC purity. The reaction is repeated again on 30 g of compound 5; compound 7, batch CH730/21/6d is obtained; with the following sample amount and purity: 18 g; 62% Y; 92.2% HPLC purity.

Acid 7 is not soluble in most of the common solvents (methanol, ethanol, dichloromethane, ethyl acetate, acetonitrile, acetone, chloroform). Many attempts are made aimed to crystallize acid 7; dimethylformamideggg, dimethylformamidegg/water, DMSO/water, methanol, acetone are tested, but in all cases the product after crystallization has the same purity as before crystallization. Glacial acetic acid may be effective in enhancing the purity of 7. The purity is increased after the first crystallization, but it remains unchanged when the treatment is repeated. The target value (98% HPLC) has not been achieved.

Preparation of Compound A mmol, 2 eqv). The mixture is stirred at room temperature for 15 min, then a solution of DOPE (1,2-dioleoyl-sn-glycero-3-phosphoethanolamine, 5.37 g, 7.2 mmol, 1 eqv.) in dry dichloromethane (150 mL) is added drop wise. The resulting solution is stirred for 12 hours, until complete conversion of the reagents. The HPLC analysis shows that compound A is about 85% in the crude reaction mixture. Dichloromethane is evaporated under reduced pressure and the residue is added drop wise to water (150 mL). A solid separates from the

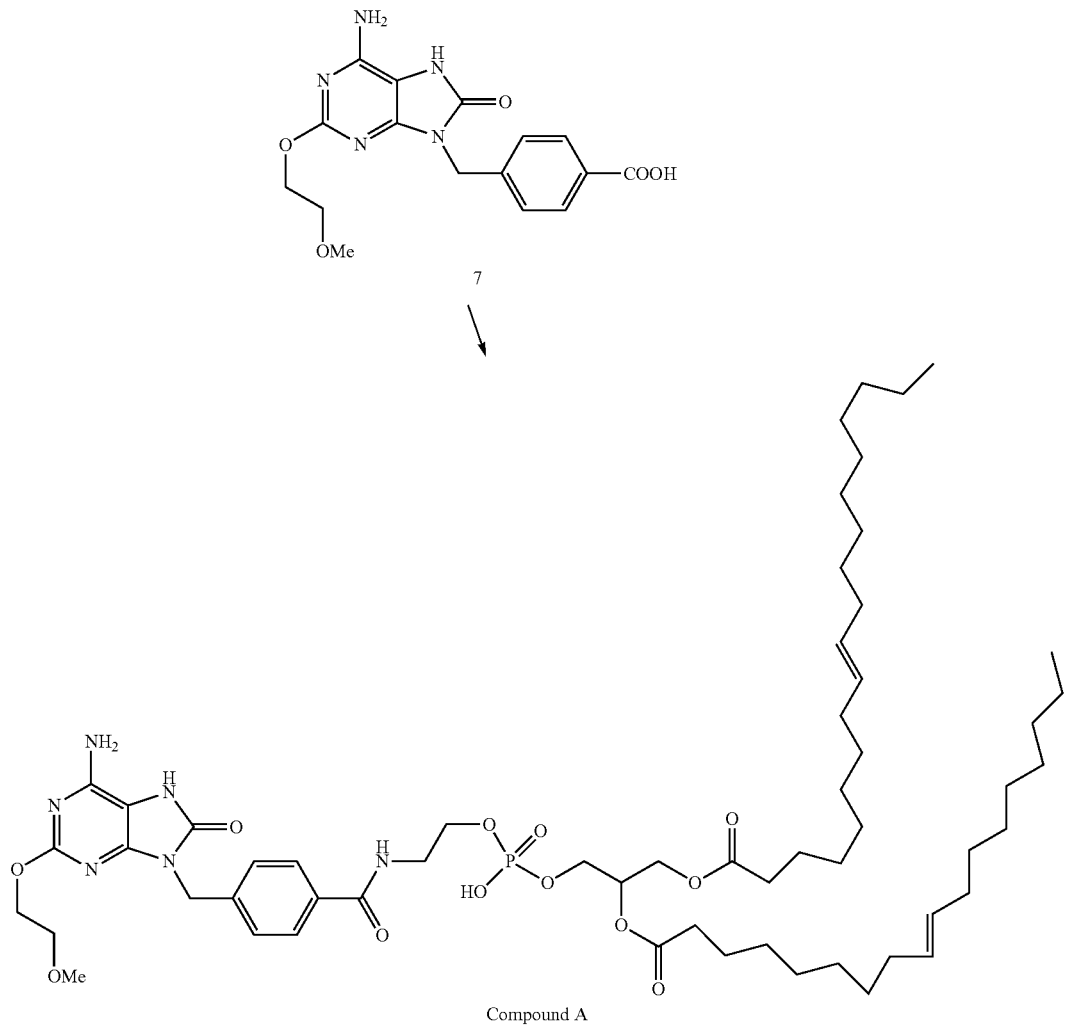

Compound A

Many attempts are made aimed to prepare compound A with good yield and purity. First, the direct coupling of acid 7 with DOPE is attempted (method A and method B). Then acid 7 is activated before coupling with DOPE (method C and method D). While reasonable results are obtained both with method A and method D, difficulties may arise during the work up of the reaction mixture and during the purification phase.

Method A: acid 7 (2.6 g, 7.2 mmol) is suspended in dry dimethylformamidegg (10 mL) under Argon atmosphere. HATU (O-7-azabenzotriazol-1-yl)-N,N,N,N-tetramethyluronium hexafluorophosphate; 2.94 g, 7.6 mmol, 1.05 eqv.) is added in one portion, followed by triethylamine (2 mL, 14.4 reaction mixture. The attempt of filtration under vacuum may fail because the product is not crystalline and the filter is blocked.

At this point dichloromethane (150 mL) is added and the phases are left to separate. A milky suspension forms and the separation of the two phases is not possible. In the event of failure of the filtration and of the extraction procedures, the solvents are completely removed by distillation under vacuum and the residue is purified by flash chromatography, eluting with dichloromethane/methanol/acetic acid 8/2/0.1. Compound A is obtained as a white amorphous solid with an example of HPLC purity of 94.6% (0.5 g).

The reaction is repeated starting from 15 g of acid 7. The outcome of the reaction is similar to the previous run. The crude is purified by chromatography, but the target product is obtained with low yield (7.2 g; 16% Y). When the silica gel used for the purification is washed with methanol/acetic acid 7/3, the residual product is recovered. Its purification is attempted again by chromatography. The purification by chromatography is effective on 1-2 grams scale; increasing the amount of compound A charged on the column, a great amount of product is retained by silica gel and the recovery is low. The amount of methanol and acetic acid has to be increased and at this point the product is recovered quantitatively, together with its impurities.

A crystallization technique also is attempted to purify compound A. Diethyl ether, hexane, acetone, acetone/water and other solvents are tested. Methanol is effective in lowering some impurities, but after prolonged heating in methanol a new impurity is detected (up to 20%).

At this point, the reaction conditions are studied to minimize impurities in the reaction crude. Lowering the temperature results in a better profile and compound A is obtained with 88% HPLC purity in the reaction mixture.

Method B: the reaction of acid 7 with DOPE is attempted using dicyclohexylcarbodiimide (DCC) and 1-ethyl-3-(3-dimethylaminopropyl)carbodiimide (EDCI) as coupling agents. In both cases no reaction occurs and the starting material is recovered unchanged.

Method C: the activation of acid 7 is attempted with 1-hydroxypyrrolidine in dichloromethane as solvent. Due to the insolubility of 7 in dichloromethane, the reaction fails.

Method D: acid 7 (10 g, 0.028 mol) is dissolved in a mixture of acetonitrile (60 mL) and dimethylsulfoxide (DMSO) (60 mL) at room temperature and under Argon atmosphere. Carbonyl diimidazole (4.55 g, 0.028 mol, 1 eqv.) is added and the resulting solution is stirred for 1 hr. A solution of DOPE (NOF Corp.>99%; 20.8 g, 0.028 mol, 1 eqv.) in dry dichloromethane is added drop wise. The reaction mixture is stirred for 16 hours, until complete conversion of the reagents. Acetonitrile is removed by distillation in vacuum; water (200 mL) is added to the residue; a white solid separated, but the filtration is not possible. The mixture is centrifuged for 30 min; the solvent is discarded and compound A batch CH730/16/8 is obtained as a solid, 25 g. It is rapidly passed through silica gel, eluting with dichloromethane/isopropanol/acetic acid 7/2/1 (CH730/16/8c, with the following sample amount and purity: 21 g; 89.6% HPLC purity) then it is treated with methanol at room temperature for 30 min and filtered on a Buchner funnel. Compound A is obtained as a solid 19 g, HPLC purity 94.5%. The reaction is repeated on 20 g of acid 7 with similar results.

Comparing methods A and D, similar results are obtained as far as yield and purity of crude compound A, but the impurity profile is different. It is determined the purification of the sample obtained with method A on multi-grams scale is not feasible. The coupling reaction between acid 7 and DOPE is repeated several times and the isolation of compound A with purity>90% is not readily accomplished.

Synthetic Processes

Figure 20A:
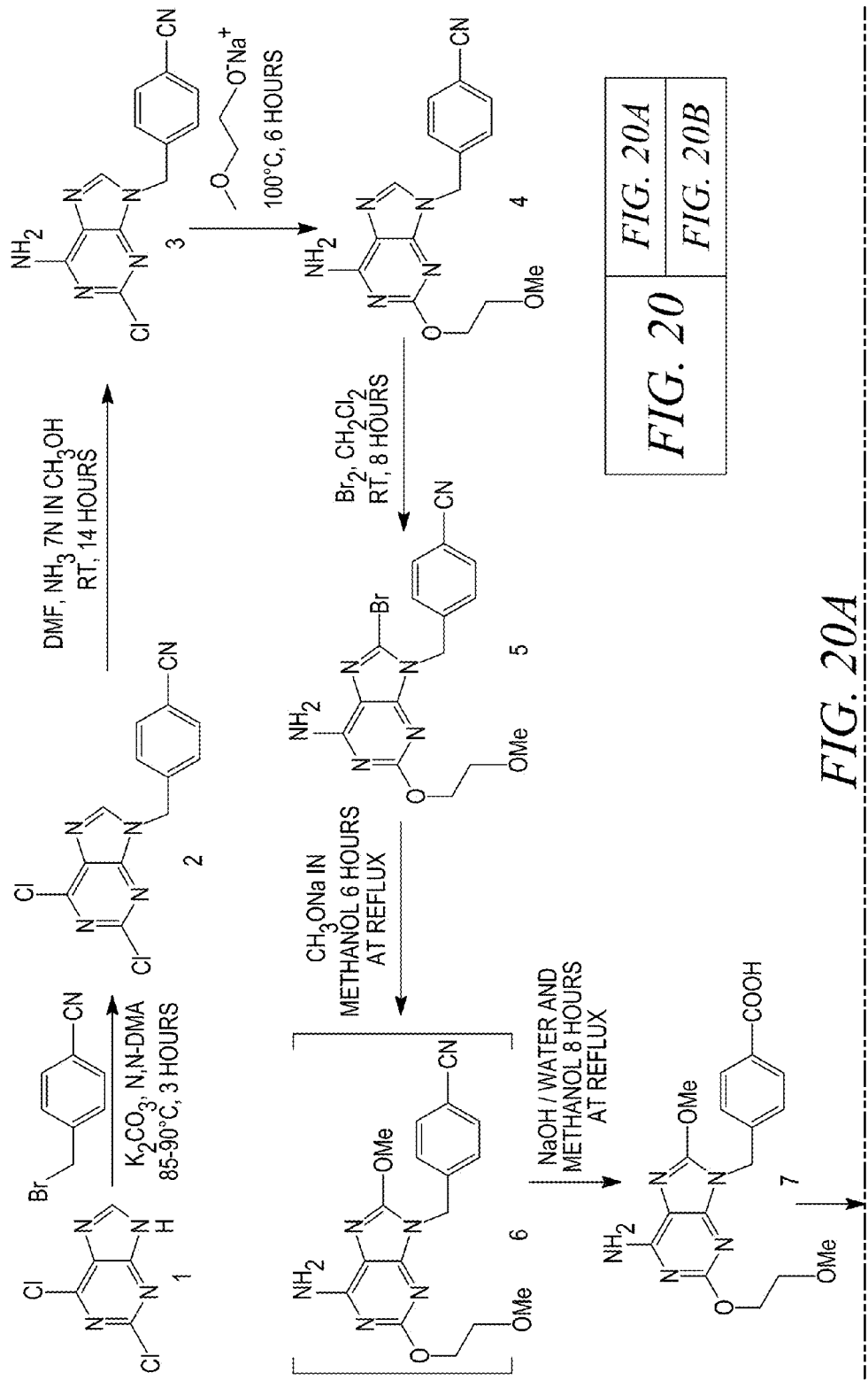
FIGS. 20A and 20B provide an example of a synthetic scheme for synthesis of compound A and SC12.
Figure 20B:
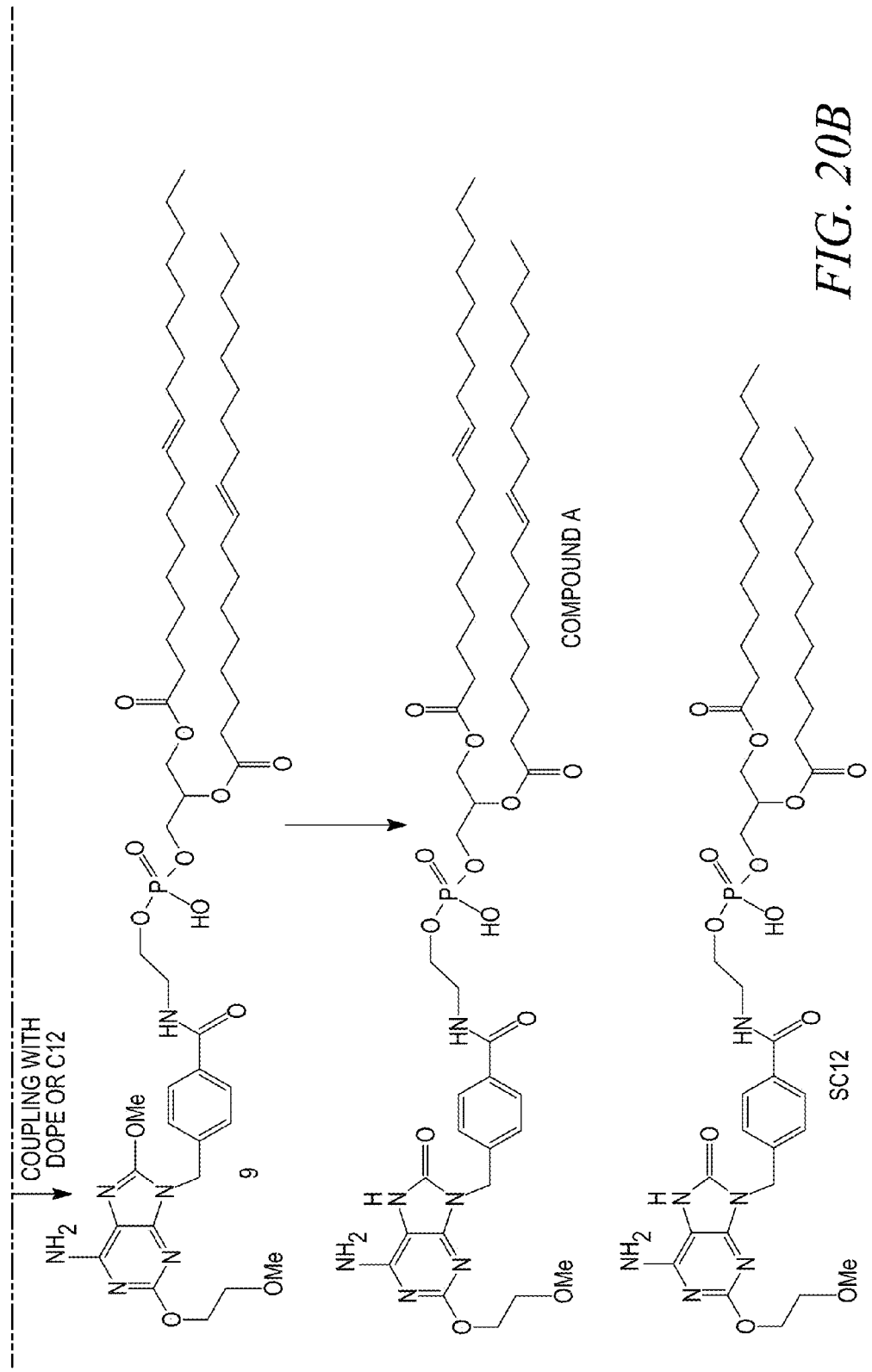

FIG. 20 shows examples of other synthetic process embodiments that can be utilized for manufacturing certain compounds having a structure of Formula A or Formula B. FIG. 20 specifically shows synthetic processes for manufacturing compound A and SC12. These process embodiments include an intermediate having a structure of Formula A or Formula B except for the hydroxyl moiety attached to the fused ring portion (8-hydroxyl) is a —O—(C1-C6 alkyl) moiety. This —O—(C1-C6 alkyl) moiety then is converted to the hydroxyl moiety shown in Formula A or Formula B. The —O—(C1-C6 alkyl) moiety sometimes is a —OCH3 moiety (i.e., —OMe moiety) as shown specifically in intermediate 9 of FIG. 20. The —O—(C1-C6 alkyl) moiety can be converted to the hydroxyl moiety by a process known in the art, such as a TMSCl/NaI hydrolysis procedure (e.g., Carey, Advanced Organic Chemistry IV Ed.—Part B: Reaction and Synthesis page 163) and/or a methyl enol ether hydrolysis (e.g., Bioorganic & Medicinal Chemistry 12 (2004) 1091-1099).

Figure 21B:
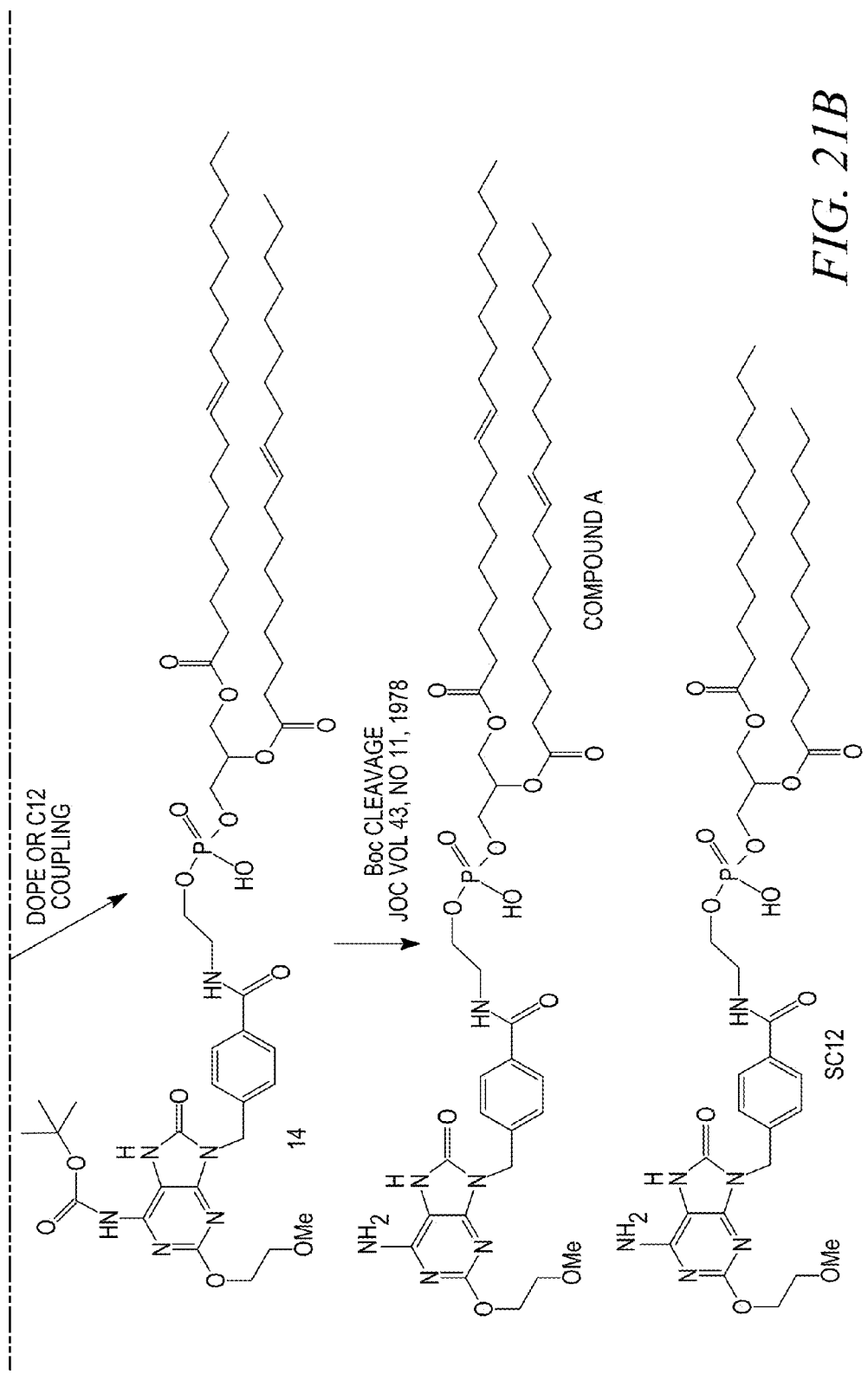
Figure 22A:
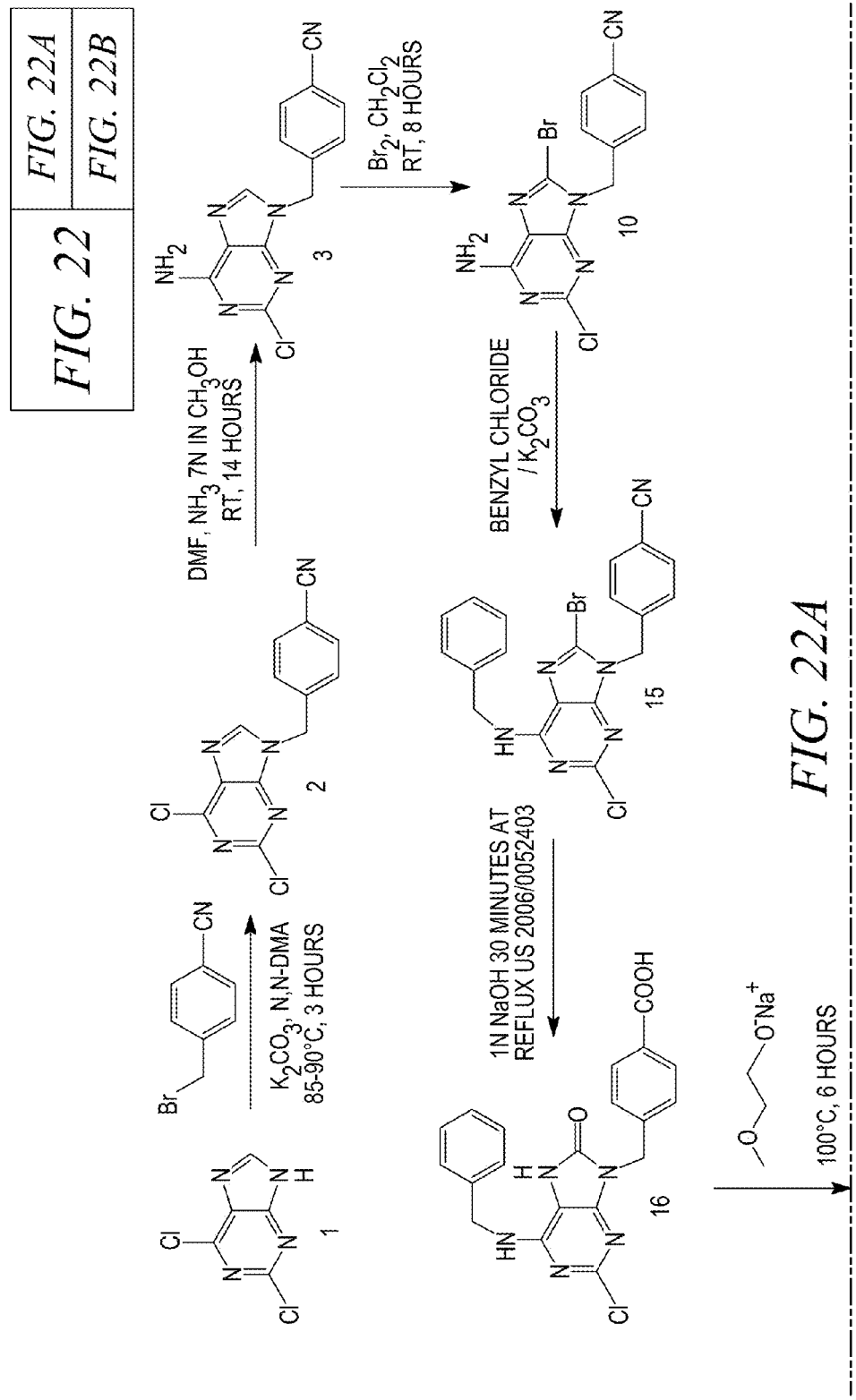
FIGS. 22A and 22B provide an example of a synthetic scheme for synthesis of compound A and SC12.
Figure 22B:
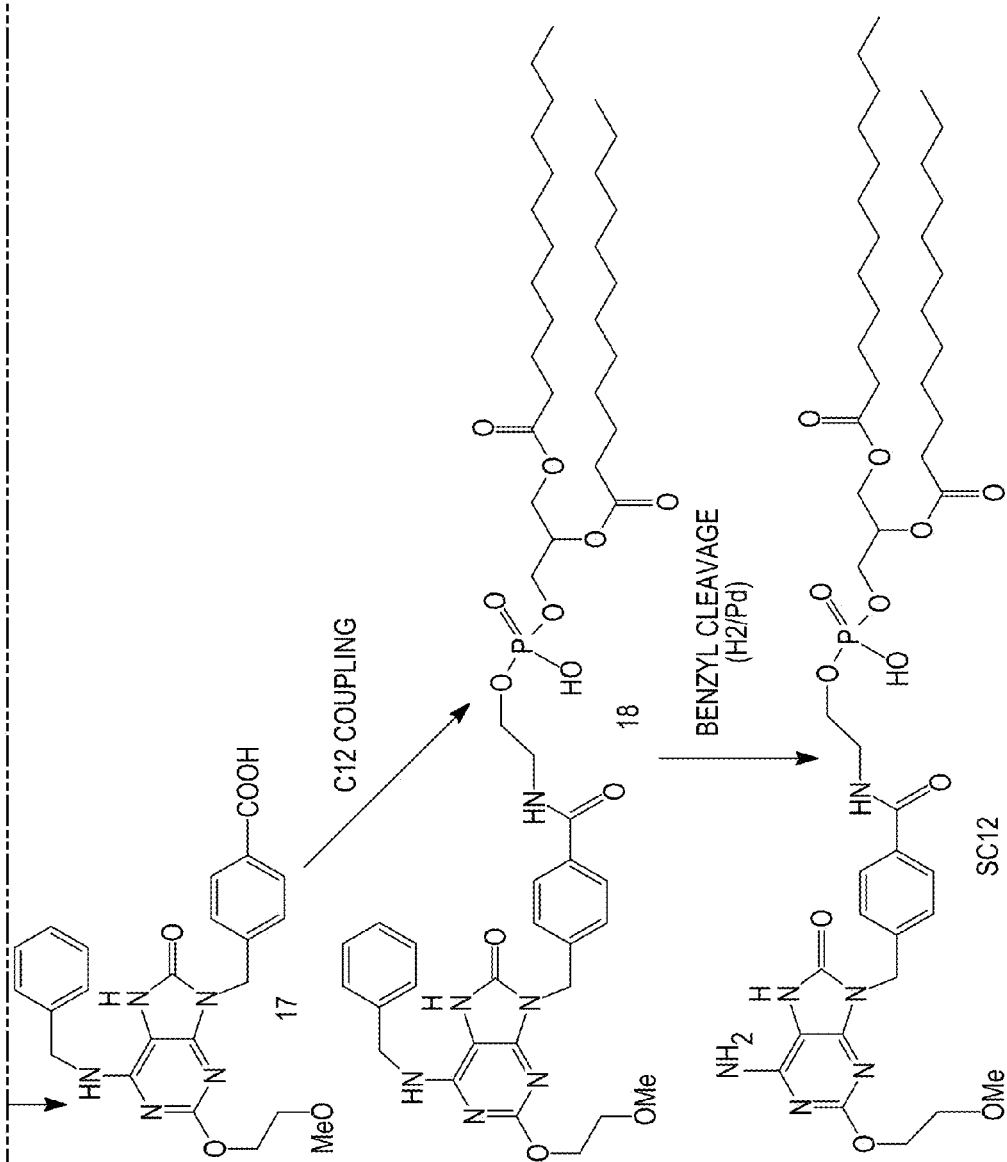

FIGS. 21 and 22 show further examples of synthetic process embodiments that can be utilized for manufacturing certain compounds having a structure of Formula A or Formula B. FIG. 21 and FIG. 22 specifically show synthetic processes for manufacturing compound A and SC12. These process embodiments includes an intermediate having a structure of intermediate 7 in Scheme 1 shown previously except that the primary amine moiety in intermediate 7 of Scheme 1 is a secondary amine having the structure —NH-(prot), where the prot moiety is a protecting group (e.g., intermediate 13 in FIG. 21 and intermediate 17 in FIG. 22). These process embodiments also include an intermediate having a structure of Formula A or Formula B except that the primary amine moiety in Formula A or Formula B is a secondary amine having the structure —NH-(prot) (e.g., intermediate 14 in FIG. 21 and intermediate 18 in FIG. 22). Any suitable protecting group known in the art can be utilized, and the protecting group sometimes is a tert-butoxycarbonyl (Boc) protecting group as shown by way of example in FIG. 21 (e.g., intermediates 13 and 14 in FIG. 21) or a benzyl protecting group as shown by way of example in FIG. 22 (e.g., intermediates 17 and 18 in FIG. 22). Certain protecting groups are suitable for producing compounds in which Rd and Re are saturated alkyl moieties (e.g., Boc and benzyl) and certain protection groups are suitable for producing compounds in which Rd and Re are alkyl moieties that include one or more unsaturations (e.g., Boc).

Figure 23A:
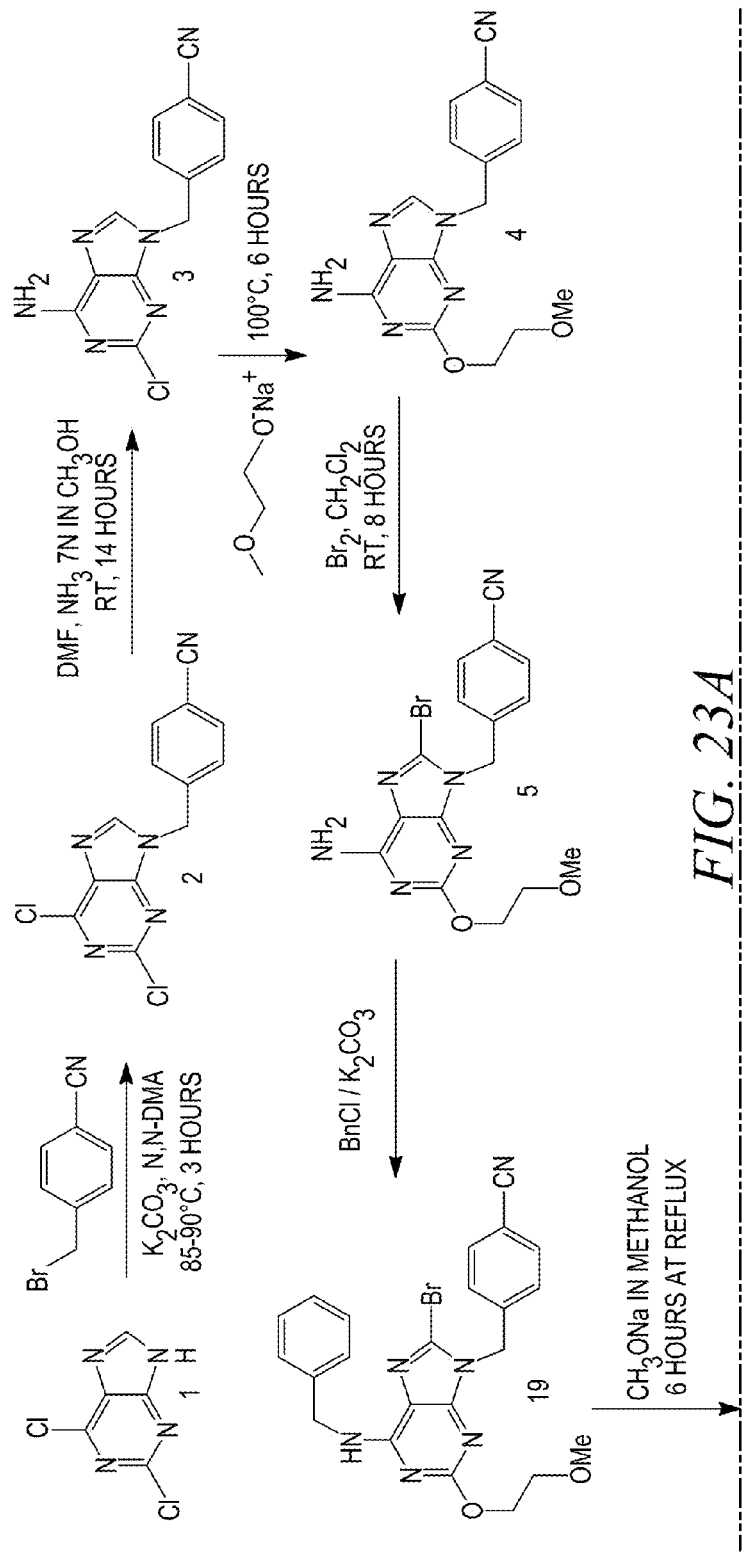
FIGS. 23A and 23B provide an example of a synthetic scheme for synthesis of compound A and SC12.
Figure 23B:
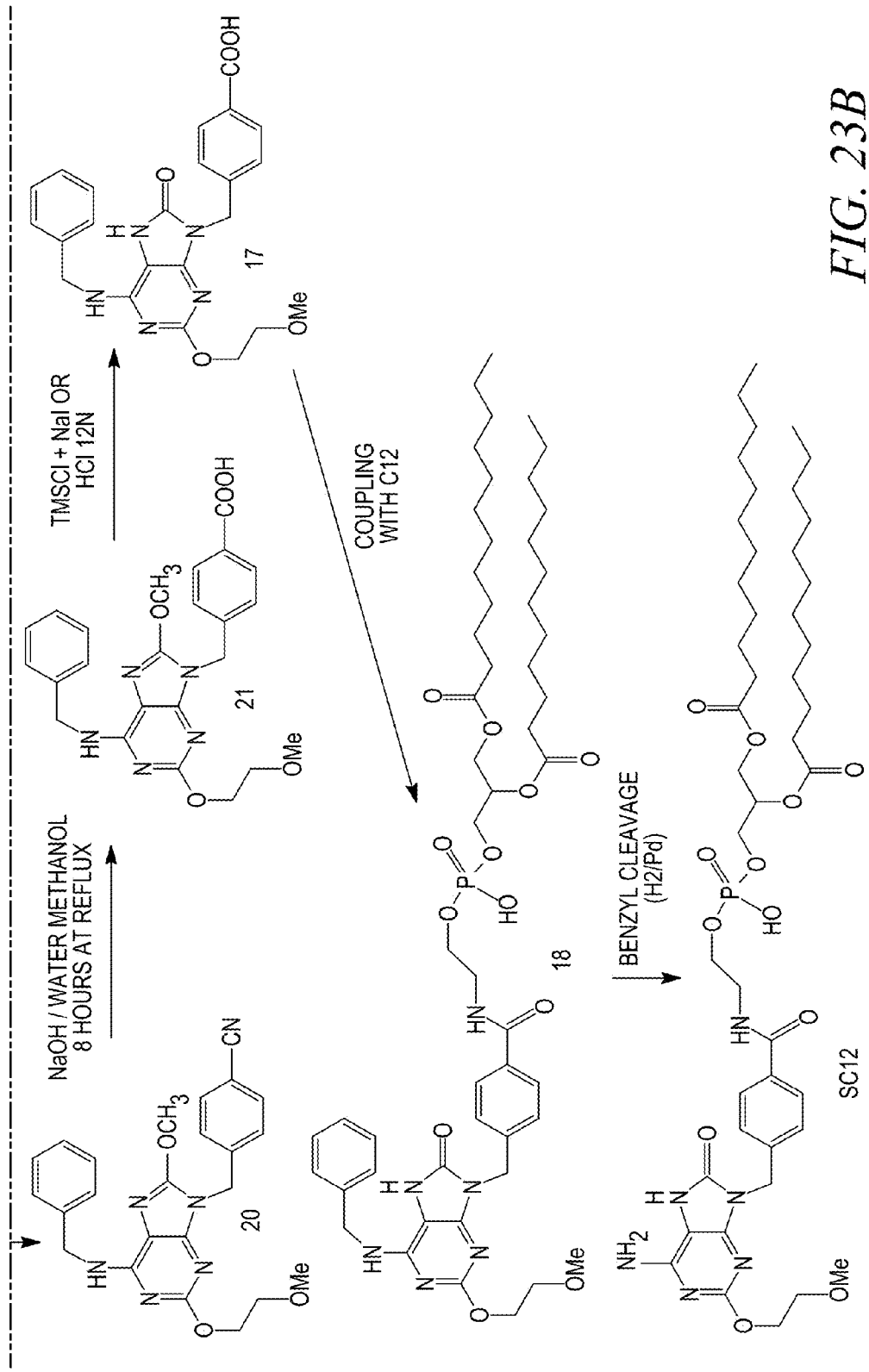

FIG. 23 shows examples of other synthetic process embodiments that can be utilized for manufacturing certain compounds having a structure of Formula A or Formula B. FIG. 23 specifically shows a synthetic process for manufacturing SC12. This process embodiment includes an intermediate having a structure of intermediate 7 in Scheme 1 shown previously except that the primary amine moiety in intermediate 7 is a secondary amine having the structure —NH-(prot), where the prot moiety is a protecting group (e.g., intermediate 17 in FIG. 23). This process embodiment also includes an intermediate having a structure of Formula A or Formula B except that the primary amine moiety in Formula A or Formula B is a secondary amine having the structure —NH-(prot) (e.g., intermediate 18 in FIG. 23). This process embodiment further includes an intermediate having a structure of intermediate 6 in Scheme 1 shown previously except that the primary amine moiety in intermediate 6 is a secondary amine having the structure —NH-(prot) (e.g., intermediate 21 in FIG. 23). Any suitable protecting group known in the art can be utilized, and the protecting group sometimes is a benzyl protecting group as shown by way of example in FIG. 23.

In FIGS. 20-23, the number designations for the various compounds in the synthetic scheme may not correspond with the numbers used in other figures, or the numbers used in this Example 1.

Sample Preparation for HPLC:

Intermediate no 5: in a 10 ml class A volumetric flask about 10 mg, accurately weighted, of sample were dissolved in methanol with some drops of dimethyl sulfoxide (final concentration about 1 mg/ml). Intermediate no 7: in a 10 ml class A volumetric flask about 5 mg, accurately weighted, of sample were dissolved in methanol with some drops of dimethyl sulfoxide (final concentration about 0.5 mg/ml).

Fragmentation of Compound A (Top Compound Shown Below)
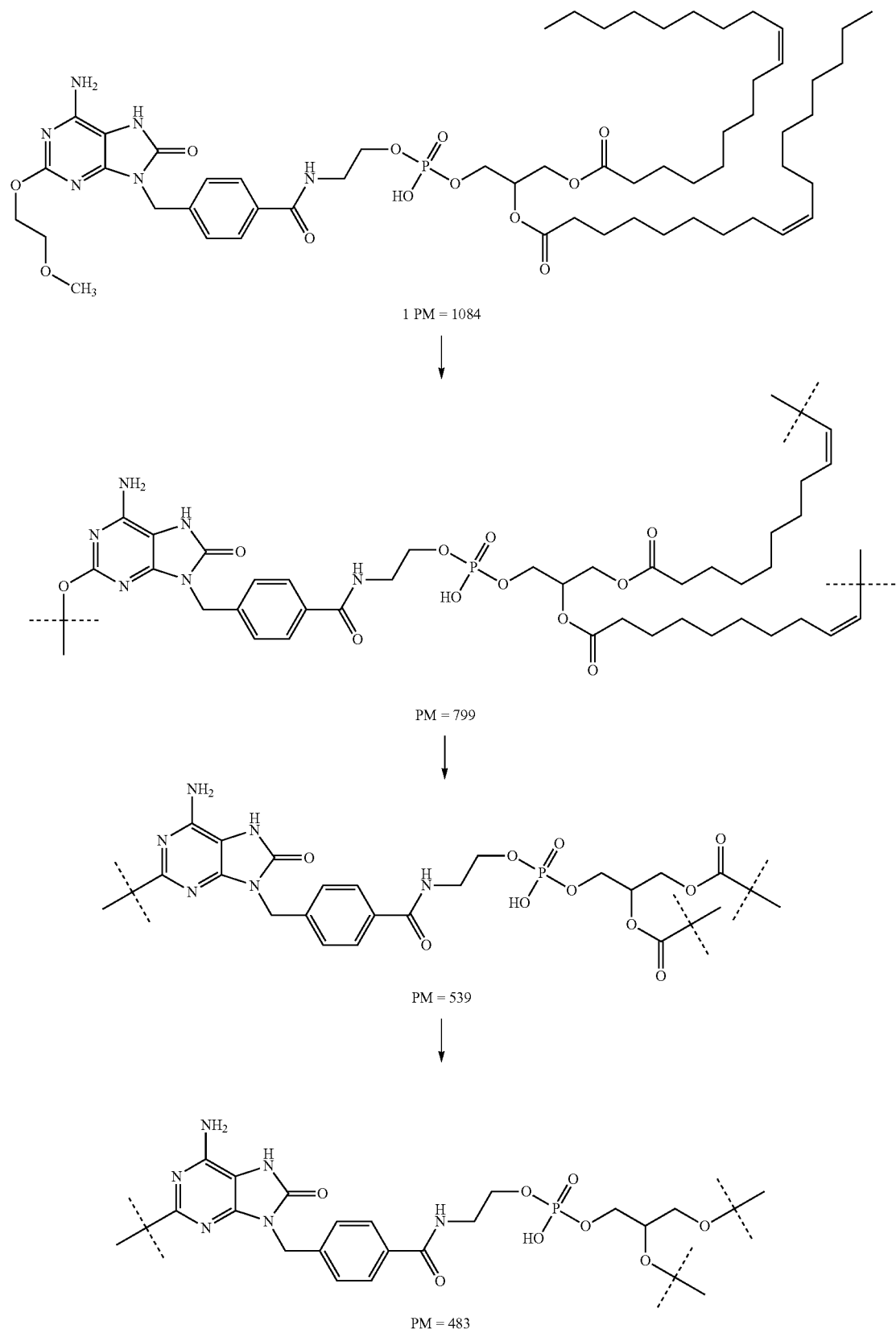

X-Ray Diffraction (XRD)

It was determined the sample of compound A was amorphous.

Dry Weight and Chemical Composition (CHN)

The experimental values were in accordance with the structure of compound A.

Optical Rotation

Sample preparation: 20 mg of compound A was dissolved in chloroform and analysed. $[\alpha]D=-37.08$ (deviation on the analysis: 43%). It was determined the high value of the deviation was likely due to the opalescent behavior of the solution.

The analysis was repeated dissolving 5 mg of compound A in chloroform. It was found $[\alpha]D=-8.7$ (deviation on the analysis: 16%).

Solubility

The method reported in the European Pharmacopoeia 6.0 was used.

Compound A was not soluble in water.
Compound A was not soluble in acetonitrile.
Compound A was soluble in chloroform (100 mg/mL).
Compound A was soluble in DMSO.

The solubility of compound A in DMSO was determined using three different batches of product:
CH730/16/8c (HPLC purity 59%)
CH730/16/8g (HPLC purity 71.5%)
CH730/23/8e (HPLC purity 95.6%)

Batch CH730/16/8g was tested according to the method described in E.Ph: DMSO was added in 0.1 mL portions to 103.7 mg of product and the suspension was shaken with a Vortex instrument for 3 min after each addition. It was found that the solubility of compound A batch Ch730/16/8g in DMSO was 259 mg/mL. The batches CH730/16/8c, CH730/16/8g and CH730/23/8e were then tested stirring each suspension for a longer time; 100 mg of each batch dissolved completely in 0.2 mL of DMSO after stirring for 30 minutes. According to this method, the solubility of compound A in DMSO was 500 mg/mL.

Stability of Compound A

Some samples of compound A were retested by HPLC and it was found that their purity diminished in few days. The results are reported in Table A below:

TABLE A

| Sample: CH730/16/8c | Test date: 20/05/09 Purity: 89.6% Report HPLC n.#0045 | Retest date: 12/06/09 Purity: 67.2% Report HPLC n. #0065 | Retest date: 17/06/09 Purity: 58.9% Report HPLC n. #0102 |
|---|---|---|---|
| Sample: CH730/16/8g | Test date: 11/06/09 Purity: 81.4% Report HPLC n. #0062 | Retest date: 18/06/09 Purity: 71.5% Report HPLC n. #0103 | |
| Sample: CH730/22/8 | Test date: 10/06/09 Purity: 57.5% Report HPLC n. #0060 | Retest date: 16/06/09 Purity: 44.8% HPLC report n. #0093 | |

The samples which underwent degradation had been stored in a crystallization vessel at room temperature under natural light. Two main impurities at RRT 1.1 and RRT 1.2 were always present. As a consequence, it was determined that compound A was not a stable compound at room temperature and/or in the presence of light. At this point, a stability study was conducted on batch CH730/16/8g. The following conditions of storage were tested:

- solid at room temperature (about 25° C.) and in presence of light
- solid at external temperature (28-35° C.) under the sun-light
- solid at +4° C.
- solution in chloroform at room temperature and in presence of light
- solution in chloroform at +4° C.
- solution in chloroform at external temperature (28-35° C.) under the sun-light The results obtained are reported in Table B hereafter.

TABLE B

Stability of CH730/16/8G

| Samples | Conditions of storage | t = 0 | t = 1 day | t = 2 days | t = 5 days | t = 6 days | t = 7 days | t = 11 days |
|---|---|---|---|---|---|---|---|---|
| CH730/16/8G | Solution in CHCl$_3$, RT and light | RRT = 1: 81.4% RRT = 1.11: 8.6% RRT = 1.23: 4.2% (Report no #62) | RRT = 1: 80.9% RRT = 1.11: 8.7% RRT = 1.24: 4.4% (Report no #70) | / | RRT = 1: 79.3% RRT = 1.10: 9.9% RRT = 1.24: 4.2% (Report no #96) | / | RRT = 1: 80.5% RRT = 1.11: 8.7% RRT = 1.27: 3.9% (Report no #107) | RRT = 1: 82.0% RRT = 1.16: 6.9% RRT = 1.29: 3.7% (Report no #111) |
| | Solution in CHCl$_3$, external T | | RRT = 1: 80.3% RRT = 1.11: | / | / | / | / | / |

TABLE B-continued

Stability of CH730/16/8G

| Samples | Conditions of storage | t = 0 | t = 1 day | t = 2 days | t = 5 days | t = 6 days | t = 7 days | t = 11 days |
|---|---|---|---|---|---|---|---|---|
| | and light | | 8.0% RRT = 1.27: 3.2% (Report no #108) | | | | | |
| | Solution in CHCl$_3$, T about 30° C. without light | RRT = 1: 80.7% RRT = 1.11: 8.6% RRT = 1.27: 3.8% (Report no #109) | / | / | / | / | / | / |
| | Solid, external T and light | / | | RRT = 1: 37.6% RRT = 1.06: 9.2% RRT = 1.11: 27.9% RRT = 1.26: 14.8% (Report no #106) | / | RRT = 1: 35.4% RRT = 1.06: 17.8% RRT = 1.14: 7.2% RRT = 1.17: 12.6% RRT = 1.28: 5.5% (Report no #112) | / | / |

The solid samples were almost completely degraded after few days. Compound A appeared more stable in solution. Because the sample of compound A batch CH730/16/8g had a low purity at t=0, the stability study was repeated on a freshly prepared sample, batch CH730/23/8e. The results obtained are reported in Table C hereafter.

TABLE C

Stability of CH730/23/8E

| Sample | Conditions of storage | t = 0 | t = 2 days | t = 5 days | t = 7 days | t = 20 days |
|---|---|---|---|---|---|---|
| CH730/23/8E | Solution in CHCl$_3$, room temperature and light | RRT = 1: 95.6% RRT = 1.24: 0.9% RRT = 1.28: 1.3% (Report no 91) | RRT = 1: 95.5% RRT = 1.24: 0.9% RRT = 1.28: 1.3% (Report no 92) | RRT = 1: 95.4% RRT = 1.23: 1.0% RRT = 1.29: 1.2% (Report no 98) | RRT = 1: 95.5% RRT = 1.23: 1.1% RRT = 1.28: 1.2% (Report no 104) | RRT = 1: 94.4% RRT = 1.19: 1.2% RRT = 1.26: 1.5% (Report no 113) |
| | Solution in CHCl$_3$, +4° C. | | RRT = 1: 95.3% RRT = 1.24: 1.0% RRT = 1.27: 1.4% (Report no 93) | RRT = 1: 95.3% RRT = 1.23: 1.1% RRT = 1.28: 1.3% (Report no 99) | RRT = 1: 95.2% RRT = 1.23: 1.1% RRT = 1.28: 1.3% (Report no 105) | RRT = 1: 93.9% RRT = 1.18: 1.4% RRT = 1.25: 1.4% (Report no 116) |
| | Solution in CHCl$_3$, external temperature and light | | RRT = 1: 94.2% RRT = 1.27: 1.2% (Report no 94) | RRT = 1: 90.2% RRT = 1.13: 2.7% RRT = 1.27: 1.2% (Report no 100) | RRT = 1: 89.0% RRT = 1.14: 2.5% RRT = 1.28: 1.1% (Report no 106) | RRT = 1: 55.6% RRT = 1.08: 6.8% RRT = 1.16: 1.6% (Report no 117) |
| | Solid, room temperature and light | | RRT = 1: 94.6% RRT = 1.24: 1.3% RRT = 1.27: 2.1% (Report no 95) | RRT = 1: 91.7% RRT = 1.22: 1.7% RRT = 1.27: 3.8% (Report no 101) | RRT = 1: 91.8% RRT = 1.21: 2.3% RRT = 1.27: 3.8% (Report no 107) | RRT = 1: 68.5% RRT = 1.08: 14.5% RRT = 1.18: 3.9% RRT = 1.24: 6.7% (Report no 118) |

TABLE C-continued

Stability of CH730/23/8E

| Sample | Conditions of storage | t = 0 | t = 2 days | t = 5 days | t = 7 days | t = 20 days |
|---|---|---|---|---|---|---|
| | Solid, +4° C. | | RRT = 1: 95.6% RRT = 1.24: 0.8% RRT = 1.27: 1.3% (Report no 96) | RRT = 1: 94.7% RRT = 1.23: 1.2% RRT = 1.28: 1.6% (Report no 102) | RRT = 1: 94.9% RRT = 1.22: 1.4% RRT = 1.28: 1.5% (Report no 108) | RRT = 1: 90.4% RRT = 1.18: 3.1% RRT = 1.25: 3.4% (Report no 119) |
| | Solid, external temperature and light | | RRT = 1: 94.1% RRT = 1.27: 3.6% (Report no 97) | RRT = 1: 92.0% RRT = 1.27: 4.9% (Report no 103) | RRT = 1: 92.0% RRT = 1.27: 5.7% (Report no 109) | RRT = 1: 43.8% RRT = 1.09: 27.2% RRT = 1.18: 9.0% RRT = 1.23: 12.1% (Report no 120) |

HPLC analysis confirmed that compound A undergoes a rapid degradation at T>25° C. and in the presence of light. It was demonstrated that the compound was more stable in solution.

HPLC-MS Analysis on a Stressed Sample of Compound A.

The sample of compound A batch CH730/16/8g, stored for six days at external temperature (28-35° C.; HPLC purity 35.4%; report n. #0112) under sun light, was analyzed by HPLC-MS and compared with freshly prepared batch CH730/23/8e. The aim of this study was to demonstrate that the impurities detected by HPLC during the stability study were not an analytical artifact, but they were really formed by the action of heat and light.

| PLC method | |
|---|---|
| Instrument | Agilent 1100 |
| Column | C18 XTERRA 2.1 × 150 mm, 3.5 m |
| T (° C.) | 50° C. |
| lambda nm) | 220 and 280 |
| Flow (ml/min) | 0.15 |
| Analysis time (min) | 40 |
| Mobile phase | A: methanol:isopropanol:water 50:20:30 + 0.1% formic acid |
| | B: methanol:isopropanol 50:50 + 0.1% formic acid |
| Elution | Gradient |
| | T (min) | %A | %B |
| Gradient | 0 | 100 | 0 |
| | 5 | 100 | 0 |
| | 30 | 0 | 100 |
| | 40 | 0 | 100 |
| Retention time (min) | Compound A about 33 | | |

Sample Preparation

Solution a: the sample was dissolved in dimethylsulfoxide-isopropanol 20:80 in order to have a concentration of 2 mg/ml Solution b: "solution a" was diluted 1:5 with methanol:isopropanol:water 50:20:30+0.1% formic acid

Example 2

Synthesis of SC12

Described hereafter is preparation of (2-(4-((6-amino-2-(2-methoxyethoxy)-8-oxo-7H-purin-9(8H)-yl)methyl)benzamido)ethyl 2,3-bis(oleoyloxy)propyl phosphate).

The HPLC-MS analysis carried out on compound A batch CH730/16/8g demonstrated that the main impurity formed by the degradation of the compound was the oxidated derivative. Acid 7 (compound 7) was conjugated with 1,2-dilauroyl-sn-glycero-3-phosphoethanolamine (DLPE) and its stability was studied. The product is referred to as SC12. Compounds SC8 and SC18 were synthesized in a similar manner, except that compound 7 was conjugated with 1,2-dioctanoyl-sn-glycero-3-phosphoethanolamine or 1,2-distrearoyl-sn-glycero-3-phosphoethanolamine, respectively, instead of with DLPE.

A. Preparation of SC12

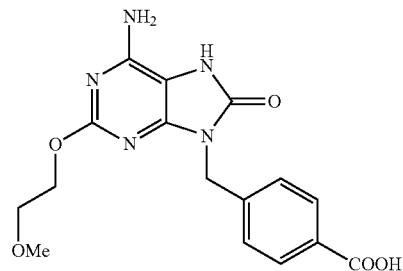

7

↓ 1,2-dilauroyl-sn-glycero-3-phosphoethanolamine

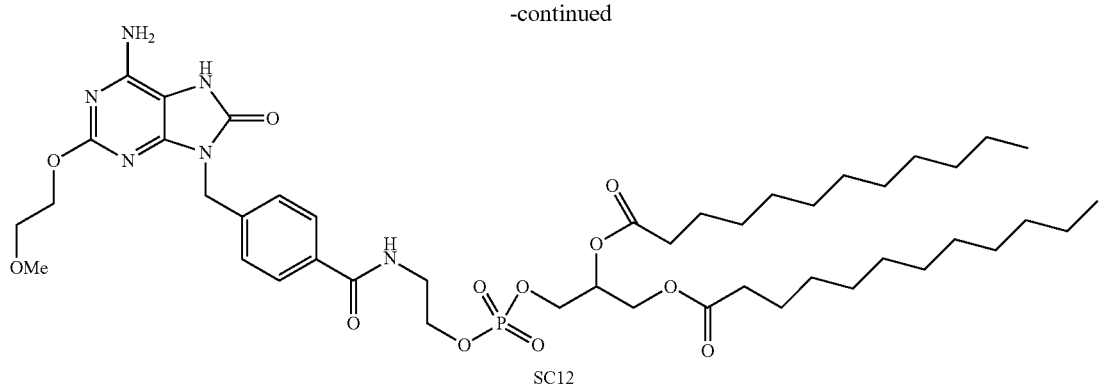

SC12

In this example of a method of preparing SC12, Acid 7 (compound 7) (batch CH730/18/6d; 1 g, 0.0028 mol) is dissolved in a mixture of acetonitrile (6 mL) and DMSO (6 mL) at room temperature and under Argon atmosphere. Carbonyl diimidazole (455 mg, 0.0028 mol, 1 eqv.) is added and the resulting solution is stirred for 1 hr. A solution of DLPE (>99%; 1.78 g, 0.0028 mol, 1 eqv.) in dry dichloromethane was added drop wise. The reaction mixture is stirred for 16 hrs, till complete conversion of the reagents. Acetonitrile is removed by distillation in vacuum; water (200 mL) is added to the residue; a white solid separated. The solid is filtered on a Buchner funnel and washed with methanol (5 mL). After drying in vacuum at 35° C., SC12 is obtained as a white solid; 1.8 g, Y 65%, HPLC purity 90.3%, HPLC report n. 0121.

B. Analytical Characterization of SC12

The structure of SC12 was confirmed by $^1$H-NMR, $^{13}$C-NMR and MS.

C. Stability of SC12

A stability study was performed on SC12 and the following conditions were tested:
  solution in chloroform at room temperature (about 25° C.) and in presence of light.
  solid at room temperature and in presence of light.
  solid at external temperature (28-35° C.) under the sun light.
The samples were analyzed at t=0 and after 20 days.
The results are reported in Table 1 below, and the main impurities formed with their RRT are listed.

TABLE 1

| Samples | Conditions of storage | t = 0 | t = 20 days |
|---|---|---|---|
| CH730/2/13 | Solution in CHCl$_3$, RT and light | RRT = 1: 90.3% RRT = 0.46: 5.7% RRT = 1.21: 0.9% (Report n° 0121) | RRT = 1: 88.0% RRT = 0.88: 6.2% RRT = 1.21: 5.0% (Report n° 0139) |
|  | Solid, external T and light |  | RRT = 1: 84.0% RRT = 0.88: 6.6% RRT = 1.21: 7.1% (Report n° 0141) |
|  | Solid, RT and light |  | RRT = 1: 87.8% RRT = 0.88: 6.2% RRT = 1.21: 4.8% (Report n° 0141) |

The data obtained show that SC12 was more stable than compound A. Furthermore, Table 2 shows the comparison between the stability of compound A and SC12 with respect to heat. Solid samples of each compound were maintained at 80° C. and analyzed by HPLC.

TABLE 2

| Sample | t = 0 | After 2 hrs at 80° C. | After 22 hrs at 80° C. |
|---|---|---|---|
| Compound A | 95% HPLC | 73% HPLC | / |
| SC12 | 90% HPLC | 90% HPLC | 88% HPLC |

Example 3

Potency of Compounds

The potency of five samples with TLR7 agonist activity in a PBMC model and in the mouse macrophage cell line Raw264.7 was determined by measuring the dose-dependent stimulation of the pro-inflammatory cytokines IL-6 and TNF-alpha.

Methods and Experimental Setup
  The study was setup in two models as outlined below:
    Model 1: Five TLR7 agonists were tested in the mouse macrophage cell line model Raw264.7. Endpoints were measurement of IL-6 and TNF-alpha.
    Model 2: Five TLR7 agonists were tested for potency in a PBMC model. End-points were measurement of secreted IL-6 and TNF-alpha.
  Model 1
    The potency of 5 TLR agonists was assessed in comparison with a positive control (Imiquimod) in a Raw264.7 cell line. EC50 values were determined for control and each drug candidate for IL-6 and TNF-alpha secretion.
    Method: Raw264.7 cells were grown according to conditions from the supplier using RPMI media and 10% FCS. The cells were plated in 96 well plates and treated with TLR7 agonists for 24 hours in 7 doses. The conditioned media was removed after 24 hours for ELISA analyses. The cells were subsequently assayed for viability using the XTT assay according to the guidelines from the supplier.
    Experimental Setup:
      1. Untreated cells
      2. Imiquimod
      3. TLR7 agonist 1
      4. TLR7 agonist 2
      5. TLR7 agonist 3
      6. TLR7 agonist 4
      7. TLR7 agonist 5

Compounds were tested in 7 doses (0,003-0,01,03-0,1-0, 5-2,0-10,0 micromolar). The experiment was performed in quadruplicate wells for each testing series, and the supernatant pooled and measured by ELISA in triplicates.

Model 2

The potency of the 5 TLR agonists was assessed based on the ability to stimulate IL-6 and TNF-alpha secretion, and potency was compared with a positive control (Imiquimod) in a PBMC model. EC50 values were determined for control and each drug candidate for IL-6 and TNF-alpha secretion.

Method: PBMCs were purified from three donors and plated into 96 well plates at $2 \times 10^5$ cells/well in RPMI media including human 2% heat inactivated AB serum, glutamine, Pen-strep and beta-mercaptoethanol. The cells were treated with TLR7 agonists for 24 hours in 7 doses. The conditioned media was removed for ELISA analyses for IL-6 and TNF-alpha, and cell survival determined by the XTT method according to the protocol from the supplier.

Experimental Setup:
1. Untreated cells
2. Imiquimod
3. TLR7 agonist 1
4. TLR7 agonist 2
5. TLR7 agonist 3
6. TLR7 agonist 4
7. TLR7 agonist 5

Compounds were tested in 7 doses (0,003-0,01,03-0,1-0, 5-2,0-10,0 micromolar).

Data Handling:
Concentrations of IL-6 and TNF-alpha were determined by ELISA from R&D Systems using the Microsoft Excel Software. The results were analyzed in Graph Pad Prism in order to prepare dose-response curves, and for determination of EC50 values.

Statistical Analyses:
Due to the number of donors, statistical evaluation between individual EC50 values was not relevant.

Figure 2:
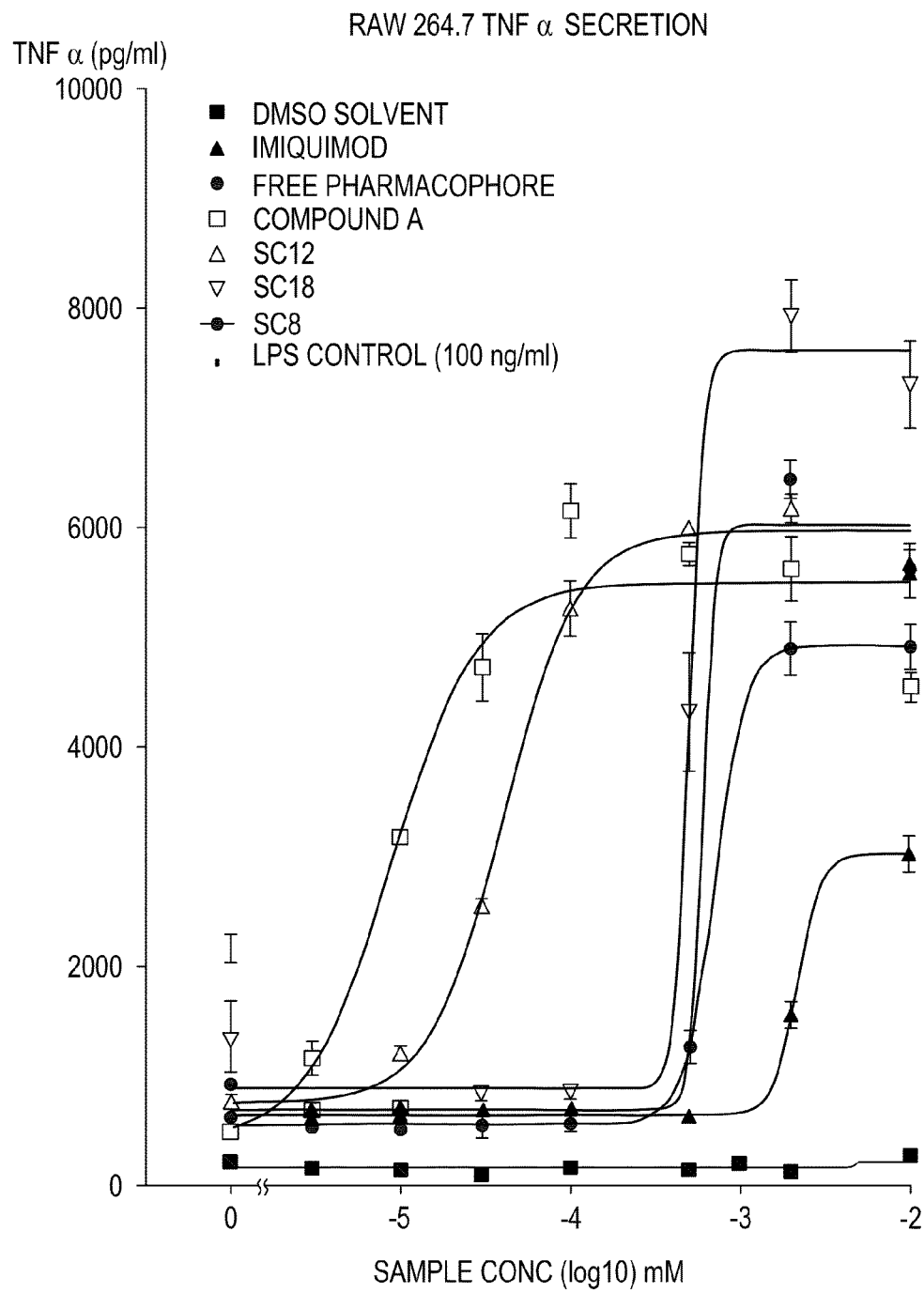
FIG. 2 illustrates cytokine production for compounds in Raw264.7 mouse macrophage cell line studies.

Results and Discussion:
In Model 1, IL-6 and TNF-alpha secretions were induced dose-dependently by all compounds, but not by DMSO by itself (FIGS. 1-2). The compounds reached different levels of maximum cytokine levels, and also showed different EC50 values. The order of potency was as follows, with the most potent first: compound A <SC12<SC18<SC8=free pharmacophore<Imiquimod (Table 3). Free pharmacophore ("free ph") has the structure:

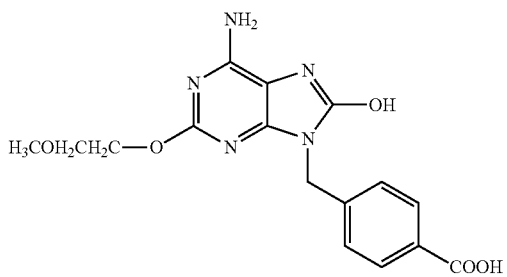

Figure 3A:
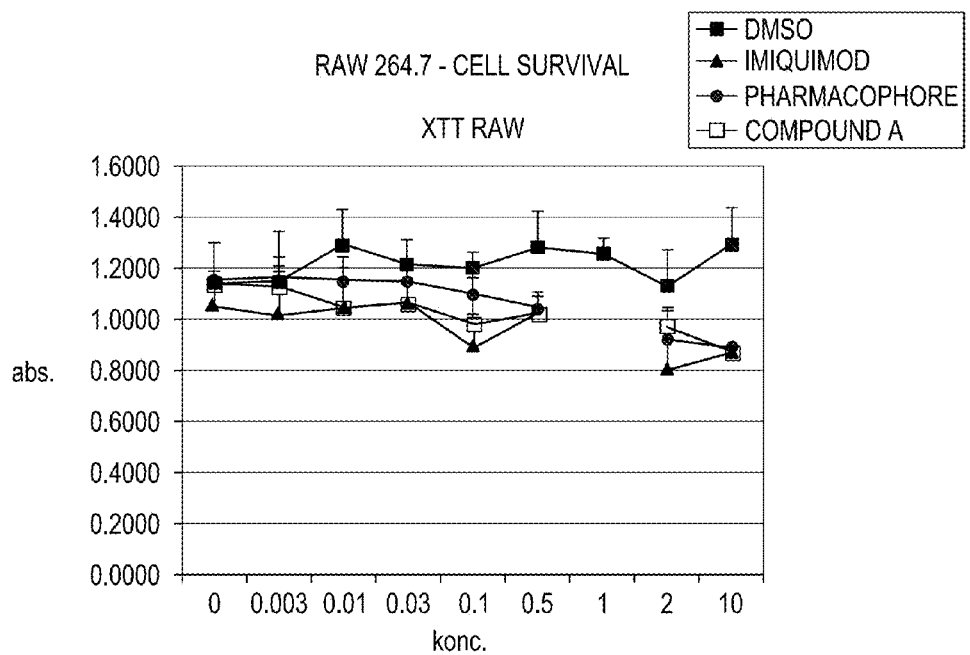
FIGS. 3A and 3B show survival data for Raw264.7 mouse macrophage cell line studies.
Figure 3B:
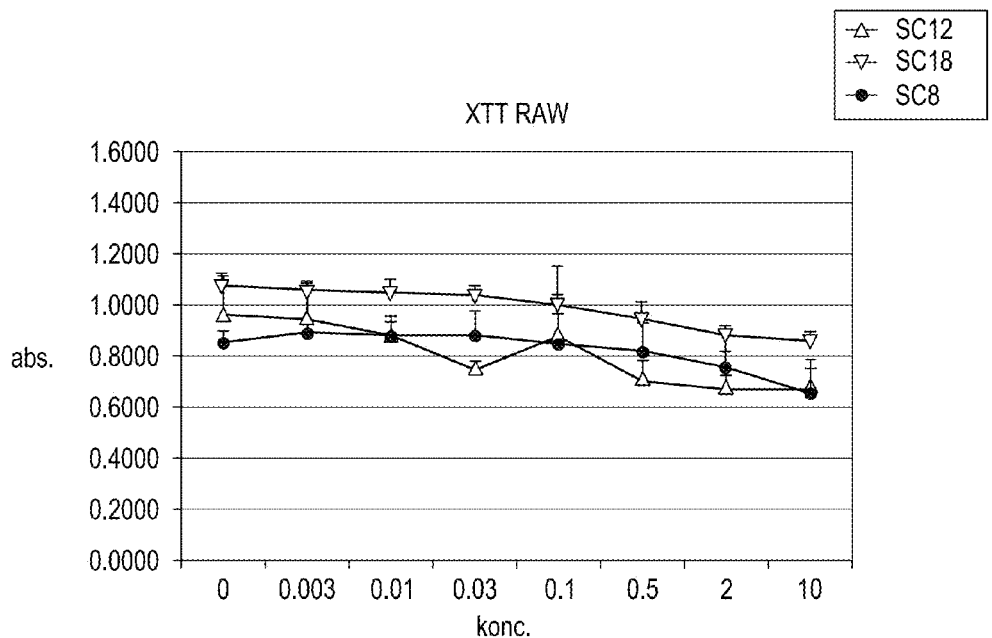
Figure 4:
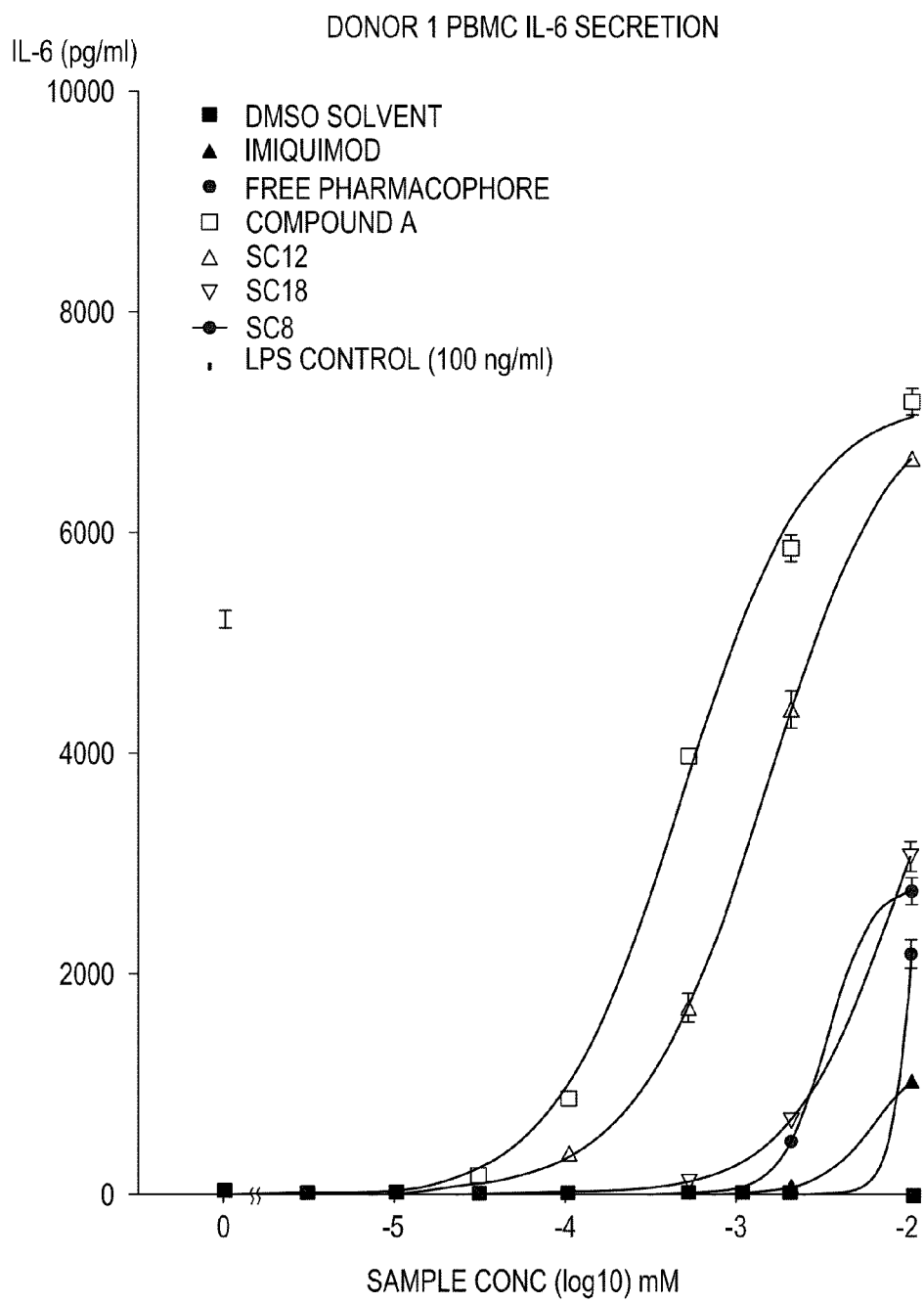
FIG. 4 is a graph of IL-6 production for compounds in PBMC studies for Donor 1.

The XTT assay (FIG. 3, where the Y-axis=relative survival, the x-axis=concentration for treatment) showed that the cells were slightly affected by the higher concentrations of compounds, which for some compounds was reflected in a decreased cytokine production at the highest concentrations (in particular for compound A, SC12 and SC18; FIGS. 1 and 2). Since the maximum plateau of the dose-response curves was determined based on the cytokine levels induced by the highest concentrations, this plateau could be slightly increased if the highest concentration of the compounds was not considered. However, the doses in the dynamic range would not be affected by this, which means that the EC50 values would be minimally affected.

TABLE 3

EC50 values determined in the Raw264.7 cell line on the basis of the 7 doses tested of each compound.

| Raw 264.7 | Imiquimod | Free ph | Compound A | SC12 | SC18 | SC8 |
|---|---|---|---|---|---|---|
| EC 50 IL 6 mM | 2.005 | 0.531 | 0.006 | 0.042 | 0.310 | 0.669 |
| EC 50 TNF-alpha | 2.156 | 0.707 | 0.009 | 0.041 | 0.499 | 0.603 |

In conclusion for Model 1, compound A was the most potent TLR7 agonist, followed by SC12, SC18, SC8 together with free pharmacophore and finally Imiquimod. In this respect, all 5 compounds were more potent than Imiquimod in this model.

Figure 5:
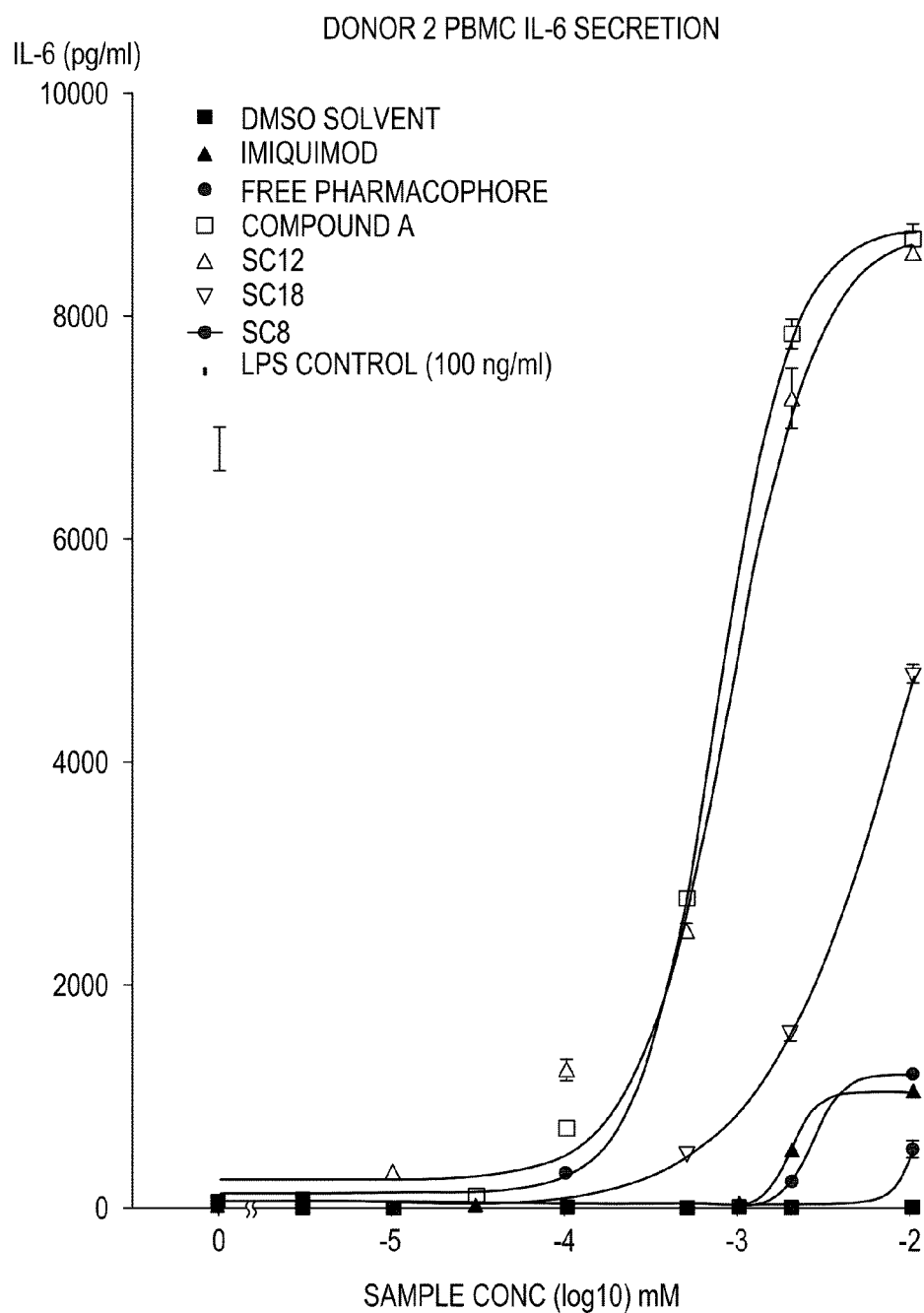
FIG. 5 is a graph of IL-6 production for compounds in PBMC studies for Donor 2.
Figure 6:
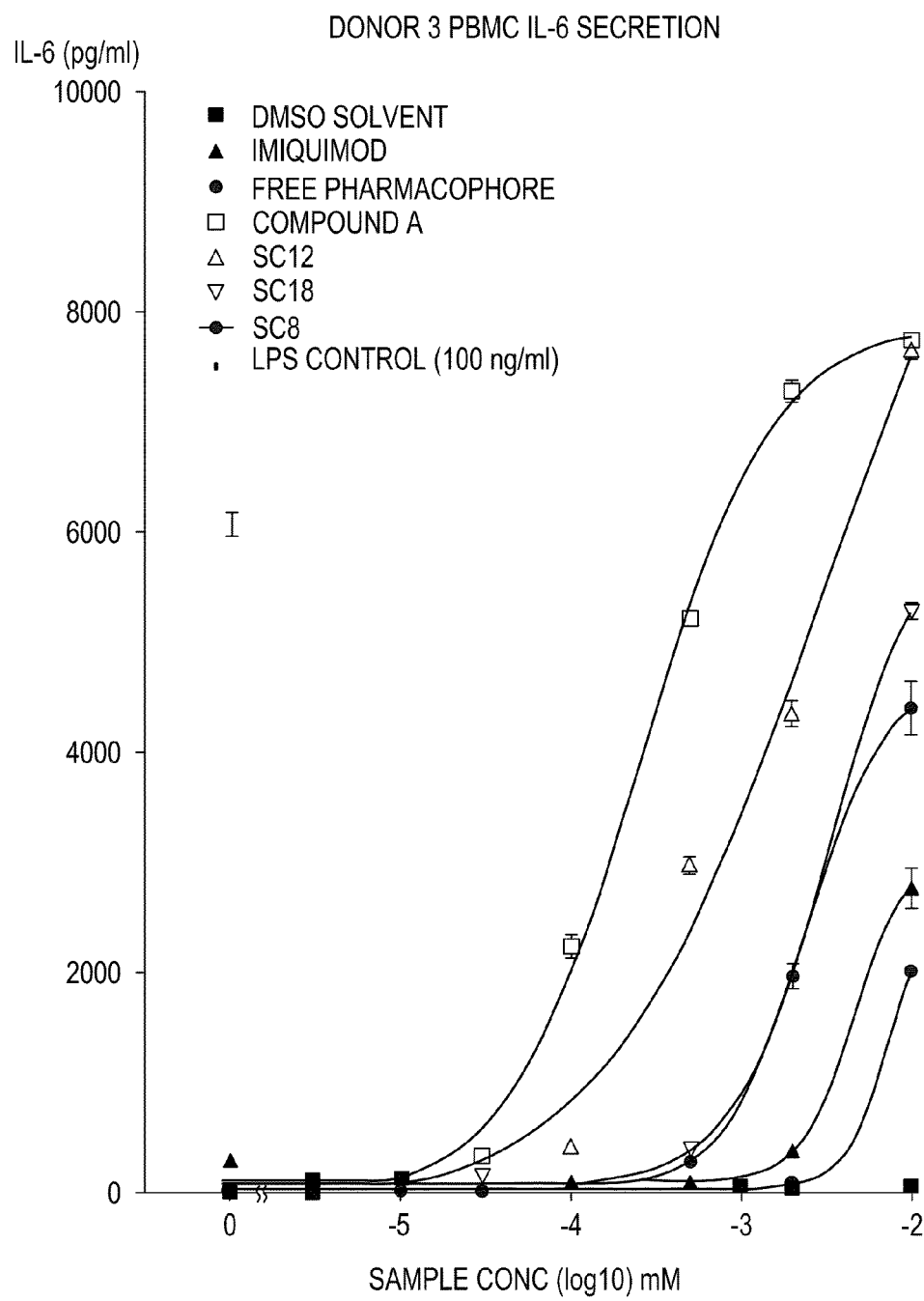
FIG. 6 is a graph of IL-6 production for compounds in PBMC studies for Donor 3.
Figure 7:
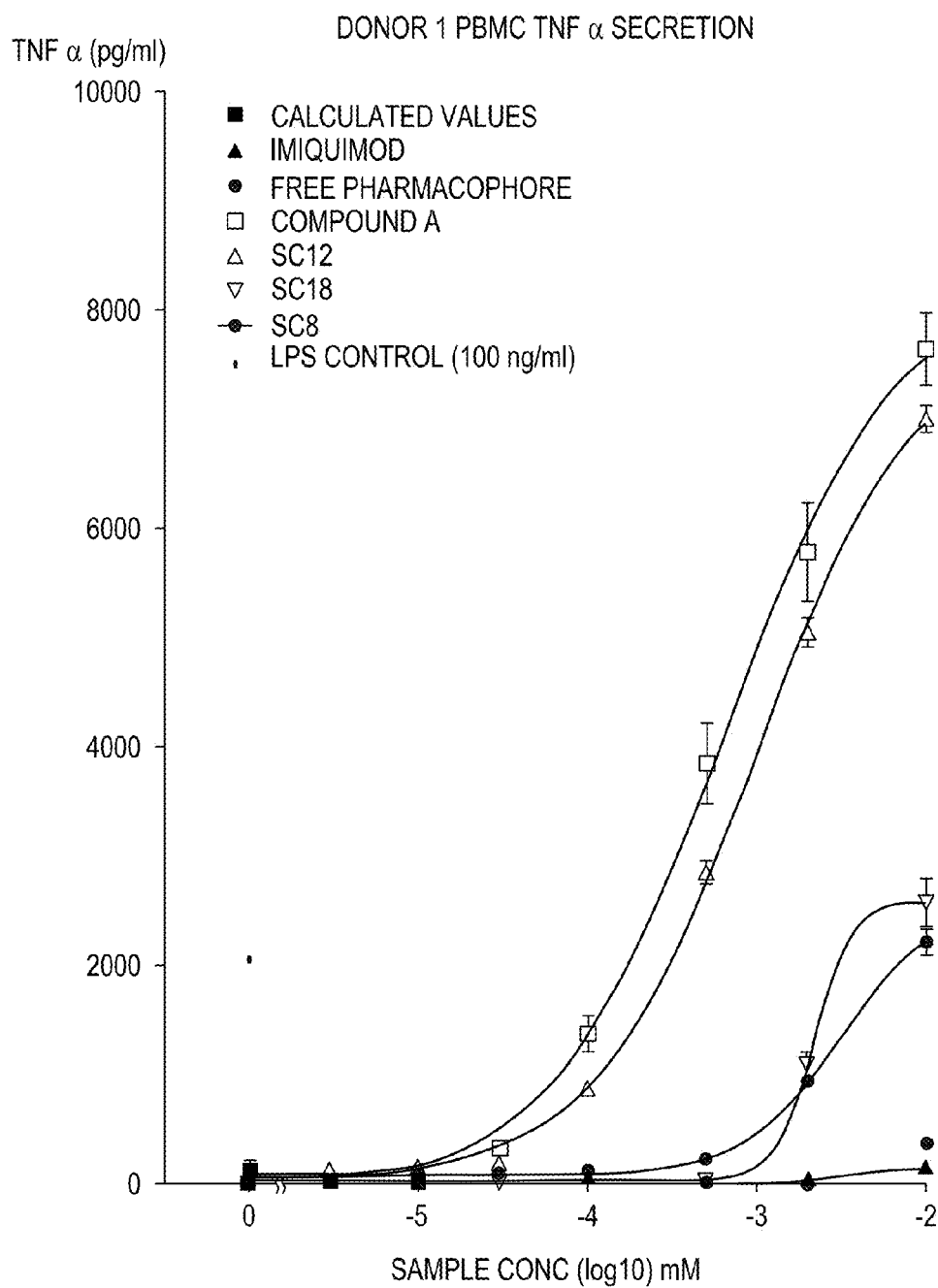
FIG. 7 is a graph of TNF-alpha production for compounds in PBMC studies for Donor 1.
Figure 8:
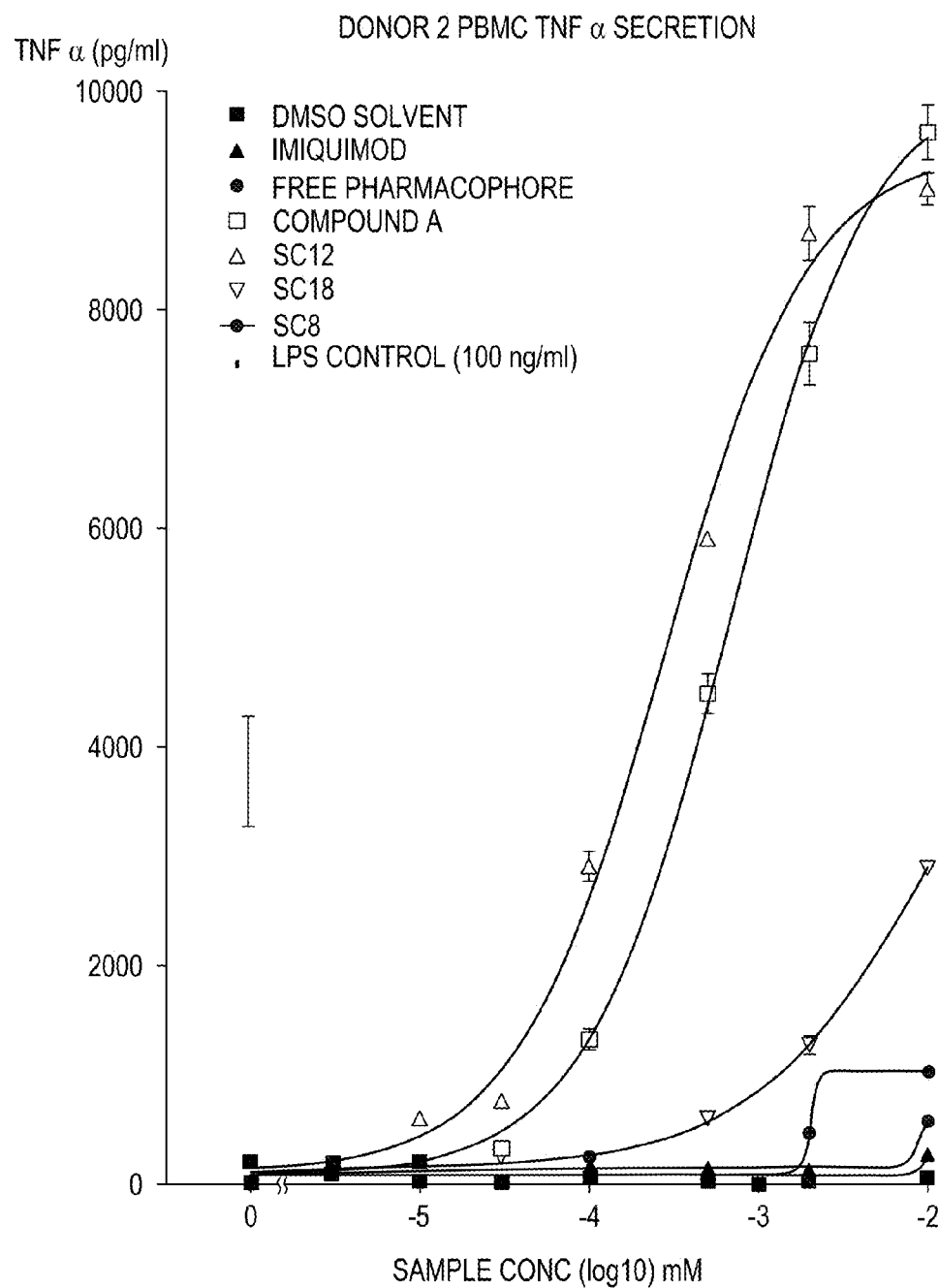
FIG. 8 is a graph of TNF-alpha production for compounds in PBMC studies for Donor 2.
Figure 9:
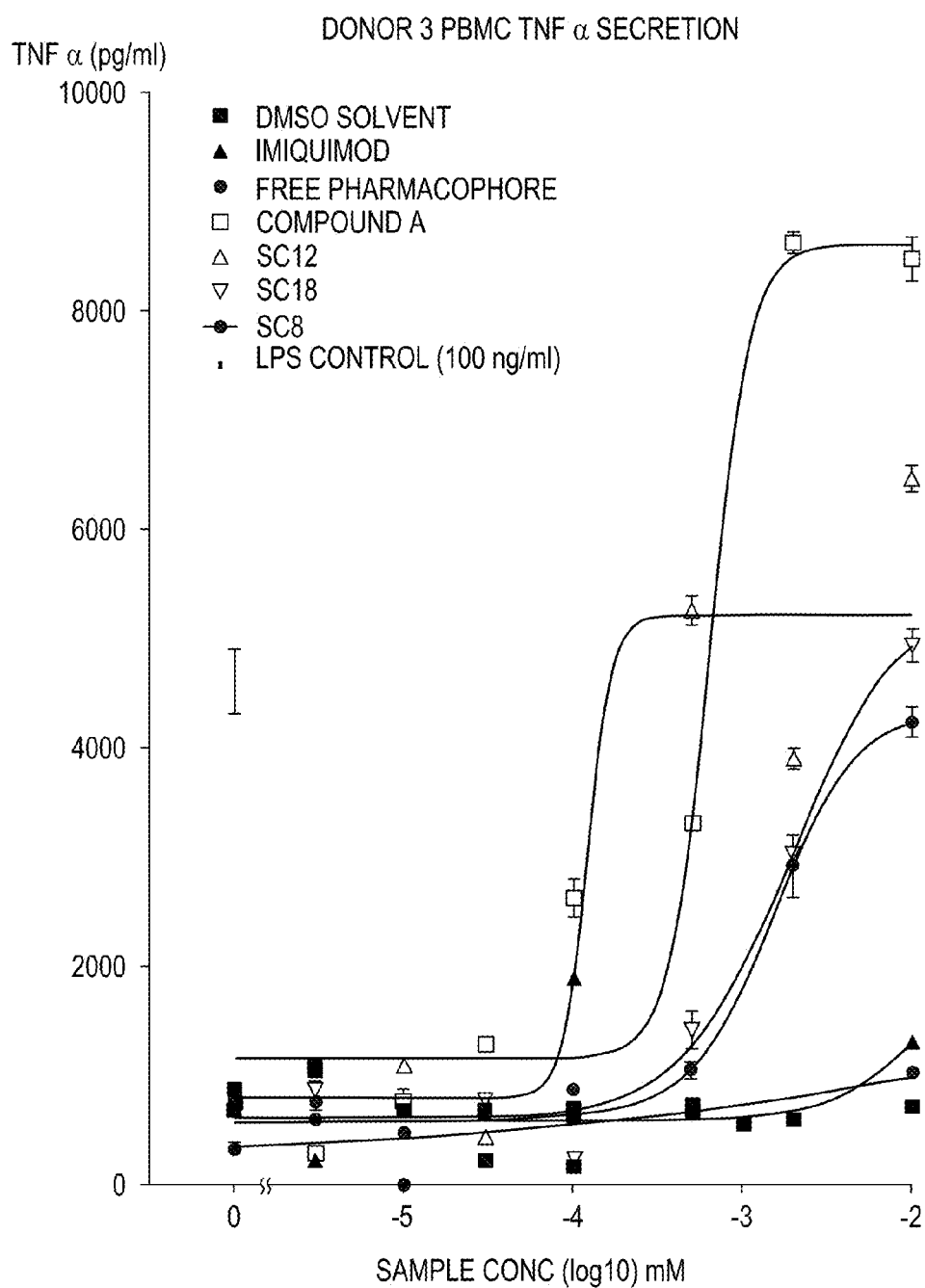
FIG. 9 is a graph of TNF-alpha production for compounds in PBMC studies for Donor 3.
Figure 10A:
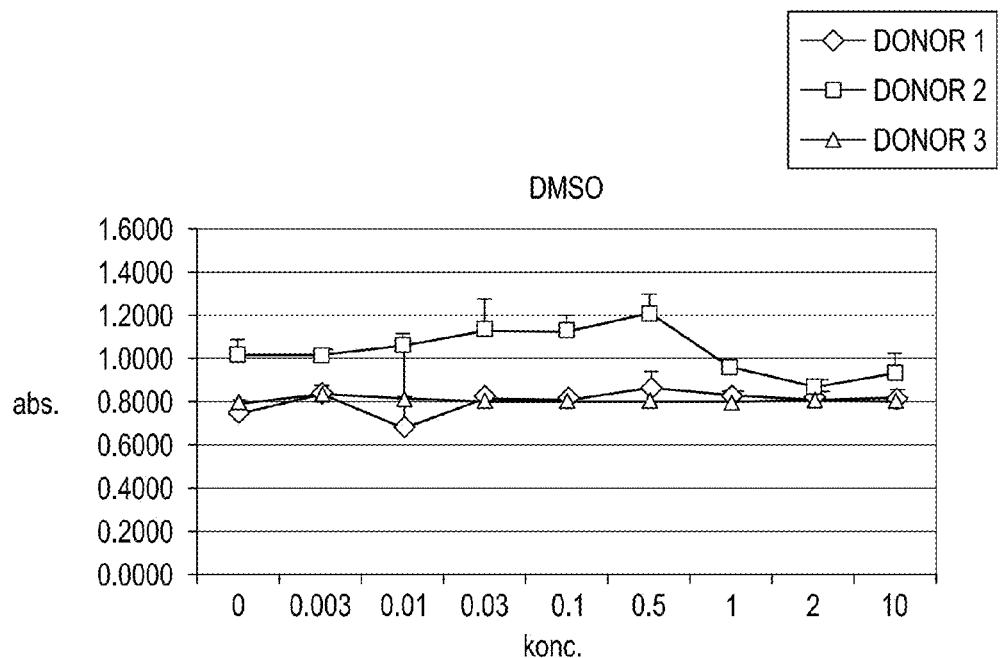
FIGS. 10A-10G provide survival data for PBMC studies.
Figure 10B:
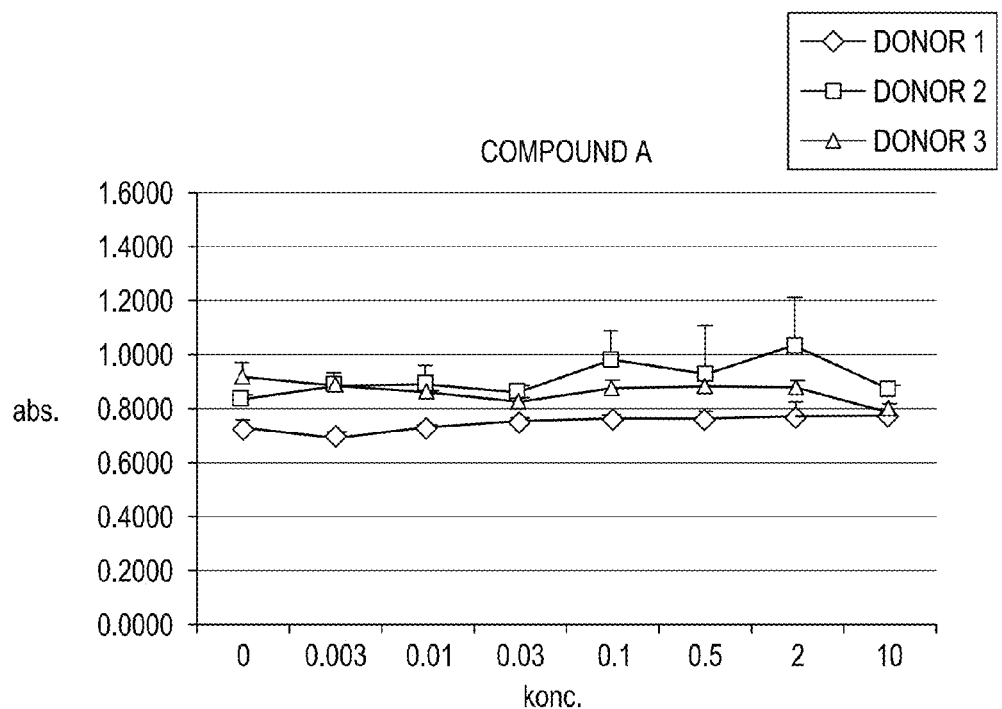
Figure 10C:
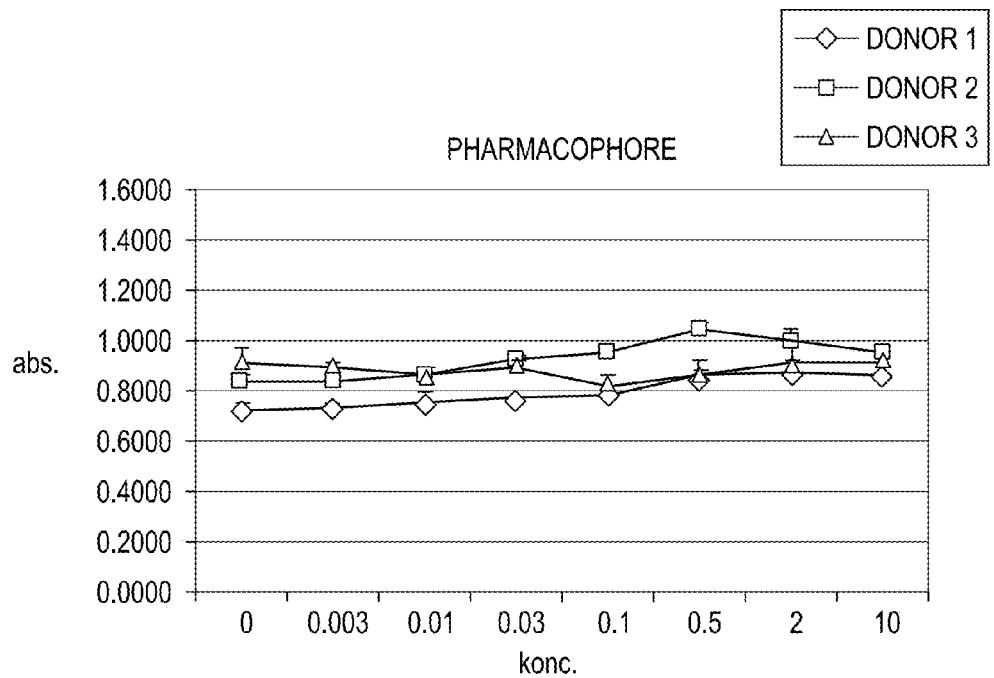
Figure 10D:
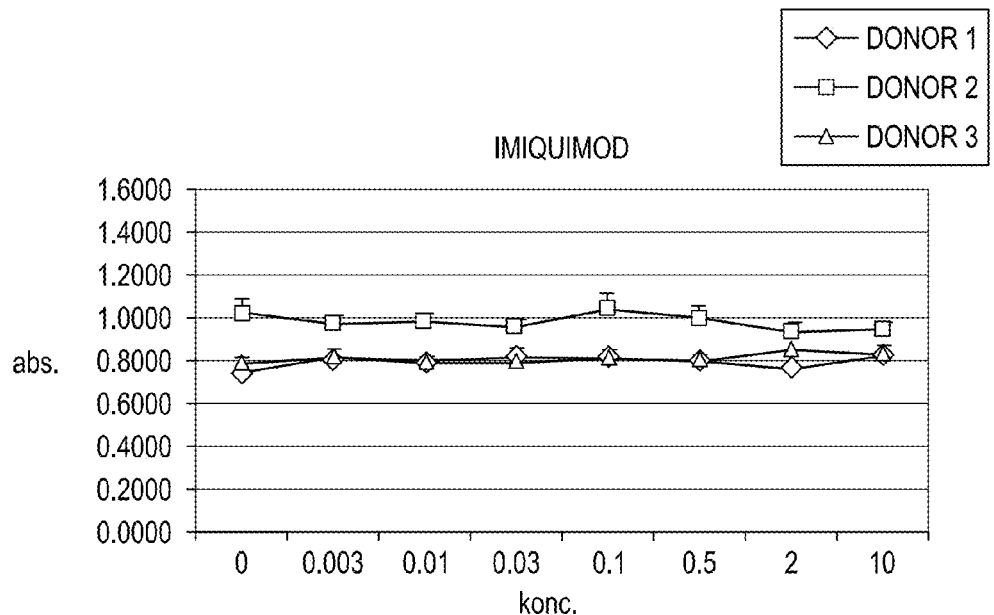
Figure 10E:
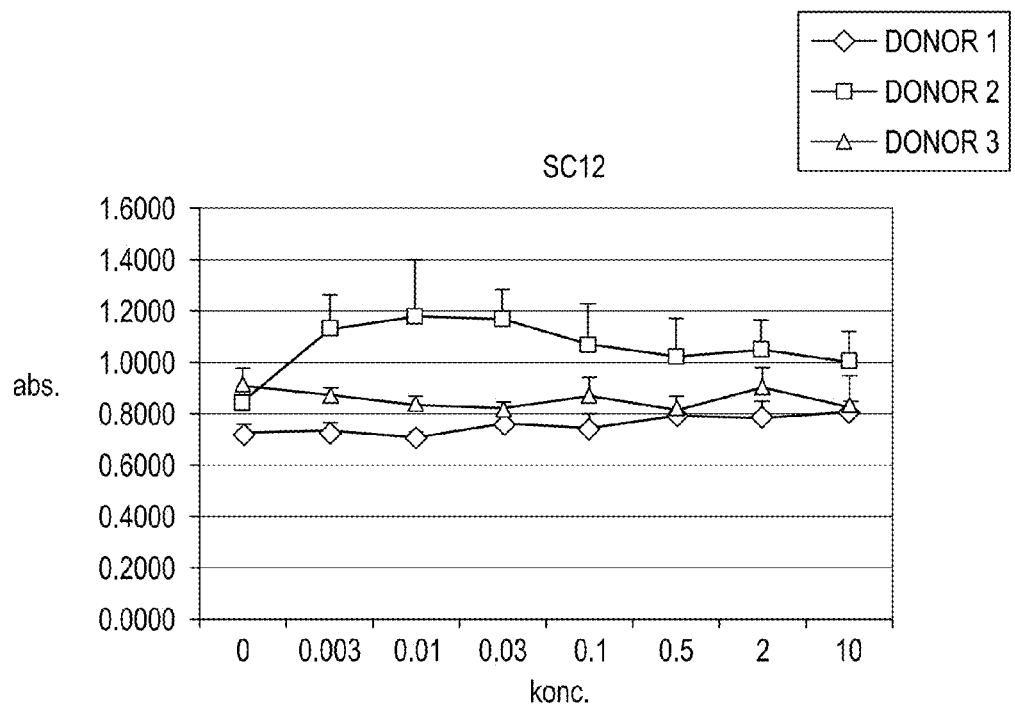
Figure 10F:
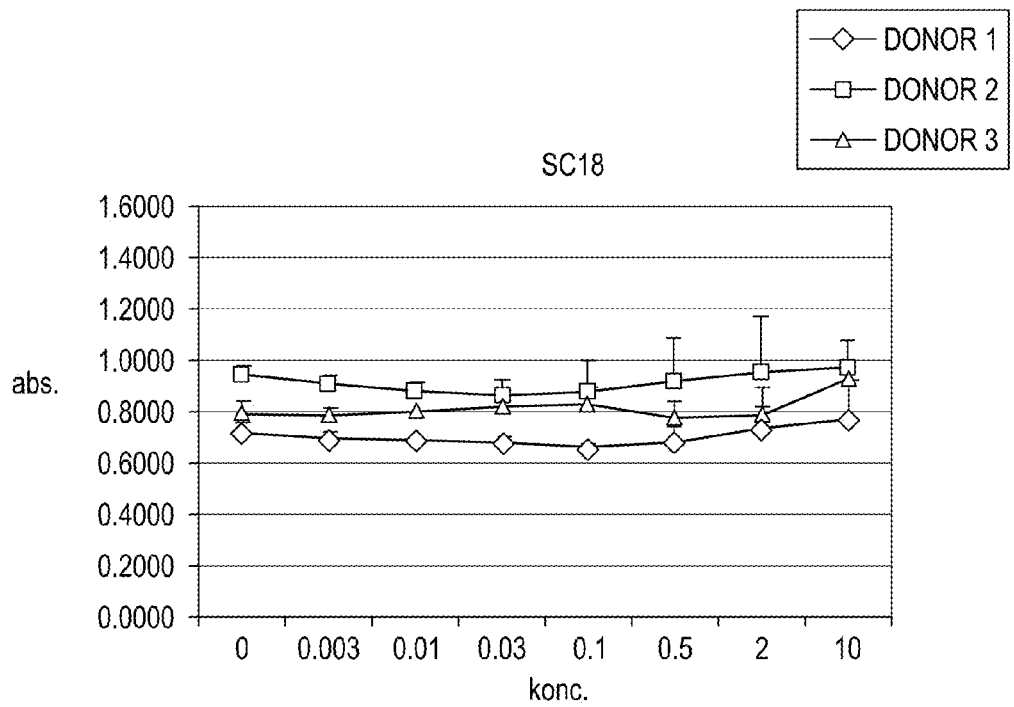
Figure 10G:
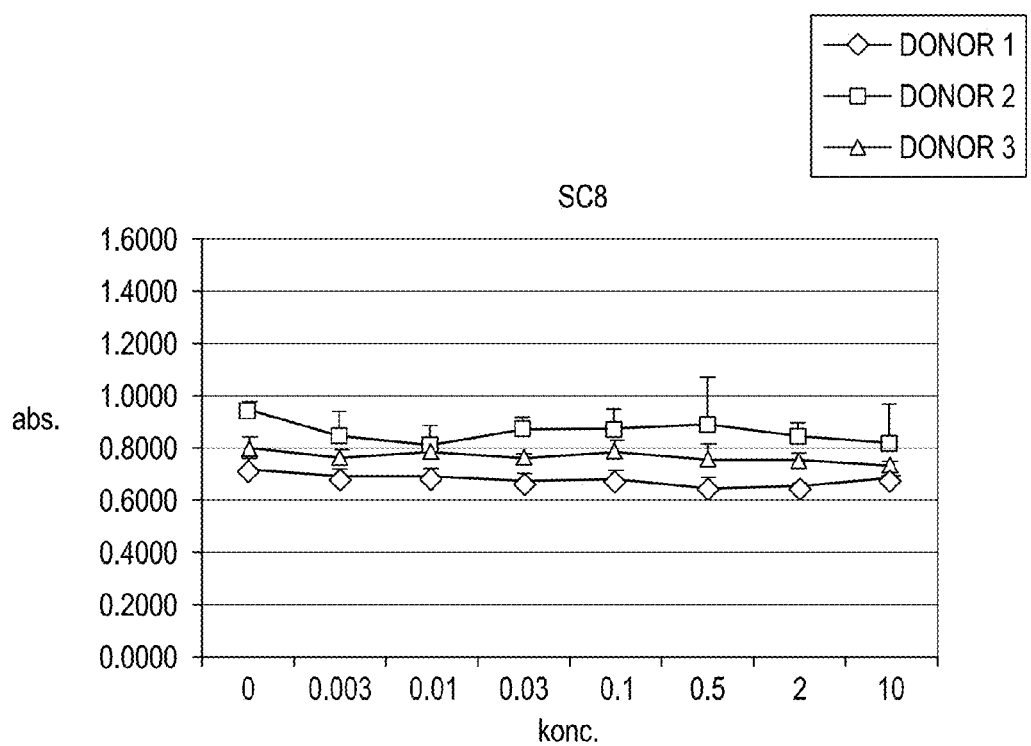

For Model 2, PBMCs were derived from buffy coats from healthy anonymous adult human donors. Both IL-6 and TNF-alpha secretions were induced dose-dependently by most compounds in the three donors. A few compounds like Imiquimod, SC8 and the free pharmacophore showed weak ability to induce the cytokines in some donors, where only the highest dose induced cytokine production. Compound A was the most potent compound for IL-6 secretion in all three donors. In donor 2, SC12 was as potent as compound A, whereas SC12 was the second most potent compound in donor 1 and 3, Table 4. On average, the compounds showed an order of potency as follows: Compound A <SC12<free pharmacophore<Imiquimod<SC18<SC8. SC8 showed levels of cytokines which did not allow a solid dose-response curve. For TNF-alpha secretion, SC12 was on average slightly more potent than compound A, based on the results from the three donors, Table 4. The order of potency was as follows: SC12<compound A <free pharmacophore<SC18<SC8<Imiquimod, FIGS. 7-9. However, the data for Imiquimod and SC8 were ambiguous, and only induced weak TNF-alpha secretion in all three donors. The survival assay showed an overall good survival of the cells throughout the study at all concentrations tested, with no obvious cytotoxicity observed. One donor, number 2, who was treated with SC12 had an increased survival response (FIG. 10) but did not reflect a difference in cytokine response (FIGS. 5 and 8).

TABLE 4

EC50 values determined in PBMCs from three donors for the 6 TLR7 agonists with indications of average potency.

| | Imiquimod | Free ph | Compound A | SC12 | SC18 | SC8 |
|---|---|---|---|---|---|---|
| IL-6 secretion | | | | | | |
| Donor 1 MC50 mM | 6.348 | 3.239 | 0.4597 | 1.439 | 7.808 | 11.02 |
| Donor 2 MC50 mM | 1.994 | 2.671 | 0.7401 | 0.8642 | 12.35 | 11.31 |
| Donor 3 MC50 mM | 4.643 | 2.443 | 0.2549 | 2.783 | 3.293 | 7.385 |

TABLE 4-continued

EC50 values determined in PBMCs from three donors for the 6 TLR7 agonists with indications of average potency.

|  | Imiquimod | Free ph | Compound A | SC12 | SC18 | SC8 |
|---|---|---|---|---|---|---|
| Average EC50 mM TNFa secretion | 4.328 | 2.784 | 0.485 | 1.696 | 7.817 | 9.905 |
| Donor 1 MC50 mM | 3.071 | 3.108 | 0.6443 | 0.9948 | 2.185 | 0 |
| Donor 2 MC50 mM | 24.94 | 2.042 | 0.6651 | 0.2754 | 1-,54 | 9.543 |
| Donor 3 MC50 mM | 22.39 | 1.544 | 0.6391 | 0.1207 | 1.958 | 0 |
| Average EC50 mM | 16.800 | 2.231 | 0.650 | 0.464 | 4.894 | 9.543 |

In conclusion for Model 2, compound A and SC12 were the most potent TLR7 agonists. Compound A was the most potent stimulator of IL-6, and SC12 was slightly more potent than compound A for TNF-alpha secretion. The other compounds showed different abilities to induce IL-6 and TNF-alpha from the PBMCs in the different donors, and their potency cannot be generally ordered. Imiquimod and SC8 showed cytokine induction in the highest concentration tested and low levels of secreted cytokine. Thus EC50 values cannot be determined for Imiquimod and SC8. SC18 and free pharmacophore showed similar responses for both IL-6 and TNF-alpha secretion, which reached higher levels than for Imiquimod and SC8 but with higher values than for the Raw264.7 model.

The Raw264.7 cell line responded to all compounds tested, with compound A being the most potent, followed by SC12. These two were followed by SC18, SC8 and free pharmacophore and showed similar potencies, with Imiquimod showing the weakest induction of IL-6 and TNF-alpha.

The PBMC experiment showed compound A and SC12 as the two most potent TLR7 agonists, followed by SC18 and free pharmacophore, but with low cytokine secretion measured after treatment with Imiquimod and SC8.

Example 4

Test for Potency of TLR7 Agonists from Two Different Batches of Compound a and SC12 in Human PBMCs Aim To determine the potency of 2 TLR7 agonists produced in two different batches in human PBMCs for induction of IL-6 secretion.

Methods and Experimental Setup

PBMCs were purified from two donors and plated into 96 well plates at $2 \times 10^5$ cells/well in RPMI media including human 2% heat inactivated AB serum, glutamine, Pen-strep and β-mercapto-ethanol. The cells were treated with TLR7 agonists for 24 h in 4 doses. The conditioned media was removed for ELISA analyses for IL-6, and the EC50 value determined for each compound and each batch.

Experimental Setup:
1. Untreated cells
2. Untreated cells (vehicle control)
3. Imiquimod
4. Compound A (new batch#20289)
5. Compound A (old batch#CH730/25/8)
6. SC12 (new batch#20288)
7. SC12 (old batch#CH730/2/13D)

All compounds were tested in four concentrations (10-1-0,1-0,01 micromolar). IL6 was determined after 24 h incubation in conditioned media by ELISA (IL6 gave in the last experiment the most comparable dose-response results).

Data Handling:

Concentrations of IL-6 were determined by ELISA from R&D Systems using the Microsoft Excel software. The results were analyzed in Graph Pad Prism in order to prepare dose-response curves, and for determination of EC50 values.

Statistical Analyses:

Due to the low number of donors, statistical evaluation between individual EC50 values as not determined.

Results and Discussion

IL-6 was induced dose-dependently by all compounds, except Imiquimod, which was only active in inducing IL-6 at the highest concentration (10 microM). A summary of the results is shown in Table 5 with indication of EC50 values for the two donors tested (top two rows), and compared to the values from the first experiments on the two compounds performed on three donors (bottom three rows). The EC50 values for Imiquimod seemed to be somewhat higher in this present experiment compared to the last experiment. This can be explained by the storage at 4° C., and potentially the heating procedure used to solubilize the compound completely before use. SC12 showed similar EC50 values comparing this experiment with the previous experiment when testing batch CH730/2/13D. The old SC12 batch (CH730/2/13D) showed also similar EC50 values compared to the new batch (#20288). Compound A showed also similar EC50 values in both this and the previous experiment when testing batch (CH730/25/8). The new compound A batch #20289, showed also similar EC50 values compared to the old batch. No test for cell survival was performed since the last experiment showed no cytotoxic activity in the concentrations tested.

TABLE 5

EC50 values determined in PBMCs from 5 different donors at different time points, with different batches of SC12 and compound A.

| EC50 values/microM | Imiquimod | SC12 new 20288 | SC12 old CH730/2/13D | Compound A new 20289 | Compound A old Ch730/25/8 |
|---|---|---|---|---|---|
| Donor 1 | 17.97 | 1.869 | 2.007 | 0.721 | 0.734 |
| Donor 2 | 18.45 | 0.947 | 1.034 | 0.521 | 0.392 |
| D1 | 6.348 | | 1.439 | | 0.460 |
| D2 | 1.994 | | 0.864 | | 0.740 |
| D3 | 4.643 | | 2.782 | | 0.255 |

Conclusions

The two TLR7 agonists SC12 and compound A showed similar EC50 in the present experiment, indicating that they contain the same amount of active compound. This further indicated that the compounds (CH730/2/13D and CH730/25/8) have not lost activity during the 5 months storage in DMSO at 4° C.

Example 5

Investigation of the Metabolic Stability of Compound a in Rat, Rabbit, Minipig and Human Plasma and Metabolic Profiling in Rabbit and Human Plasma; Comparison of Compound a and SC12 Stability in Human Plasma Abbreviations:
2-Piperidinoethyl 4-amino-5-chloro-2-methoxybenzoate—M7319
Acetonitrile—ACN
Atmospheric Pressure chemical Ionization—APCI
Dimethylsulfoxide—DMSO
Electron Spray Ionization—ESI
Formic acid—HCOOH
Liquid Chromatography/Mass Spectrometry—LC/MS
Methanol—MeOH
Multiple Reaction Model—MRM
Retention Time—R.T.
Ultra Performance Liquid Chromatography—UPLC Abstract Stability of compound A* (another batch of compound A) was tested in rat, rabbit, minipig and human plasma, and metabolic profiling was assessed in rabbit and human plasma. Compound A* was highly metabolized by esterases in rabbit and human, and in a lesser extent in minipig and rat species. Metabolism was studied in rabbit at 30 and 120 min and in human at 60 and 300 min, keeping approximately constant the percentage remaining of the parent in the two species. Three metabolites were found in rabbit and two of them in human.

In rabbit the major metabolites were the monoester and the acid metabolite, whereas only traces of the di-hydrolized metabolite were observed. In human plasma only the first two major metabolites, previously detected in rabbit, were identified at the selected time points and the acid product was the predominant metabolite at 120 min.

This study found that in human and rabbit species a comparable profile of clearance and metabolism profile was found, with the formation of only two major metabolites where the rate limiting step was the hydrolysis leading to monoester formation, which rapidly converted into the acid derivative.

In a second experiment performed in human plasma with a second batch of compound A (batch 20289) in comparison with SC12 suggested that SC12 was more stable than compound A, because it was not metabolized up to 120 min, and more than 70% of the compound was still present at 300 min. On the contrary, compound A showed instability after 60 min incubation Introduction Hydrolytic enzymes present in plasma strongly contributed to the metabolism of compounds. Many drugs containing an ester bond were used as prodrug to increase permeability or solubility or to decrease toxic systemic effect. Esterases exist in many variety and species differences can generally result from the existence of different types in biological media and differences in their substrate specificity. Additionally bioconversion can be affected by various factors such as age, gender and disease.

Objective

The purpose of the assay was to compare stability, as percentage remaining of the parent, in several plasma species at different time points. Profiling of the major metabolites formed after incubation in plasma at 2 time points was carried out in rabbit and human plasma.

A second experiment with a different batch of compound A was performed by utilizing a different batch of human plasma and in comparison with SC12.

Plasma Stability and Metabolism Studies

Materials

The following substances were obtained from the source indicated: ACN from J. T Baker, Germany, lidocaine, verapamil and M7319 from Sigma-Aldrich. HCOOH from Fluka. Deionized water from MilliQ apparatus (Millipore).

Plasma Samples were Obtained from the Source Indicated:

Rat plasma from Charles River, Calco, Italy. Minipig, human and rabbit plasma from Biopredic, Rennes, France.

Compound A 2-(4-((6-amino-2-(2-methoxyethoxy)-8-oxo-7H-purin-9(8H)-yl)methyl)benzamido)ethyl 2,3-bis(oleoyloxy)propyl phosphate Batch code: compound A* (First experiment), 20289 (Second experiment).

Storage Conditions: 4° C. as powder, −20° C. as stock solution in DMSO

SC12: 2-(4-((6-amino-2-(2-methoxyethoxy)-8-oxo-7H-purin-9(8H)-yl)methyl)benzamido)ethyl 2,3-bis(oleoyloxy)propyl phosphate Batch code: 20288

Storage Conditions: 4° C. as powder, store desiccated and away from direct light Instruments UPLC (Waters) interfaced with a Premiere XE Triple quadrupole (Waters) for clearance determination and UPLC (Waters) interfaced with Ion Trap HCTultra (Bruker Daltonics) for metabolic profiling.

Method

First experiment: Test compounds (50 mM DMSO) were diluted at the final concentration of 250 µM (in duplicate) with ACN. Plasma of different species (1 ml) was spiked with 10 µl of 250 µM solution of the compound and aliquots of 50 µl volume were taken at 0, 15, 30, 60, 120 min and 5 hrs, and immediately quenched with 200 µl of a solution of Verapamil 250 ng/ml (internal standard, I.S.) in ACN. A 10 µl of MeOH was added to improve solubility. Samples were then centrifuged for 5 min at 13000 rpm and analyzed as reported below. Lidocaine and M7319 were used as reference standards and incubated as described above. The supernatant fractions were analyzed by LC/MS/MS. Zero-time incubations were used as 100% values. Percent loss of substrate in incubations was determined to estimate the in vitro half life of the test compound.

Metabolism experiments were performed at 50 µM final concentration of test compound and samples collected at two time points established in light of the half life of the compound, and analyzed by LC/MS/MS after addition of ACN and internal standard.

Second experiment: Test compounds (5 mM in DMSO) were diluted at the final concentration of 250 µM with ACN-MeOH 1:1.

Human plasma (1.180 ml) was spiked with 20 µl of 250 µM solution of the compound (4.16 µM final concentration) and aliquots of 50 µl volume were taken at 0, 15, 30, 60, 120 min and 5 hrs, and immediately quenched with 200 µl of a solution of Verapamil 250 ng/ml (internal standard, I.S.) in ACN: MeOH 95:5. Samples were then centrifuged for 20 min at 3000 rpm at 10° C. and analyzed as reported below. Lidocaine and M7319 were used as reference standards and incubated as described above. The supernatant fractions were analyzed by LC/MS/MS. Zero-time incubations were used as 100% values.

Sample Analysis

Sample analysis for plasma stability determination (First experiment)

Samples were analyzed on a UPLC (Waters) interfaced with a Premiere XE Triple Quadrupole (Waters).

Eluents were:
Phase A: 95% H2O, 5% MeOH, 0.1% HCOOH
Phase B: 5% H2O, 95% MeOH, 0.1% HCOOH
Column: Acquity BEH C8, 2.1×5 mm 1.7 um at 55° C.
Injection.Vol.: 5 µl.

A chromatographic method is reported below in Table 6.

TABLE 6

Chromatographic method for clearance determination

| Time (min) | Flow (ml/min) | % A | % B |
|---|---|---|---|
| 0 | 1 | 90 | 10 |
| 0.2 | 1 | 90 | 10 |
| 0.3 | 1 | 0 | 100 |
| 4.0 | 0.6 | 0 | 100 |

ESI pos, Capillary 3.4 kV, Extractor 5V, Source T 115° C., Desolvation T 450° C. Cone Gas L/h 98, Multiplier 630 V.

In Table 7 the MRM transitions applied to compound A were reported.

TABLE 7

MRM transitions and parameters applied

| Compound | Q1/Q3 | Cone (V) | Collision Energy (V) |
|---|---|---|---|
| compound A | 1086.6/604.4 | 35 | 30 |
| | 1086.6/385.2 | | |

Sample Analysis for Metabolic Profiling

The samples were analyzed using a Waters UPLC chromatographic system coupled with a Bruker Daltonics HCTultra® ion trap Mass Spectrometer. Before the analysis of the incubated samples, compound A was infused manually to understand parent fragmentation. Infusion was performed by diluting a 50 mM solution in DMSO to 1 µM with ACN/MeOH 1/1. Sample solution was infused into the ion trap source at a flow rate of 4 ul/min.

Through a T-union 75 µl/min of $H_2O$/ACN 1/1+0.1% formic acid from the UPLC system was mixed with the flow of the compound solution to stabilize the flow rate and the signal.

The following conditions were applied to the Ion Trap: ESI positive, Capillary −4 KV, Cap Exit 164.3V, Skimmer 40V, Trap Drive 88.4, Neb. Gas 70 psi, Dry Gas 10 l/min, Dry Temp 350° C.

Incubated samples were analyzed on a UPLC (Waters) interfaced with an Ion Trap HCT ultra (Bruker Daltonics).

Eluents were:
Phase A: 95% H2O, 5% MeOH, 0.1% HCOOH
Phase B: 5% H2O, 95% MeOH, 0.1% HCOOH
Column: Acquity BEH C8 50×2.1 mm, 1.7 um at 55° C.
Injection.Vol.: 5 ul.

A chromatographic method is reported below in Table 8.

TABLE 8

Chromatographic method for metabolic profiling

| Time (min) | Flow (ml/min) | % A | % B |
|---|---|---|---|
| 0 | 1 | 90 | 10 |
| 0.2 | 1 | 90 | 10 |
| 7 | 1 | 0 | 100 |
| 12 | 1 | 0 | 100 |

Sample Analysis (Second Experiment)

Compound A and SC12 were analyzed using a Waters UPLC chromatographic system coupled with a Bruker Daltonics HCTultra® Ion Trap Mass Spectrometer.

Eluents were:
Phase A: 95% H2O, 5% MeOH, 0.1% HCOOH
Phase B: 5% H2O, 95% MeOH, 0.1% HCOOH
Flow 0.6 ml/min. Column: Supelco, Discovery HS F5, 3.3 cm×2.1 mm; 55° C.
Injection Volume: 10 µl.

A chromatographic method is reported below in Table 9.

TABLE 9

Chromatographic method

| Time (min) | % A | % B |
|---|---|---|
| 0 | 90 | 10 |
| 0.5 | 90 | 10 |
| 1 | 0 | 100 |
| 3 | 0 | 100 |
| 3.1 | 90 | 10 |
| 3.5 | 90 | 10 |

The following conditions were applied to the Ion Trap:

For compound A: ESI positive, Capillary −4 KV, Cap Exit 164.3V, Skimmer 40V, Trap Drive 88.4, Neb. Gas 70 PSI, Dry Gas 10 l/min, Dry Temperature 350° C.

For SC12: ESI positive, Capillary −4 KV, Cap Exit 200V, Skimmer 49.5V, Trap Drive 85.0, Neb. Gas 70 PSI, Dry Gas 10 l/min, Dry Temperature 350° C.

MRM transitions used for the quantifications were reported in Table 10.

TABLE 10

MRM transitions

| Compound | [MH]+ | Transitions |
|---|---|---|
| Compound A | 1085.6 | 603.6→385.23 |
| SC12 | 921.6 | 439.45→385.23 |

Data Analysis

Stability was calculated as percentage remaining of the area ratio compound/I.S. at each time point vs. area ratio compound/I.S. at time 0 min. A general stability classification is reported in Table 11.

TABLE 11

General stability classification at 1 hr of incubation

| | % remaining | | | |
|---|---|---|---|---|
| | >80 | 80-60 | 60-30 | <30 |
| Classification | Stable | Slightly unstable | Unstable | Unstable |

Metabolism was studied at 60 min and 300 min in human plasma, and at 30 and 120 min in rabbit plasma, i.e. at the time points where the two species showed a similar percentage remaining of the parent compound. Assignment of the structures was done by comparison of the MS/MS analysis of the spectra with the parent spectrum.

Results

Plasma Stability (First Experiment)

Results obtained on plasma stability experiments are shown in Table 12.

Compound A was unstable in all the tested species; rabbit was the species with the highest clearance, followed by human and rat species; minipig showed the lowest clearance. In rabbit, rat and human plasma the first part of the curve up to 30 min is steep, whereas the remaining part has a milder slope. Standards were in agreement with literature data.

TABLE 12

Percentage remaining of compound A in rat, rabbit, minipig and human plasma (% Remaining - Mean ± S.D.)

| Time (min) | Rat | Rabbit | Minipig | Human |
|---|---|---|---|---|
| 0 | 100 | 100 | 100 | 100 |
| 15 | 73.8 ± 4.5 | 38.7 ± 3.4 | 102.4 ± 3.3 | 99.7 (*) |
| 30 | 67.1 ± 8.8 | 10.2 ± 1.0 | 73.3 ± 5.0 | 40.4 ± 15.5 |
| 60 | 25.2 ± 0.5 | 7.4 ± 0.1 | 78.6 ± 2.9 | 36.1 ± 7.6 |
| 120 | 21.4 ± 1.9 | 4.4 ± 0.7 | 33.7 ± 2.3 | 17.4 ± 2.6 |
| 300 | 15.3 ± 1.0 | 1.9 ± 0.1 | 10.8 ± 0.3 | 7.8 ± 3.3 |

Data are expressed as Mean ± S.D., n = 2, except when (*) where n = 1

Plasma Stability (Second Experiment)

Results on human plasma stability experiments for compound A and SC12 were shown in Table 13. For compound A, an instability (about 80% remaining) was observed after 60 min incubation reaching a 56% remaining at 300 min. In this second experiment a different batch of compound A together with different analytical conditions and batch of human plasma in respect to the first experiment have been utilized: this could explain some differences observed between the percent remaining obtained.

SC12 was stable in human plasma up to 120 min. More than 70% of compound was still present after 300 min incubation. This data is in line with that found in a previous experiment (data not shown). Standard compounds tested in the same experiment were in agreement with literature data (Table 14).

TABLE 13

Percentage remaining of compound A and SC12 in human plasma

| Time (min) | Compound A | SC12 |
|---|---|---|
| | (Mean ± S.D.) % remaining | |
| 0 | 100 | 100 |
| 15 | 100.6 ± 14.5 | 112.6 ± 1.0 |
| 30 | 90.3 ± 13.3 | 110.0 ± 1.0 |
| 60 | 79.5 (*) | 96.7 ± 6.3 |
| 120 | 69.8 ± 16.8 | 102.1 ± 8.7 |
| 300 | 55.7 ± 9.9 | 72.4 ± 4.6 |

Data are expressed as Mean ± S.D., n = 2; except when (*) where n = 1

TABLE 14

Percentage remaining of standard compounds in human plasma

| Time (min) | Lidocaine | M7319 |
|---|---|---|
| | (Mean ± S.D.) % remaining | |
| 0 | 100 | 100 |
| 60 | 107.1 ± 7.7 | 23.3 ± 1.4 |
| 300 | 105.1 ± 3.3 | 0.01 ± 0.01 |

Metabolic Profiling

Parent fragmentation: Major fragments were attributed as reported in Table 15 from MS/MS spectrum.

TABLE 15

Attribution of compound A major fragments

| MH+ (m/z) | Delta m/z | Proposed Structure |
|---|---|---|
| 1085 | parent | |

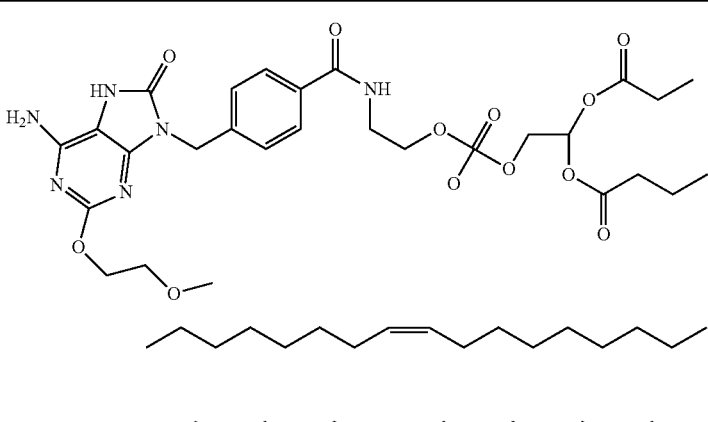

TABLE 15-continued

Attribution of compound A major fragments

| MH+ (m/z) | Delta m/z | Proposed Structure |
|---|---|---|
| 603 | −482 | 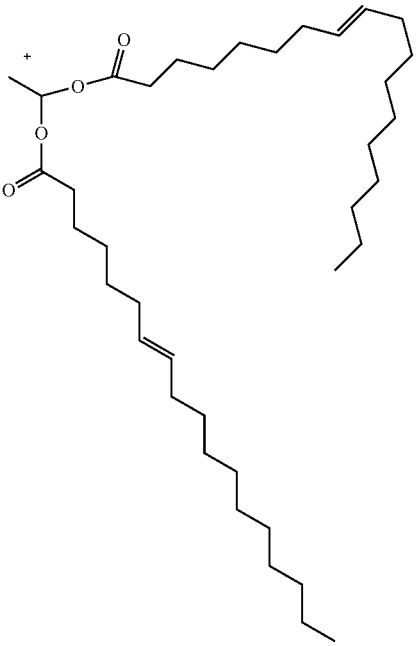 [SMILES: CCCCCCCCC/C=C/CCCCCCC(=O)OC(C)OC(=O)CCCCC/C=C/CCCCCCCCCC] |
| 385.6 | −700 | 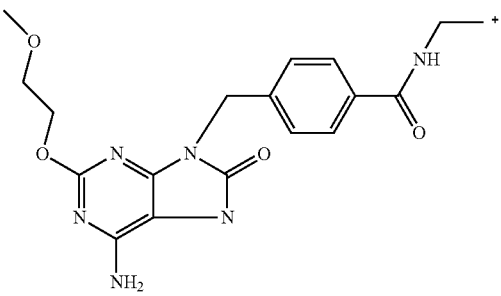 |
| 327 | −758 | 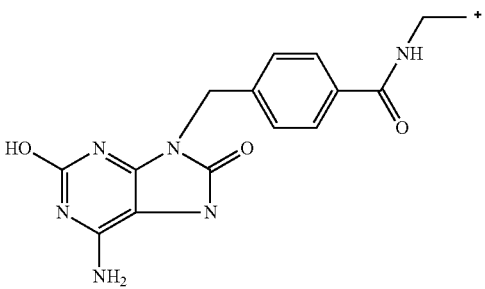 |

Metabolites Profiling

Metabolic profiling was studied in rabbit and human plasma. In both matrixes the parent compound (50 uM starting concentration) was totally metabolized at the last time point. Metabolites were detected in Full scan and peaks were assigned by MH+ and MS/MS spectra. The parent compound showed a low response in Full Scan profile, therefore initial Full Scan chromatograms were not significant.

A summary of the metabolites with MH+ and retention time was reported in Table 16. In rabbit species three metabolites with MH+ of 557, 821 and 360 respectively, were detected at retention times (r.t.) 1.1, 6.3 and 6.4 min.

The most abundant peak corresponded to MH+821 (M2) that was assigned to the mono-ester product which was converted 1:1 into the acid metabolite at 120 min; only a small peak corresponding to the di-hydrolized product was present (MH+557, M1). A similar profile was also observed in human plasma where the two major metabolites showed the same MH+ and retention time of rabbit profile and their ratio was 1:1 after 60 min of incubation, while metabolite M3 was the major product at 300 min. Traces of di-hydrolized metabolite (MH+557) were present in human plasma already at time 0 and therefore it was not considered as metabolite. Therefore it was hypothesized that the rate determining step of metabolism was the formation of the monoester whereas all the other degradation steps occur in a much faster way. A potential selectivity of hydrolysis in position 1 or 3 of the di-acyl glycerol moiety was not attributed.

TABLE 16

Identified metabolites in rabbit and human plasma

|  | M1 | M2 | M3 |
|---|---|---|---|
| min | 1.1 | 6.3 | 6.4 |
| MH+ | 557 | 821 | 360 |
| Rabbit | x | x | x |
| Human |  | x | x |

Conclusions

Compound A stability in plasma was studied in four species: rabbit, human, rat and minipig. The product was highly metabolized by esterases in rabbit and human and at a lesser extent in minipig and rat. Metabolism was studied in rabbit at 30 and 120 min and in human at 60 and 300 min keeping approximately constant the percentage remaining of the parent in the two species. Three metabolites were found in rabbit (M1, M2 and M3) and two of them in human (M2 and M3). In rabbit the major metabolites were the monoester and the acid metabolite whereas only traces of the di-hydrolized metabolite were observed. In human plasma only the monoester and the acid metabolite, previously detected in rabbit, were identified at the selected time points and the acid product was the predominant metabolite at 120 min.

In conclusion the two species present a comparable profile of clearance and metabolism profile with the formation of only two major metabolites where the rate limiting step was the hydrolysis leading to monoester formation which rapidly converted in to the acid derivate.

SC12 appeared more stable than compound A in human plasma, with a 70% of compound still present at 300 min.

Example 6

Potency of TLR7 Agonists in Human Whole Blood Assays on Plasmacytoid DCs, Myeloid DCs and B Cells Aim To determine the potency of 2 TLR7 agonists in whole blood assays in comparison to Imiquimod. Specifically, it will be examined if the two TLR7 agonists compound A and SC12 show differences in potency in activation of immune cells in the whole blood assay. The optimal parameters in order to be able to show differences between the biological effect of compound A and SC12 were believed to be measurements of B-cell, myeloid DC and plasmacytoid DC activation.

Methods and Experimental Setup

A volume of approximately 55 mL fresh whole blood was drawn in heparinized Vacutainers from three healthy adult anonymous volunteers as described (J. A. Ida, Journal of Immunol Methods, 310, 2006, 86-99). The donors were healthy, did not suffer from known immune disorders, and were not on medication. Before drawing the blood, the compounds were added to 96 well round bottom plates in a 10× diluted sample at 20 ul. The compounds were diluted in RPMI media without serum but with antibiotics. Antibiotics were added at a 10× concentration. After drawing the blood, the whole blood sample was gently mixed to obtain a homogeneous sample, and 180 ul was added to each well.

After 6 hours and 24 hours incubation, plasma was removed for ELISA (IL-6, IL-10, IL-12p40 and IFN-alpha). ELISA was made at the 6 and 24 hours time point for all concentrations. After 24 hours incubation with selected compound concentrations, cells were analyzed for activation markers by FACS.

The following samples were prepared:
Experimental Setup:
1. Untreated cells
2. Untreated cells (vehicle control)
3. Imiquimod (old batch)
4. Compound A (old batch)
5. SC12 (old batch)

All compounds were setup in concentrations at 0-0.01-0.03-0.1-0.5-2.0-10.0 micromolar as the final concentration. Vehicle control was DMSO control, where we used the highest concentration used for the compounds. After addition of blood, all plates were gently agitated at 37° C. and 5% $CO_2$ until harvest. The samples were removed after 6 or 24 hours incubation, and pooled into appropriate tubes (2 ml).

For the 6 hours time point, the plate was centrifuged 500×g. Supernatant (SN) was transferred to a tube and centrifuged at 10.000×g for 10 min to get rid of cells and protein aggregates. The clarified supernatant was frozen at −80 C until analysis.

For the 24 hours time point, the samples in the wells were pooled into tubes, which were centrifuged 500×g for 10 min at 4 C to clarify the SN. The SN was removed to another tube and centrifuged at 10.000×g for 10 min. to get rid of aggregates etc. The clarified supernatant was frozen at −80 C until analysis.

FACS Analysis

A flow cytometric analysis was performed on whole blood from three donors after treatment with two compound concentrations for 24 h. The FACS analysis for donor 1 and donor 2 was made on another day than donor 3. The compound concentrations were as follows:
B cell activation: 2 and 10 uM
mDC/pDC: 0.1 and 0.5 uM The FACS analysis was used to identify whether the test compounds could induce activation of B cells, and two different subsets of dendritic cells, namely the myeloid CD11c+/CD123− DCs and the plasmacytoid CD11c−/CD123+ DCs. The following markers were studied to identify the activation status of the different subsets:
B-cells: HLA-DR/CD2O/CD40
pDCs: HLA-DR/CD123+/CD11c−/CD80
HLA-DR/CD123+/CD11c−/CD86
HLA-DR/CD123+/CD11c+/CCR7
mDCs: HLA-DR/CD123−/CD11c+/CD80
HLA-DR/CD123−/CD11c+/CD86
HLA-DR/CD123−/CD11c+/CCR7

The FACS staining was performed according to the manufacturer's instructions. Lysis of red blood cells was performed before FACS staining in order to minimize auto-florescence. To include as many B cells and DCs in the study as possible the FACS analyses were performed on 500,000 cells in total for each staining. A P1 gate was set only to include relevant cells on FSC vs. SSC (see FIGS. 12-15). The results of the individual analysis were present as Mean Fluorescence Intensity (MFI) values, for certain activation marker in a given gate setting, represent the actual cell subset. The isotype background values have been used to set the gates so that a maximum at 2% of unspecific stained cells could be found in the positive gates.

Data Handling:

Concentrations of cytokines were determined by ELISA from R&D Systems. The results were analyzed in Graph Pad Prism in order to prepare dose-response curves, and for determination of EC50 values. FACS analysis was made by using Becton-Dickinson FACSDiva software and subsequently illustrated in Graph Pad Prism.

Statistical Analyses:

Statistical evaluation between individual EC50 values was for relevant cytokines determined using two-tailed T-test with unequal variance.

Results and Discussion:

Cytokine Secretion

IL-6 Secretion after 6 and 24 h

After 6 h incubation with compound A and SC12, all donors induced IL-6 secretion in a dose-dependent manner. Imiquimod induced low and insignificant amounts of IL-6, which did not allow a sigmoid dose-response curve as for compound A and SC12. EC50 values were determined for compound A and SC12 as seen in table 17. There was a tendency for SC12 to show slightly more potent EC50 values than compound A in all three donors. However, based on only three donors, this could not be confirmed as being statistically significant.

TABLE 17

EC50 values for IL-6 secretion after 6 hours incubation in whole blood with TLR7 agonists.

| EC50-IL-6, 6 h Incubation/uM | Imiquimod | Compound A | SC12 |
|---|---|---|---|
| Donor 1 | — | 0.94 | 0.57 |
| Donor 2 | — | 0.63 | 0.18 |
| Donor 3 | — | 0.52 | 0.37 |

After 24 h incubation with compound A, SC12 and Imiquimod, all donors induced IL-6 secretion, but Imiquimod only in the highest concentration tested. EC50 values were determined for all compounds, however, for Imiquimod this determination was not accurate since only the highest concentration was significantly above the detectable level, which did not allow a sigmoid-dose response curve. The levels of IL-6 after 24 hours incubation were only slightly above the levels of IL-6 seen after 6 hours incubation. EC50 values of all compounds for IL-6 secretion after 24 hours incubation was seen in table 18. There was the same tendency at 24 hours as for 6 hours, that SC12 was slightly more potent, and showed lower EC50 values than compound A in all three donors. Comparison between the result for all three donors on EC50 values for compound A and SC12 using a two tailed T test showed a P-value of 0.07, which shows that the responses for the two compounds was not significantly different.

TABLE 18

EC50 values for IL-6 secretion after 24 hours incubation in whole blood with TLR7 agonists.

| EC50-IL-6, 24 h Incubation/uM | Imiquimod | Compound A | SC12 |
|---|---|---|---|
| Donor 1 | 11.06 | 0.52 | 0.22 |
| Donor 2 | 10.57 | 0.32 | 0.06 |
| Donor 3 | 10.58 | 0.29 | 0.17 |

In summary, IL6-secretion was induced by compound A and SC12 in all three donors to similar levels and with similar EC50 values, but SC12 showed a tendency to be slightly more potent. Furthermore, the range of IL-6 secretion (4000-8000 pg/ml) was in line with results published by Clarke et al., Jour. Interferon & Cytokine Research, 29, 2, 2009, 113-126.

IFN-Alpha Secretion after 6 and 24 Hours

After 6 hours incubation with compound A and SC12, all donors induced IFN-alpha secretion in a dose-dependent manner, whereas Imiquimod did not induce IFN-alpha secretion. Donor 1 and 2 induced IFN-alpha to levels in the 2000 pg/ml range, whereas donor 3 only induced to the 500 pg/ml range. EC50 values were determined for compound A and SC12 as seen in Table 19. There was again a tendency for SC12 to show slightly more potent EC50 values than compound A in all three donors, however, this was not significant ($P=0.23$).

TABLE 19

EC50 values for IFN-alpha secretion after 6 h incubation in whole blood with TLR7 agonists.

| EC50-IFN-alpha, 6 h Incubation/uM | Imiquimod | Compound A | SC12 |
|---|---|---|---|
| Donor 1 | — | 1.17 | 0.98 |
| Donor 2 | — | 1.84 | 0.83 |
| Donor 3 | — | 1.94 | 1.66 |

After 24 hours incubation with compound A, SC12 and Imiquimod, all donors induced IFN-alpha secretion, but Imiquimod again only in the highest concentration tested. EC50 values were determined for compound A and SC12. The EC50 value for Imiquimod was again not accurate due to induction at the highest concentration only. The levels of IFN-alpha after 24 h incubation were below the levels of IFN-alpha seen after 6 hours incubation for donor 1 and 2, indicating that this cytokine can be removed by cells in the assay. EC50 values of all compounds for IFN-alpha secretion after 24 hours incubation were seen in table 20. After 24 hours all three donors induced IFN-alpha in the 1000 pg/ml range, indicating that donor 3 responded to compound A and SC12 slowed than donor 1 and 2. SC12 was again slightly more potent than compound A, although it was not significantly different ($P=0.11$).

TABLE 20

EC50 values for IFN-alpha secretion after 24 h incubation in whole blood with TLR7 agonists.

| EC50-IFN-alpha, 24 h Incubation/uM | Imiquimod | Compound A | SC12 |
|---|---|---|---|
| Donor 1 | 10.81 | 0.24 | 0.20 |
| Donor 2 | 10.56 | 0.47 | 0.11 |
| Donor 3 | 10.55 | 0.35 | 0.24 |

In conclusion, IFN-alpha secretion was induced by compound A and SC12 in all three donors to similar levels and with similar EC50 values, but SC12 showed a tendency to be slightly more potent. In comparison to published results, the ranges of IFN-alpha secreted in this study (1000-2000 pg/ml) was higher than published data (<200 pg/ml), shown with Resiquimod (Clarke et al., Jour. Interferon & Cytokine Research, 29, 2, 2009, 113-126). However, this can be explained by expected lower potency of Resiquimod compared to compound A and SC12. Secondly, IFN-alpha secretion was known mainly to be induced by pDCs, and since IFN-alpha was secreted already after 6 hours in this study, it indicates that pDCs were activated as one of the initial responses seen after treatment of whole blood cells with compound A and SC12 (J. A. Ida, Journal of immunol methods, 310, 2006, 86-99).

IL-10 Secretion after 6 and 24 h

After 6 hours incubation with Imiquimod, compound A or SC12, and no IL-10 production was seen, indicating that IL-10 secretion was a secondary effect to treatment of whole blood cells with the TLR7 agonists. After 24 hours incubation with compound A, SC12 or Imiquimod, all donors induced IL-10 secretion, but Imiquimod again only in the highest concentration tested. EC50 values were determined for all compounds, however, for Imiquimod this determination was again not accurate due to induction of IL-10 at the highest concentration only. EC50 values of all compounds for IL-10 secretion after 24 hours incubation were seen in table 21. After 24 hours all three donors induced IL-10 in the 2000-40000 pg/ml range. compound A and SC12 showed similar ability to induce IL-10, with no significant differences between the two compounds.

TABLE 21

EC50 values for IL-10 secretion after 24 hours incubation in whole blood with TLR7 agonists

| EC50-IL-10, 24 h Incubation/uM | Imiquimod | Compound A | SC12 |
|---|---|---|---|
| Donor 1 | 4.00 | 1.29 | 1.34 |
| Donor 2 | 10.81 | 0.86 | 0.41 |
| Donor 3 | 12.87 | 2.28 | 9.00 |

In conclusion, IL-10 was induced later in the assay, with no induction after 6 hours, but only after 24 hours incubation. This indicates that IL-10 was induced as a secondary response in the assay, and possibly not as a direct effect of TLR7 ligation with the compounds tested. This was consistent with studies by Douagi et al, Journal of Immunology, 182, 2009, 1991-2001, where IL-10 was induced in a human PBMC model only after 12 and 20 hours, but not after 4 hours. Furthermore, Douagi et al, showed that mDCs were the main producers of IL-10 compared to pDCs. Supported by studies by Boonstra et al., Journal of Immunology, 177, 2006, 7551-7558, who showed that mouse macrophages and mDCs produced IL-10 much more potently than pDCs after TLR ligation, the current results on IL-10 secretion by TLR7 ligation, indicates that the secretion of IL-10 occurs in mDCs or potentially macrophages present in the whole blood assay, potentially as a secondary response.

IL-12p40 Secretion after 6 and 24 Hours

After 6 hours incubation with compound A and SC12, all donors induced IL-12p40 secretion in a dose response manner, whereas Imiquimod did not induce IL-12p40 secretion, not even in the highest concentrations. All donors induced IL-12p40 to levels in the 8.000-12.000 pg/ml range. EC50 values were determined for compound A and SC12 as seen in table 22. The compounds seemed to be equally potent in induction of IL-12p40, with no significant differences.

TABLE 22

EC50 values for IL-12p40 secretion after 6 hours incubation in whole blood with TLR7 agonists.

| EC50-IL-12, 6 h Incubation/uM | Imiquimod | Compound A | SC12 |
|---|---|---|---|
| Donor 1 | — | 2.31 | 1.96 |
| Donor 2 | — | 2.09 | 2.36 |
| Donor 3 | — | 3.43 | 3.56 |

After 24 hours incubation with compound A, SC12 or Imiquimod, all donors induced IL-12p40 secretion to levels of IL-12p40 in the 20.000-25.000 pg/ml range after compound A and SC12 treatment, whereas Imiquimod did not induce IL-12p40 even in the highest concentrations. EC50 values were determined for compound A and SC12 as seen in table 23. Both compounds showed similar EC50 values, with no significant differences.

TABLE 23

EC50 values for IL-12p40 secretion after 24 hours incubation in whole blood with TLR7 agonists

| EC50-IL-12p40, 24 h Incubation/uM | Imiquimod | Compound A | SC12 |
|---|---|---|---|
| Donor 1 | — | 2.87 | 4.10 |
| Donor 2 | — | 2.74 | 1.42 |
| Donor 3 | — | 4.03 | 14.17 |

In conclusion, IL-12p40-secretion was induced by compound A and SC12 in all three donors to similar levels and with similar EC50 values. The induction was seen both at 6 and 24 hours treatment, with increased amounts at the 24 hours time point. In mouse cells, IL-12p40 is mainly produced by mDCs upon TLR ligation, compared to the production in macrophages and pDCs (Boonstra et al., Journal of immunology, 177, 2006, 7551-7558). If a similar pattern of IL-12p40 expression was seen for human cells, it indicates that compound A and SC12 follow a similar activation profile in human mDCs.

Conclusions Regarding Cytokine Secretion

Compound A and SC12 were potent inducers of DC secreted cytokines identified in the supernatant from whole blood cell assays, whereas Imiquimod was a weak inducer of these cytokines. This result was expected based on previous results in a PBMC model with the same compounds. There was a tendency for SC12 to be slightly more potent in induction of IL-6 and IFN-alpha, compared to the potency of compound A. However, with the number of three donors used, this could not be demonstrated to be statistically significant.

For IL-10 and IL-12p40 secretion, compound A and SC12 were equally potent based on this study. IL-10 was not produced after 6 hours, but only after 24 hours incubation. IL-12p40 was induced both after both 6 and 24 hours incubation.

Based on the current knowledge involving TLR7 activation of PBMCs and whole blood assays, pDCs are known to be the main producers of IFN-alpha. IL-6 was produced by both mDCs and pDCs, IL-10 was produced mainly by mDCs, and IL-12p40 mainly by mDCs. The production pattern of IL-6 and IFN-alpha could indicate that SC12 was slightly more potent in activation of pDCs than compound A. In assays with human primary cells, the presence and activation with TLR7 ligands of pDCs was required for stimulation of B-cell proliferation, and the production of IFN-alpha from pDCs was known to be required for activation of B-cell proliferation and initiation of antibody production (Douagi et al, Journal of immunology, 182, 2009, 1991-2001, FIGS. 2 and 3).

In the previous model with testing of compound A and SC12 in the PBMC model, compound A showed a tendency to be slightly more potent than SC12 in IL-6 secretion, however, this was not significant in the previous study either. A difference in potency of compounds in the two models can potentially be explained by differences in chemical or physical properties of the compounds, since differences in lipophilicity potentially will show a difference in partition into the cell pool in each assay. The whole blood assay contains approximately a 50% cell volume, due the presence of large amounts of red blood cells and platelets. In contrast, a PBMC model contains much lower cell volume (<5%). In this regard, the large amounts of cells present in the whole blood assay may work as a buffer for highly lipophilic compounds.

FACS Analysis

Figure 12:
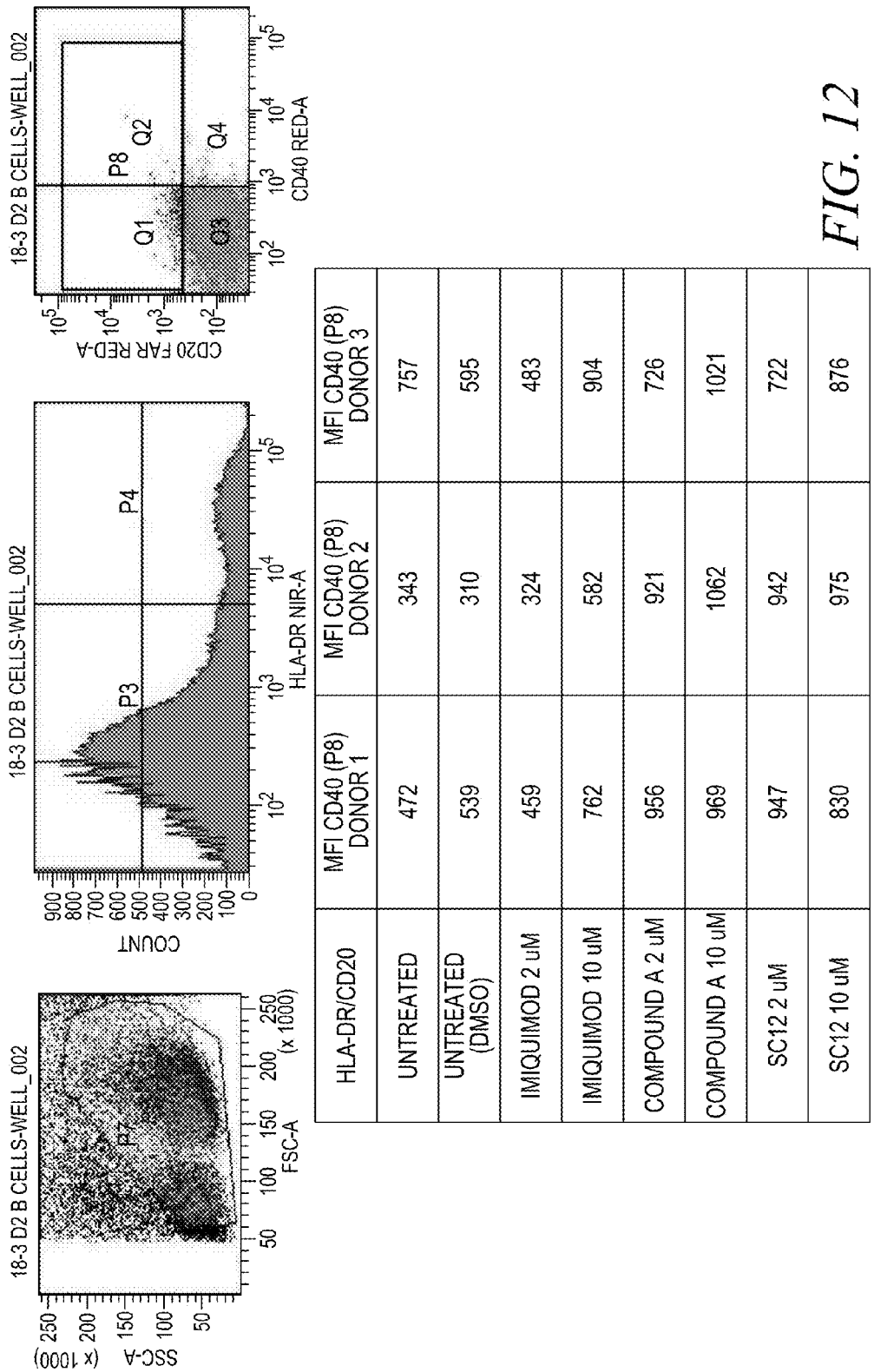
FIG. 12 shows MFI values for CD40 expression on double positive HLA-DR+/CD20+B cells after 24 hours incubation with test reagents as indicated, performed on whole blood from three donors.

B-Cell Analysis (FIG. 12):

The analysis of expression of the activation marker CD40 on B cells was made on double positive HLA-DR (MHC class II) (P4 gate) and CD20 cells (B cell marker) (P8 gate). FIG. 12 shows the results from the three donors after treatment with the test compounds for 24 hours, including the MFI values for CD40 expression on double positive HLA-DR+/CD20+B cells after 24 hours incubation with test reagents as indicated, performed on whole blood from three donors (D1-D3).

The activation marker CD40, shows an increased expression in all three donors after treatment with the control compound Imiquimod in the highest concentration (10 uM), in comparison with untreated or DMSO treated cells. Both test compounds, compound A and SC12, induced CD40 expression in donor 1 and donor 2 in all tested concentrations. However, in donor 3 only the highest concentration of the two test compounds induced CD40 expression compared to untreated cells. In all three donors, compound A showed a weak tendency to stimulate a slightly higher CD40 expression than SC12 in all three donors, when tested at 10 uM. However, this tendency cannot be confirmed as statistically significant due to the small number of donors.

DC Analysis (FIGS. 13-15):

The expression pattern of the co-stimulatory activation marker CD80 and CD86 and the chemokine receptor CCR7 was investigated on two different subsets of DCs. Samples for DC analyses on untreated cells from donor 1 was lost, but a parallel sample which was untreated (DMSO) control cells served as similar control cells.

Figure 13A:
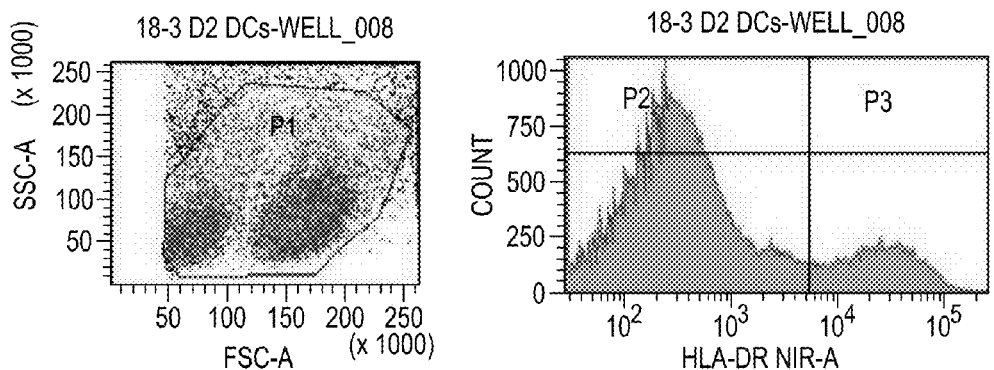
FIGS. 13A and 13B illustrate MFI values for CD80, CD86, and CCR7 expression in HLA-DR+/CD11c+/CD123-mDCs after 24 hour incubation with test reagents as indicated, performed on whole blood from Donor 2.
Figure 13B:
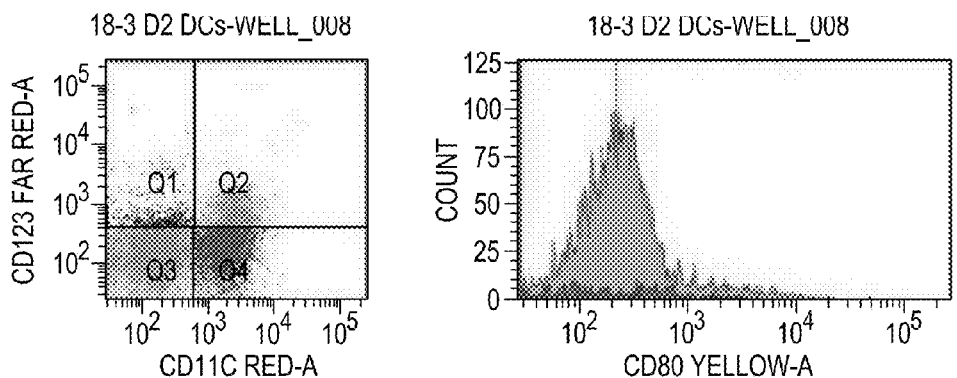
Figure 14A:
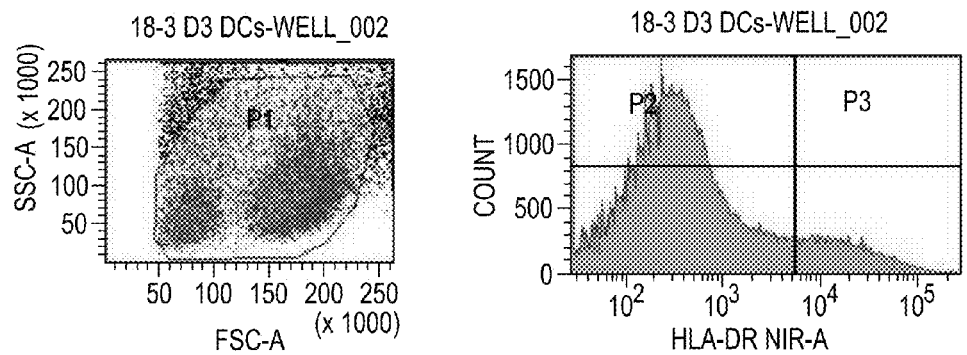
FIGS. 14A and 14B show MFI values for CD80, CD86, and CCR7 expression in HLA-DR+/CD11c+/CD123-mDCs after 24 hour incubation with test reagents as indicated, performed on whole blood from Donor 3.
Figure 14B:
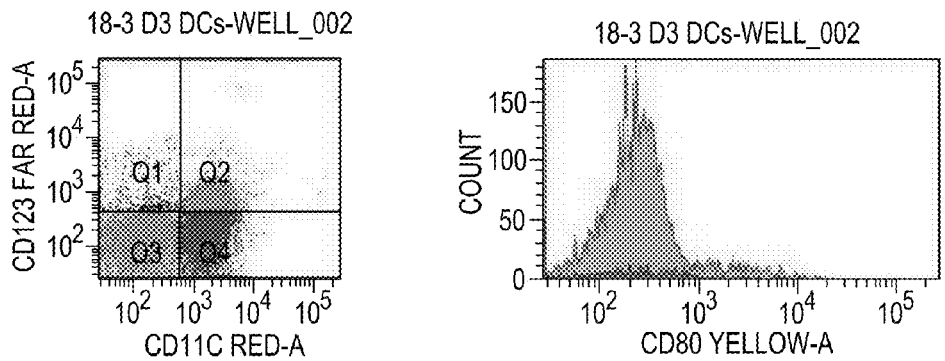
Figure 15A:
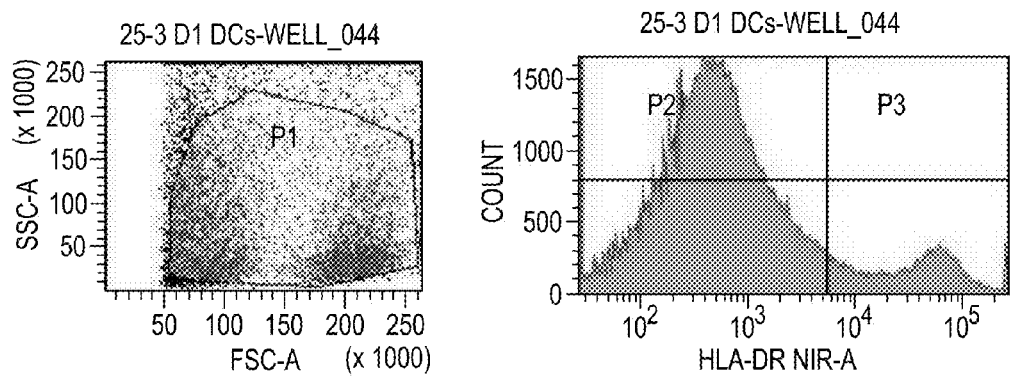
FIGS. 15A and 15B illustrate MFI values for CD80, CD86, and CCR7 expression in HLA-DR+/CD11c+/CD123-mDCs after 24 hour incubation with test reagents as indicated, performed on whole blood from Donor 1.
Figure 15B:
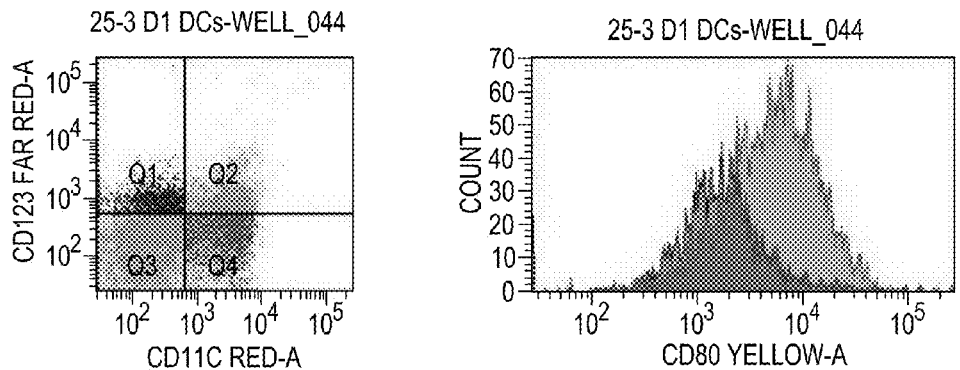

1. Myeloid Dendritic Cells (mDC):

The analysis of myeloid DCs was based on HLA-DR+/CD11c+/CD123− cells, thus all analyzed cells was included in the HLA-DR+(P3) gate and CD11c+/CD123− (Q4) gate (see gates in FIGS. 13-15).

It was found that Imiquimod induced a weak expression of CD80 in donor 1 and 2, which was in contrast to donor 3 where the CD80 expression was high. Both test compounds, compound A and SC12, induced a noteworthy CD80 expression in all three donors. In two out of the three donors (D1 and D3), SC12 in the highest concentration (0.5 uM) showed a potent stimulation on CD80 expression, which was higher than the levels seen for compound A. In donor 2, compound A stimulated CD80 expression slightly more potent than SC12 in the highest concentration only.

Analyses of CD86 expression in mDCs, showed that untreated cells already expressed high levels of CD86 in all three donors, which was not an uncommon observation. However, compound A further stimulates the expression of CD86 in all three donors. SC12 induces a weak CD86 expression in donor 2 and 3, but not in donor 1. The lowest concentration of both test compounds at 0.1 uM, showed most potently to induce CD86 expression. This was in contrast to the CD80 expression where the highest tested dose at 0.5 uM, were the most potent concentration.

The chemokine receptor CCR7, which is a lymph node homing receptor, was also investigated on the mDCs. CCR7 expression showed a higher donor to donor variation than CD80 and CD86. For all donors, compound A induced the highest CCR7 expression, and for donor 1 and 3 Imiquimod also showed high CCR7 expression, which was not seen in donor 2. SC12 was for all donors a less potent stimulator of CCR7 expression.

2. Plasmacytoid Dendritic Cells (pDC)

The analysis of pDCs was based on HLA-DR+/CD11c−/CD123+ cells, thus all analyzed cells were included in the HLA-DR+(P3) gate and CD11c−/CD123+(Q1) gate. (FIGS. 13-15).

In the pDCs both compound A and SC12, shows a comparable effect at the CD80 expression pattern in all three donors. However, SC12 induces a slightly higher CD80 expression than compound A in all three donors, except for the lower concentration in donor 3.

Expression of CD86 in pDCs, shows that SC12 has a tendency to induce higher CD86 expression than compound A in all three donors. However, the most potent concentration varies, as the lowest dose at 0.1 uM, induces the highest CD86 expression in donor 1 and 3, whereas 0.5 uM was the most potent concentration in donor 2. Imiquimod induce a similar high CD86 expression in donor 3 as SC12 and compound A.

Figure 16A:
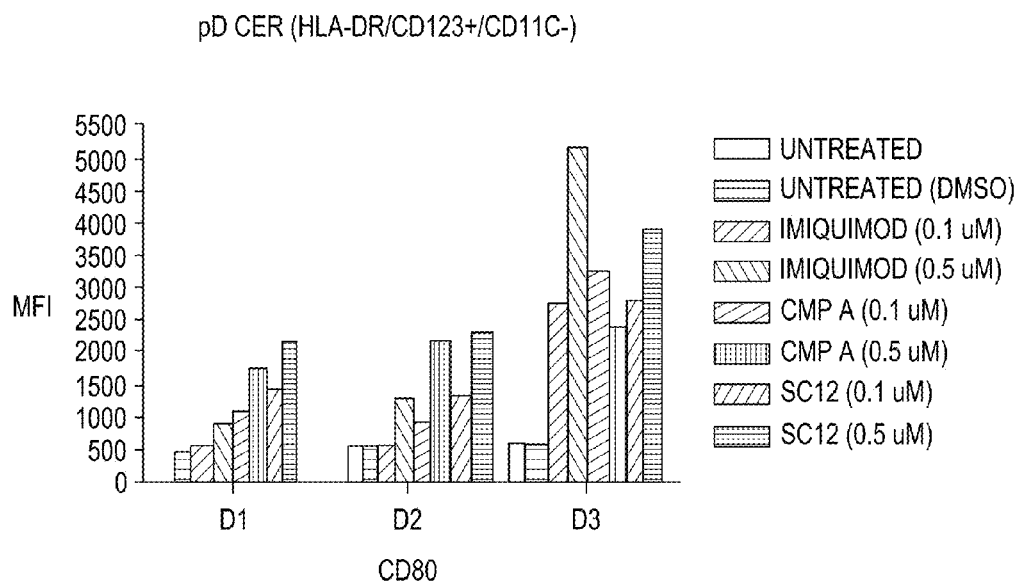
FIGS. 16A and 16B show MFI values for CD80, CD86, and CCR7 expression in HLA-DR+/CD11c-/CD123+pDCs after 24 hour incubation with test reagents as indicated, performed on whole blood from three donors (D1-D3).
Figure 16B:
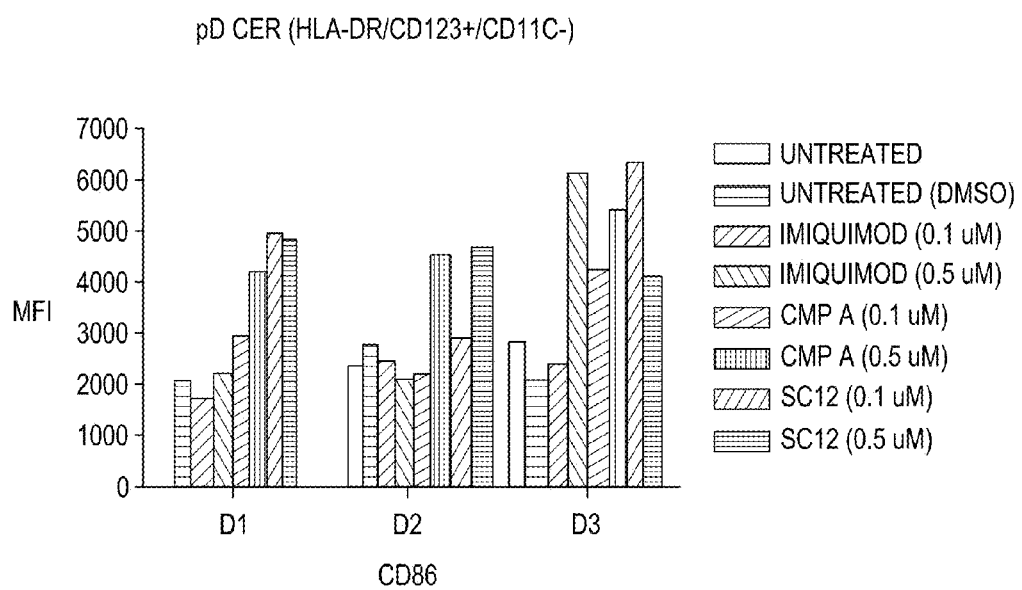
Figure 16C:
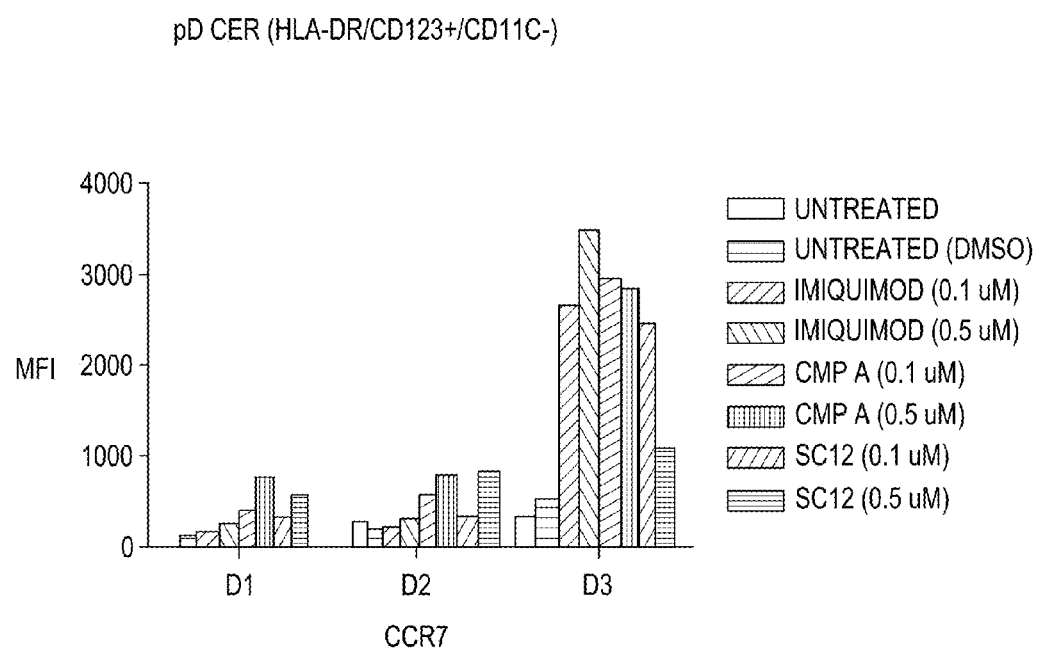
Figure 17A:
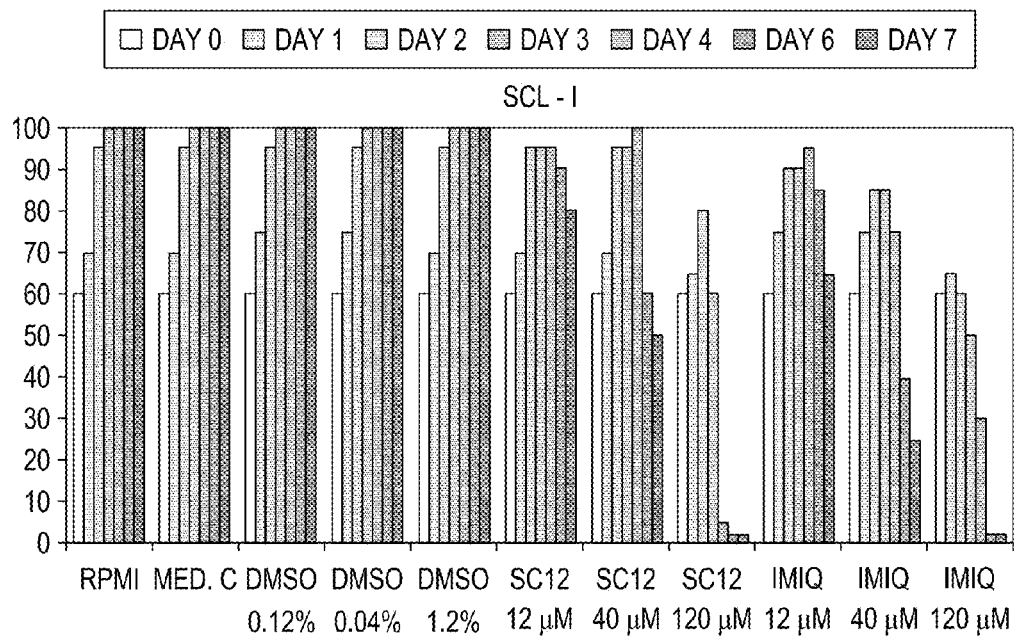
FIGS. 17A-17D are a collection of bar charts of the cytotoxic effects of SC12 and Imiquimod on cells. Cutaneous SCC cell lines were used to continuously monitor of electric conductance in microtiter wells (E-plates, Roche), which correspond to the cell numbers. TMX indicates SC12 in the charts.
Figure 17B:
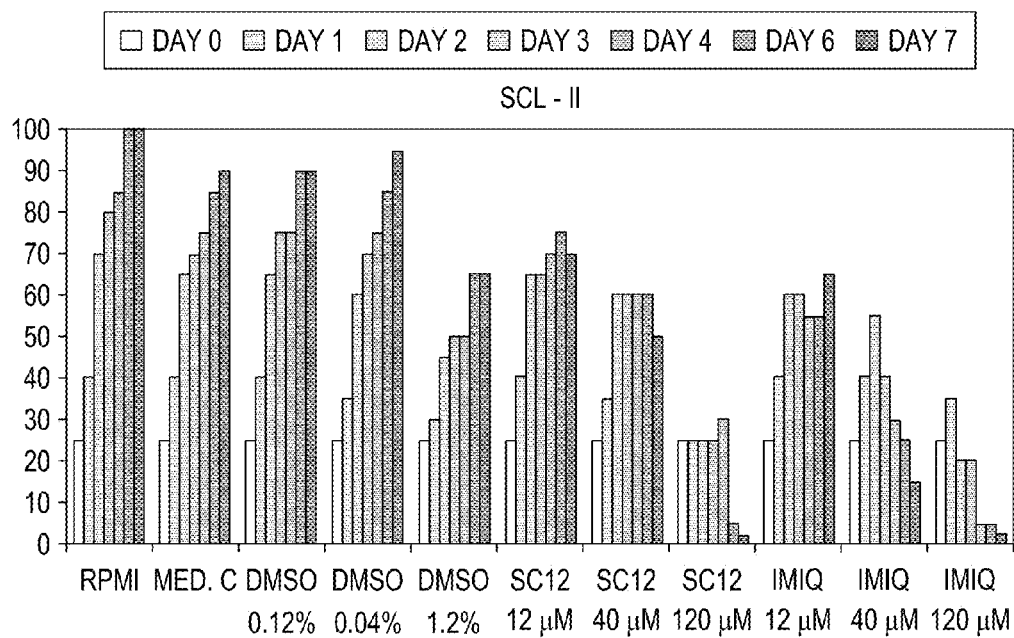
Figure 17C:
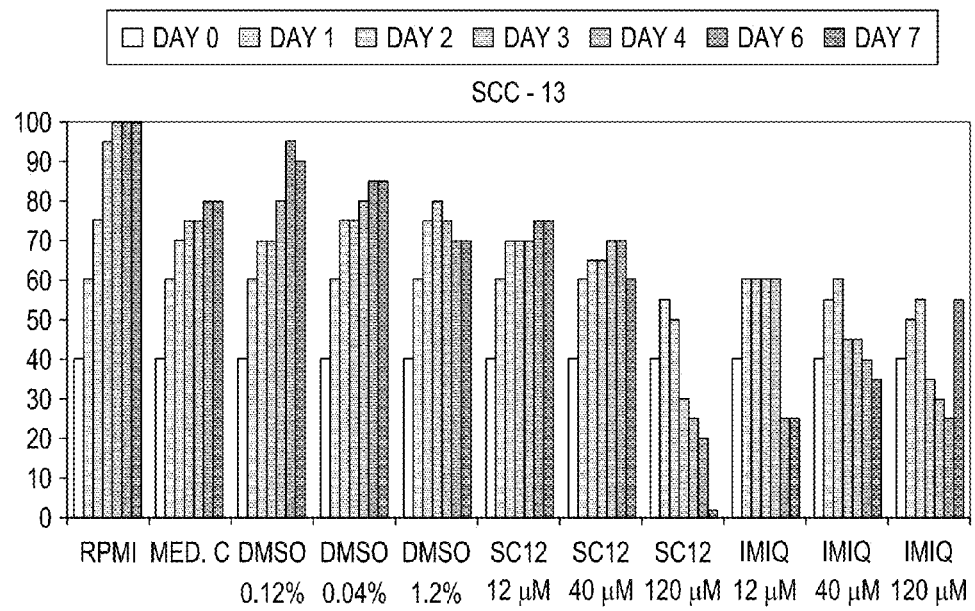
Figure 17D:
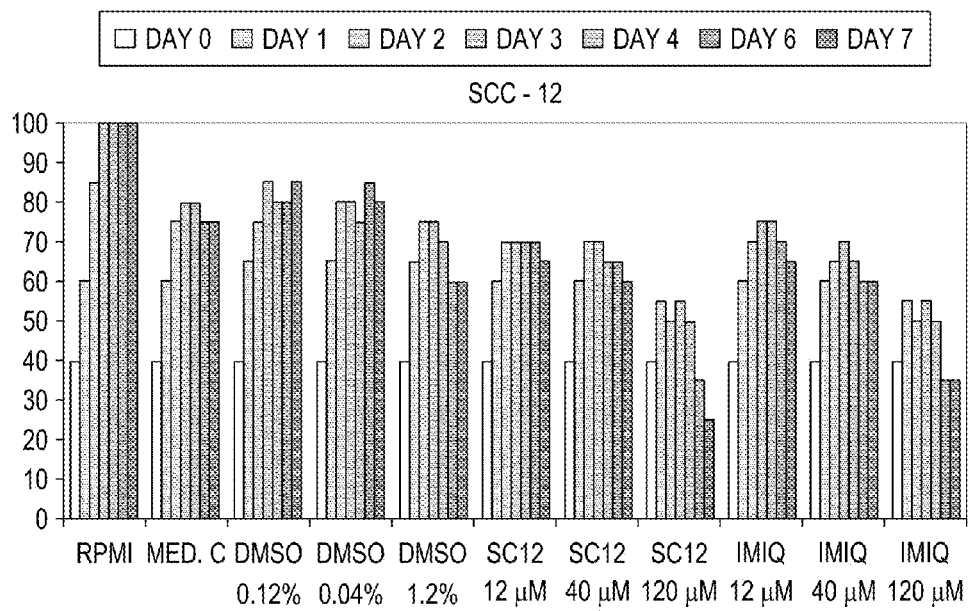

The CCR7 expression pattern in pDCs was similar to what we found in the mDCs. Compound A induced largely higher CCR7 expression than SC12 in all three donors. Imiquimod in FIG. 16 shows MFI values for CD80, CD86 and CCR7 expression in HLA-DR+/CD11c−/CD123+pDCs after 24 hours incubation with test reagents as indicated, performed on whole blood from three donors (D1-D3).

Conclusion of FACS Analysis:

The overall conclusions on the B cell studies was that compound A at the highest concentration (10 uM) stimulates slightly higher levels of the maturation marker CD40 than SC12 in all three donors.

For DC activation, SC12 was largely more potent than compound A regarding stimulation of the activation marker CD80, which was the case for both mDCs and pDCs (although a few exceptions were seen).

For the activation marker CD86 the results were a bit different as compound A was slightly more potent than SC12 in mDCs, whereas SC12 was slightly more potent than compound A in pDCs. However, the most potent concentration for expression of CD86 varies between the donors.

Expression of the chemokine receptor CCR7, showed that compound A was more potent than SC12 in both DC subsets in most donors. As for the CD86 expression, the most potent compound concentration for CCR7 induction varied between the donors.

Imiquimod generally showed to be potent only in donor 3 in B cells, mDCs as well as in pDCs, for the expression of all investigated markers.

Results

Compound A and SC12 were potent in induction of the cytokines IL-6, IL-10, IL-12p40 and IFN-alpha, and increased expression of maturation markers on both B-cells, pDCs and mDCs. The differences between the biological effect of compound A and SC12 measured on these parameters were not significant. However, if a larger number of donors were used, a statistically significant effect might be possible to show. Several effects showed borderline significance, and some maturation markers showed a tendency to be induced more potently by one of the compounds.

The tendencies showed:

Compound A showed a tendency to be more potent than SC12 for the following end-points.
1. Induction of the maturation marker CD86 on mDCs
2. Induction of the migration receptor CCR7 for both mDCs and pDCs 3. Induction of the B-cell activation marker CD40 SC12 showed tendency to be more potent than compound A for the following end-points.
1. Induction of the maturation marker CD80 on both mDCs and pDCs
2. Induction of the migration marker CD86 on pDCs
3. Induction of the cytokines IL-6 and IFN-alpha No tendencies could be seen at the level of IL-10 or IL-12p40 induction.

Based on these results, it can not be concluded that compound A and SC12 behave significantly different when incubated with fresh human blood.

SC12 was slightly more potent than compound A in pDC activation, since CD80 and CD86 were induced more potently on pDCs by SC12, and the pDC cytokine IFN-alpha was induced more potently by SC12. In addition, compound A might be slightly more potent in B-cell activation, in particular seen when tested at the 10 uM concentration.

Example 7

Preclinical Placebo-Controlled Efficacy Study with Imiquimod and SC12 in an Orthotopic Rat Bladder The goal of this study was to evaluate the efficacy of a liquid formulation of Imiquimod (R-487 (1)) and SC12 in an orthotopic bladder cancer model in F344 rats. Four groups were compared: Imiquimod, SC12, vehicle and a placebo-group. After treatment, the animal well-being was monitored, and the response on rat-bladder and tumor was evaluated histopathologically.

Animals, Material & Methods
Tumor Cells

The AY-27 rat bladder cancer cell-line was established from a primary bladder tumor in FANFT (N-[4-(5-nitro-2-furyl)-2-thiazolyl]formamide) fed Fischer F344 rats. The cell-line was kindly provided by the University of Alberta and Cross Cancer Institute, Edmonton, Alberta, Canada. The cells were cultured as a monolayer in RPMI-1640 (medium with L-glutamine (Invitrogen, Carlsbad, Calif.)), supplemented with 10% fetal calf serum (Sigma-Aldrich, St. Louis, Mo.), 100 U/mL penicillin G and 100 µg/mL streptomycin (Invitrogen, Carlsbad, Calif.) in a humidified 95% air/5% carbon dioxide atmosphere. The medium was replaced two times a week, and when confluent, the cells were passaged with standard trypsinization procedures. Passage numbers used for the experiments were 28 and 29.

Animals

A total of 56 female Fischer F344 rats were purchased from Charles River (L'Arbresle Cedex, France) and were acclimatized for at least one week before the start of the experiment. The rats, weighing 170 g±10 g, were housed in individual cages (Techniplast, Milan, Italy) with gold flakes bedding (SPPS, Frasne, France) and environmental enrichment, in a temperature controlled environment with a 12-hour light/dark cycle with free access to standard chow and water. Each day, the rats were weighed and monitored for wellbeing. Animal procedures were performed according to protocols, which need to be approved by the Institutional Animal Care and Use Committee (IACUC), Committee for Animal Experiments (Radboud University Nijmegen Medical Centre, The Netherlands) and in compliance with Dutch and European regulations.

Sample Size Calculation

The group size was calculated using an expected therapy effect of 50%, an α of 0.05, a power of 80% and 80% tumor development. This resulted in a minimal group size of 14.

Tumor Cell Implantation

The tumor cell implantation was performed on day 0 according to the protocol of Xiao et al (2). The F344 rats received isogenic tumor cells, resulting in a bladder tumor establishment of more than 80% (3). Enrofloxacin (Bayer, Leverkusen, Germany) (5-10 mg/kg) was injected subcutaneously for antibacterial prophylaxis before each catheterization. Experiments were performed under inhalation anesthesia: Isoflurane 2-5% (induction),followed by Isoflurane 2%, nitric oxide 0.5 L/min and oxygen 1 L/min. The rat bladder was catheterized via the urethra with a 16-gauge (1.4 mm) plastic intravenous cannula (BD Biosystems, Erembodegem-Aalst, Belgium) and drained. The bladder was pre-conditioned with a 15 s instillation of 0.4 mL 0.1 M hydrochloride (HCl) and neutralized by adding 0.4 mL 0.1 M potassium hydroxide (KOH) for 15 s. The bladder was drained and flushed 3 times with 0.8 mL 0.01 M PBS. Freshly harvested AY-27 cells (passage 28 and 29) were resuspended in medium. Immediately after bladder conditioning, and within 1 hour after cell harvesting, the cells ($1.5*10^6$ in 0.5 ml medium) were instilled in the rat-bladder and left indwelling for 1 hour. The rats were rotated 90° every 15 minutes. After 1 hour, the catheter was removed, and the rats could void spontaneously.

TABLE 24

| Treatment groups | | |
| --- | --- | --- |
| Group | Intravesical instillation | N |
| 1 | Imiquimod 0.1% | 14 |
| 2 | SC12 0.38% | 14 |
| 3 | Vehicle | 14 |
| 4 | NaCl | 14 |

Treatment

All the rats received an intravesical instillation on day 2 and 5. First the rats were anesthetized by inhalation for one hour, as described before. Subsequently the rats were catheterized via the urethra using a 1.4 mm cannula (BD Biosystems), the bladder was drained and the pH was measured using pH indicator strips (Merck, Darmstadt Germany). The intravesical instillation was administrated using a 1 mL Luer-Lok syringe (BD Biosystems). Group 1 (n=14) was treated with 0.5 ml IMIQUIMOD 0.1%. Group 2 was treated with 0.5 ml SC12 0.38%. Group 3 received an instillation with the vehicle (Phosal 50) and Group 4 received an instillation with NaCl as a control. The testing agents were dissolved in Phosal 50 (Lipoid AG) as vehicle. The instillation remained in the bladder for 1 hour, and the rats were rotated 90° each 15 min. After one hour, the catheter was removed. The pH of spontaneously voided urine was measured using pH-indicator strips (Merck).

Pathological Evaluation

On day 12, the rats were sacrificed using carbon dioxide inhalation. At necropsy the internal organs were inspected and cystectomy was performed. The bladders were weighed, fixated using 4% buffered. laminated and embedded in paraffin. Sections of 5 µm were stained using hematoxylin and eosin (H&E). A uro-pathologist evaluated the bladder sections, and scored the T stage using the TNM classification (Union International Contre le Cancer, UICC, 2002). In addition, the total number of tumors per bladder and the invasion depth of the tumors was measured. The amount of inflammation in the bladder wall and/or surrounding tissue was scored 0 (no inflammation), 1 (mild), 2 (moderate) and 3 (severe inflammation).

Results

During the experiment, there were no signs of impaired wellbeing of the rats and no rat reached a humane endpoint. An expected slight decrease of weight was seen only the first day after anesthesia, but on the days following instillation, all rats regained weight. Mild hematuria on the day of catheterization was reported occasionally. On subsequent days, the urine turned normal. The pH of the urine before and after treatment showed no difference; the pH of all urines varied between 6.5 and 7.0. At necropsy no abnormalities to internal organs other than the bladder were seen. At macroscopic evaluation tumor-positive bladders appear to have tumor mass without extravesical growth. Only one rat bladder (group 3, vehicle treated) showed a mass near the right urethral orifice, extending towards the right ureter.

Bladder Weight

The bladder weight correlated with the presence of tumor (p<0.0001, independent samples T test). In the table, an overview of the means and range is given. There was a difference of mean bladder weight between group 2 (SC12) and group 3 (Vehicle), (p=0.005, independent samples T test). No difference in mean bladder weight was seen between other groups.

TABLE 25

Weight of the rat bladders per treatment and control group. Weight in grams.

| Group | N | Mean weight | Standard deviation | Range |
|---|---|---|---|---|
| 1 | 14 | 0.1201 | 0.03488 | 0.0814-0.1891 |
| 2 | 12 | 0.1014 | 0.02258 | 0.0780-0.1422 |
| 3 | 12 | 0.1442 | 0.04163 | 0.0874-0.2028 |
| 4 | 13 | 0.1082 | 0.02311 | 0.0837-0.1587 |
| Total | 51 | 0.1184 | 0.03458 | 0.0780-0.2028 |

Inflammation

In almost all the rats a certain degree of inflammation was present. Between groups no statistically significant difference was observed (p=0.106, Pearsons Chi-square test). The mild and moderate degree of inflammation accounted for 87.5% of all 56 cases.

Tumors and Tumor Response

The number of rats with a tumor positive bladder was 9 of 14 for the IMIQUIMOD treated group (group 1), 8 of 14 for the SC12 treated group (group 2), 11 of 14 for the vehicle-control group (group 3) and also 11 of 14 for the NaCl control group (group 4). All tumors show a pT2 stage, except one pTa tumor in the vehicle-group. The pT2 tumors extend into the detrusor muscle. In the rat with the pTa tumor, a small portion of cancer cells were seen on top of the normal urothelial lining, with no invasion. There was no statistically significant difference between the individual groups in terms of tumor development. The difference in tumor development between group 2 and the group 4 shows a non-significant p-value of 0.210 (Fischers Exact Test). The treatment given (e.g. IMIQUIMOD, SC12, vehicle or NaCl) was not predictive of the outcome (tumor positive versus tumornegative), when a logistic regression analysis was performed on the data.

| Group | Tumor free | pTa Tumor | pT2 Tumor | Total |
|---|---|---|---|---|
| 1 | 5 (35.7%) | | 9 (64.3%) | 14 (100%) |
| 2 | 6 (42.9%) | 1 (7.1%) | 7 (50.0%) | 14 (100%) |
| 3 | 3 (21.4%) | | 11 (78.6%) | 14 (100%) |
| 4 | 3 (21.4%) | | 11 (78.6%) | 14 (100%) |

Invasion Depth

Invasion depth of tumors was measured by a uro-pathologist on histopathological evaluation of the H&E stained bladder sections. The deepest point at which tumor cells were seen, was taken as the invasion depth. The mean invasion depth of tumor positive bladders did not show significant differences between individual treatment groups (independent sample T test, p=0.486-0.912), or between SC12-treated (groups 1,2) and control treated (groups 3,4) animals (independent sample T-test p=0.705)

TABLE 27

Mean tumor invasion depth

| Group | Mean invasion depth (mm) | Standard deviation | N |
|---|---|---|---|
| 1 | 1.3333 | 0.45552 | 8 |
| 2 | 1.4250 | 0.70660 | 8 |
| 3 | 1.5000 | 0.56921 | 11 |
| 4 | 1.3909 | 0.55759 | 11 |

Tumor Number

The absolute number of tumors per bladder was counted by the uro-pathologist. The number of tumors in the vehicle control group was higher than the other groups. In univariate analysis, the number of tumors in the vehicle group (group 3) differed significantly from group 1 and 4 (p=0.02) and from group 2 (p=0.006).

TABLE 28

Mean number of tumors per rat bladder

| Group | Mean number of tumors | Standard deviation |
|---|---|---|
| 1 | 1.71 | 1.773 |
| 2 | 1.36 | 2.098 |
| 3 | 3.57 | 2.563 |
| 4 | 1.71 | 1.637 |

Conclusions

Imiquimod and SC12 cause a local immune response, that may lead to antitumor activity. No signs of toxicity were seen during this experiment. Although the effect of treatment on the tumor rate was not statistically significant, a positive trend is seen towards the Imiquimod and SC12-treated animals. Based on these data, future experiments may have an increased treatment frequency to improve efficacy.

References For Example 7

(1) Hayashi T, Crain B, Corr M, Chan M, Cottam H B, Maj R, et al. Intravesical Toll-like receptor δ agonist IMIQUIMOD: Optimization of its formulation in an orthotopic mouse model of bladder cancer 1. International Journal of Urology 2010 May; 17(5):483-90.
(2) Xiao Z, McCallum TJ, Brown KM, Miller GG, Halls SB, Parney I, et al. Characterization of a novel transplantable orthotopic rat bladder transitional cell tumor model 3. British Journal of Cancer 1999 October; 81(4):638-46.
(3) Hendricksen K, Molkenboer-Kuenen J, Oosterwijk E, De Kaa CAHV, Witjes JA. Evaluation of an orthotopic rat bladder urothelial cell carcinoma model by cystoscopy. Bju International 2008 April; 101(7):889-93.

Example 8

Toxicity Analysis of SC12—Bacterial Mutation Assay

SC12 was examined for the ability to induce gene mutations in tester strains of *Salmonella typhimurium* and *Escheri-* chia coli, as measured by reversion of auxotrophic strains to prototrophy. The five tester strains TA1535, TA1537, TA98, TA100 and WP2 uvrA were used. Experiments were performed both in the absence and presence of metabolic activation, using liver S9 fraction from rats pre-treated with phenobarbitone and betanaphthoflavone. SC12 was used as a solution in dimethylsulfoxide (DMSO). SC12 was assayed in the toxicity test at a maximum concentration of 5000 micrograms/plate and at four lower concentrations spaced at approximately half-log intervals: 1580, 500, 158 and 50.0 micrograms/plate. Precipitation of SC12 was observed at the end of the incubation period at the two highest concentrations. No toxicity was observed with any tester strain at any dose level in the absence or presence of S9 metabolism.

Using the plate incorporation method, SC12 was assayed at the maximum dose level of 5000 micrograms/plate and at four lower dose levels spaced by two-fold dilutions: 2500, 1250, 625, and 313 micrograms/plate. No toxicity was observed with any tester strain at any dose level, in the absence or presence of S9 metabolism. Precipitation of SC12 was observed at the end of the incubation period at the two highest concentrations.

As no increases in revertant numbers were observed at any concentration tested, a pre-incubation step was included for all treatments of Main Assay II. SC12 was assayed at the same dose-range employed in Main Assay I. No toxicity was observed with any tester strain at any dose level, in the absence or presence of S9 metabolism.

Dose-related precipitation of SC12, which did not interfere with the scoring, was observed at the end of the incubation period at the four highest concentrations.

SC12 did not induce two-fold increases in the number of revertant colonies in the plate incorporation or pre-incubation assay, at any dose level, with any tester strain, in the absence or presence of S9 metabolism.

It was concluded that SC12 does not induce reverse mutation in *Salmonella typhimurium* or *Escherichia coli* in the absence or presence of S9 metabolism, under the reported experimental conditions.

Example 9

Toxicity Analysis of SC12—Single Dose Intravenous Study in Rats

The acute toxicity of SC12 was investigated after a single intravenous administration to the Sprague Dawley rat followed by a 14-day observation period. A preliminary phase was carried out by subsequently dosing groups of one male and one female rat at 76, 100, 85 and 90 mg/kg, who were observed for a period of 7 days. An additional group, similarly composed, received the vehicle alone and acted as a control. No mortality occurred at 76 mg/kg. Clinical signs were limited to piloerection and reduced activity, observed on the day of dosing.

A second group was dosed at 100 mg/kg. Both animals died at dosing, after convulsions. A third group was then dosed at 85 mg/kg. Piloerection was observed on the day of dosing. A fourth group was finally dosed at 90 mg/kg. No mortality occurred. Piloerection was observed from Day 2 up to Day 4 of the study. No death occurred and no clinical signs were noted in male and female animals treated with the vehicle alone.

In the main phase, 5 male and 5 female animals were dosed at 90 mg/kg and observed for a period of 14 days. A second group, similarly constituted, received the vehicle alone and acted as control. Three males treated at 90 mg/kg died immediately after dosing, while two females died at 2 hours post-dose. In addition, one male and one female dosed at 90 mg/kg were found dead on Day 2 of the study. Twitches, ataxia, piloerection, reduced activity and hunched posture were the major signs observed in animals before death. Ataxia, piloerection, reduced activity, hunched posture and semi-closed eyes were noted in the surviving animals on the day of dosing. Piloerection was observed up to Day 3 of the study. A second group, similarly composed, was dosed at 80 mg/kg. No mortality occurred and no clinical signs were recorded during the observation period. No mortality occurred and no clinical signs were observed in animals receiving the vehicle alone.

Surviving animals treated at 90 mg/kg and animals dosed at 80 mg/kg showed a slight to moderate body weight loss on Day 2 of the study. Recovery occurred by Day 15 and the body weight changes were within the expected range for this species and age of animals at the end of the study. No relevant changes in body weight were observed in animals receiving the vehicle alone during the study. Surviving animals were killed at the end of the observation period with carbon dioxide narcosis. All animals, including the early decedents, were subjected to necropsy examination. No abnormalities were observed at necropsy examination performed on all animals treated at 90 mg/kg (including the early decedents), 80 mg/kg and on control animals. These results indicate that the test item SC12 induced mortality or significant signs of toxicity in rats following intravenous administration of a single dose at 90 mg/kg, while no mortality and no signs of toxicity were observed at 80 mg/kg. Therefore, the maximum tolerated dose in this study was considered to be 80 mg/kg.

Example 10

Binding Assays

Figure 18:
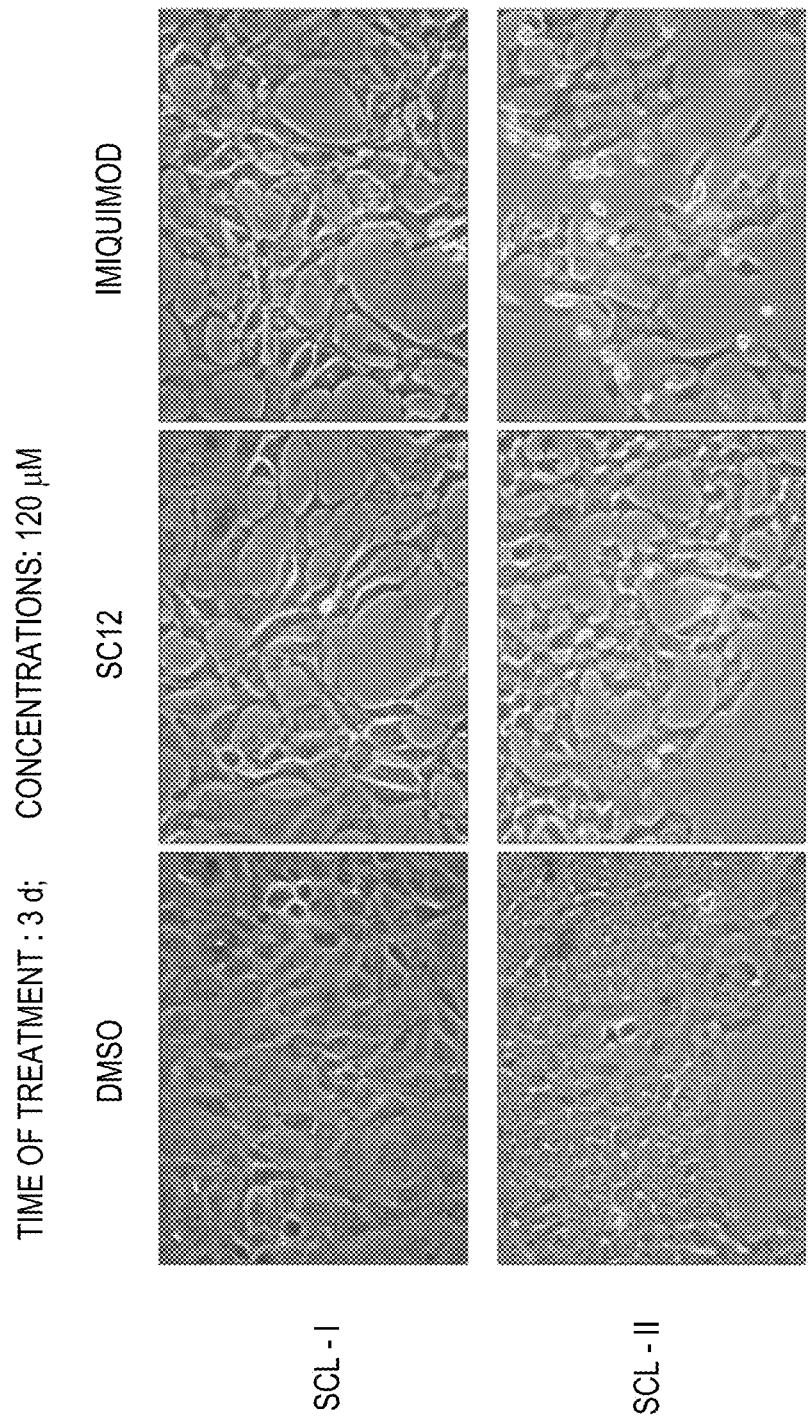
FIG. 18 is a collection of photographs of cells contacted with SC12 or Imiquimod Similar morphological changes were induced by SC12 and Imiquimod. At day 3, cell detachment, morphological changes and inhibition of proliferation can be observed in SCC cells treated with either SC12 or Imiquimod.

Imiquimod and SC12 were analyzed in enzymatic and radiologic binding assays, as shown in FIGS. 17, and 18, respectively. SC12 and imiquimod were evaluated in a radio-ligand binding assay among 73 primary molecular targets using different human recombinant receptor types and sub-types or membrane fraction from rodent tissue homogenates. SC12 was tested at a fixed concentration of 30 microM.

Imiquimod was shown to bind to receptors that are associated with pain-related syndromes (e.g. adenosine and sodium channel), which are the most common adverse events in patients after treatment with Aldara (imiquimod). SC12 did not bind this type of receptors.

Example 11

Investigation of the Intravenous Pharmacokinetics of SC12 in the Mouse

The pharmacokinetics of SC12 was assayed in fasting male CD-1 mice.

Materials and Methods

An IV bolus was administered into the caudal vein at a dose of 1 mg/kg in 5 ml. The compound weight was 2.08/10.04 ml. 24 mice were studied. Sampling was obtained by exsanguination under anesthesia, at 5, 15, 30, 60, 240, and 480 minutes, and at 24 hours. SC12 was administered in a formulation of 3% DMSO, 20% beta-cyclo-dextrin, in water, at a dose volume of 5 ml/kg. Animals were sacrificed using ethyl ether at the conclusion of the experiment.

Sample preparation: In a Sirocco filter plate, 100 microliters of plasma were added to 300 microliters of ACN/MeOH spiked with 5 microliters of IS (IV298 10 micrograms per ml)

plus 10 microliters of 5% $H_3PO_4$. The plate was shaken for 10 minutes at 80 rpm and then filtered under vacuum for 5 minutes.

Analytical method: LC/MS/MS: Premiere XE, Eluent: water (A) MeOH (B) plus 0.1% HCOOH gradient. 15% B to 100% B from 0.1 to 0.5, then isocratic 100% B up to 1.5 minutes, flow 0.8 ml/min; Column Acquity UPLC BEH C18 1.7 microm 2.1×50 mm, injection volume of 5 microliters in a T column at 50° C. ESI positive, MRM, Extractor 5V; Capillary 3.5 kV; T source 115° C.; T desolv. 450° C. SC12: MH+921.5>385.05/439.29 CV35 CE33 LLOQ: 5 ng/ml.

Data analysis: Non-compartmental analysis WinNonlin 5.1; linear trapezoidal, uniform weight.

Results

No adverse behavioral effects were noted in the treatments.

SC12 shows a Cmax in plasma of 541 ng/ml with a short MRT, which is reflected in a high clearance (Table 29). Some inter-animal variability was observed at the first time point (5 min), possibly due to the very rapid clearance in the first part of the decay, whereas, in the second part of the curve, the concentration in plasma decreased slowly, being under the LLOQ (lowest limit of quantification) after 2 hrs.

Raw data and non-compartmental analysis output are reported in Table 30.

TABLE 29

| Pharmacokinetic parameters | |
|---|---|
| T½ (min.) | 130 |
| Tmax (min.) | 5 |
| Cmax (ng/ml) | 541 |
| C0 (ng/ml) | 2664 |
| Tlast (min) | 120 |
| Clast (ng/ml) | 6 |
| AUClast (min * ng/ml) | 11744 |
| AUC INF obs (min * ng/ml) | 12878 |
| CI (ml/min/kg) | 77.7 |
| MRT (min) | 32 |
| Vss (L/kg) | 2.5 |

TABLE 30

| Raw data and non-compartmental analysis output | |
|---|---|
| Time (min) | Plasma concentration Mean ± S.D. (ng/ml) |
| 5 | 540.70 ± 179.99 |
| 15 | 22.27 ± 3.16 |
| 30 | 10.00 ± 1.68 |
| 60 | 7.62 ± 0.72 |
| 120 | 6.05 ± 0.78 |
| 240 | <LLOQ |
| 480 | <LLOQ |
| 1440 | <LLOQ |

Example 12

Inhibition of Human CYP450 In Vitro

The interaction of SC12 with cytochrome P450 enzymes was tested using Fluorescent High Throughput P450 assays (Gentest); The IC50s of the compounds was calculated on isoenzymes (CYP1A2, CYP2C9, CYP2C19, CYP2C8, CYP2B6, CYP2D6, CYP2E1, CYP3A4 and CYP3A5).

Materials and Methods

Inhibition of the P450 isoforms was measured in specific assays using specific substrates that become fluorescent upon CYP metabolism. Compounds, dissolved in ACN (acetonitrile) (CYP2E1, CYP2C8, CYP2B6, CYP3A5) or DMSO (all remaining isoforms), were tested in duplicate (n=2) in concentration-response curves (eight concentrations) in a 96-well plate containing incubation/NADPH regenerating buffer. Specific isoenzymes and substrates were added and incubated at 37° C. Reactions were terminated at different times, depending on the assays, and plates read on a Fluoroskan Ascent at the appropriate emission/excitation wavelengths. Concentration-response curves performed in duplicate for known inhibitors for each isoenzyme were tested in every assay as positive control.

Data Analysis

For each compound and standard the IC50 (concentration at 50% inhibition) was determined by using Grafit v. 5.0.1.

Results

Results are Shown in Table 31 (Compounds) and Table 32 (Standards).

SC12 showed a moderate inhibition on CYP2E1, CYP3A5 and CYP3A4 isoforms and a weak inhibition on CYP2C9, whereas it did not appear to inhibit the others isoforms activity. Because SC12 showed a low solubility, especially in ACN, results could be underestimated. The standard reference inhibitors in all the experiments performed showed the expected potency.

TABLE 31

| COMPOUND | P450 results | | | | | | | | |
|---|---|---|---|---|---|---|---|---|---|
| | CYP1A2 CEC | CYP2C9 MFC | CYP2C19 CEC | CYP2D6 AMMC | CYP3A4 BFC | CYP3A5 BFC | CYP2E1 MFC | CYP2CB DBF | CYP2B6 EFC |
| | $IC_{50}$ micromolar (Mean ± S.D.) | | | | | | | | |
| SC12 | >100 | 33.4 ± 0.3 | >100 | 67.0 ± 3.8 | 13.6 ± 0.7 | 10.5 ± 0.5 | 9.2 ± 0.1 | >100 | >100 |

Abbreviations:
BFC: 7-Benzyloxy-4-(trifluoromethyl)-coumarin
CEC: 3-Cyano-7-Ethoxycoumarin
AMMC: 3-[2(N,N-diethyl-N-methylamino)ethyl]-7-methoxy-4-methylcoumarin
DBF: Dibenzylfluorescein
DMSO: Dimethylsulfoxide
EFC: 7-Ethoxy-4-trifluoromethylcoumarin
MFC: 7-Methoxy-4-trifluoromethylcoumarin

TABLE 32

P450 results on standard inhibitors

| Isoforms | Standard inhibitors | Experiment data IC50 (microM) |
|---|---|---|
| CYP1A2 | Furafylline | 1.9 ± 0.1 |
| CYP2C9 | Sulfaphenazole | 0.27 ± 0.01 |
| CYP2C19 | Tranylcypromine | 5.0 ± 0.2 |
| CYP2D6 | Quinidine | 0.009 ± 0.001 |
| CYP3A4 | Ketoconazole | 0.012 ± 0.001 |
| CYP3A5 | Ketoconazole | 0.12 ± 0.10 |
| CYP2E1 | DDTC | 0.85 ± 0.01 |
| CYP2C8 | Quercetin | 3.5 ± 0.4 |
| CYP2B6 | Tranylcypromine | 6.9 ± 1.2 |

Example 13

Investigation of Metabolic Stability and Profiling of Compound a in Mammalian Plasma, and Comparison of Compound a and SC12 Stability in Human Plasma The stability of compound A was tested in rat, rabbit, minipig and human plasma up to 5 hours, and metabolic profiling was assessed in rabbit and human plasma. Compound A was highly metabolized by esterases/amidases in rabbit and human, and in a lesser extent in minipig and rat species. Metabolism was studied in rabbit at 30 and 120 min and in human at 60 and 300 min, i.e. operating at approximately the same residual percentages of the parent in the two species. Three metabolites were found in rabbit and two of them in human.

In rabbit the major metabolites were the monoester (loss of one oleic acid, M2) and the acid metabolite (amide hydrolysis, M3), whereas only traces of the di-hydrolyzed metabolite (loss of both oleic acids, M1) were observed. In human plasma only the first two major metabolites, previously detected in rabbit, were identified at the selected time points and the acid product (M3) was the predominant metabolite at 120 min.

In conclusion, in human and rabbit species a comparable profile of clearance and metabolism profile was found, with the formation of only two major metabolites where the rate limiting step is the hydrolysis leading to monoester formation (M2), which rapidly converted into the acid derivative (M3).

In a second experiment performed in human plasma with a second batch of compound A in comparison with SC12 suggested that SC12 is little more stable than compound A, because it was not metabolized up to 120 min, and more than 70% of the compound was still present at 300 min (compound A unchanged at 300 min: 55%).

Example 14

Direct Proapoptotic Effects of SC12 on Skin Cancer Cell Lines: a Comparison with Imiquimod In addition to its immunomodulatory effects, Imiquimod has been reported to directly induce apoptosis in tumor cells, which has been confirmed in tumors of different origin in vivo. The proapoptotic activity of Imiquimod may contribute to the antitumoral effects of Imiquimod in vivo, as the required concentrations are still approximately 3 logs below the concentration in Aldara 5% cream.

Experimental Methods and Results
Cell Lines:

Cutaneous Squamous Cell Carcinoma (SCC) cell lines (human) SCL-I, SCL-II, SCC-12, SCC-13 have been well characterized with regard to their growth behavior and apoptosis sensitivity to death ligands (CD95L, TRAIL, TNF-alpha) as well as to other treatments. SCC cells are grown under standard conditions (10% FBS).

Determination of the Direct Proapoptotic and Cytotoxic Effects of SC12 on SCC Cells:

Time and dose dependency of effects on total cell numbers have been investigated by real-time cell analysis, which is based on continuous monitoring of electric conductance in microtiter wells (E-plates, Roche), which corresponds to the cell numbers. Different concentrations of SC12 as well as Imiquimod (Imq) have been used to treat the 4 cell lines and the cell numbers have been compared to untreated control cells (2 independent experiments for each cell line, triple values, different concentrations). For these assays 4 cell lines should be used to obtain a representative overview on the effects on SCC cells. Thus, cells have been treated with different concentrations of SC12 or Imiquimod; growth and apoptotic effects have been monitored by microscopy for at least 7 days.

FIG. 17 shows reduced cell numbers with SC12 and Imiquimod. Cutaneous SCC cell lines were continuously monitoring of electric conductance in microtiter wells (E-plates, Roche), which corresponds to the cell numbers. TMX indicates SC12 in the charts. FIG. 18. provides photographs showing similar morphological changes induced by SC12 and Imiquimod. At day 3, cell detachment, morphological changes and inhibition of proliferation can be observed in SCC cells treated with either SC12 or Imiquimod. Time of treatment 3d, Concentrations: 120 microM.

Example 15

Compound A and SC12 as Adjuvants

A pilot immunization study was conducted using compound A and SC12 adjuvanted protein antigens. The immunization experiments were performed with two recombinant proteins expressed in *E. coli*. One antigen was derived from the malaria parasite *Plasmodium falciparum* and the other one from *Mycobacterium ulcerans*, which cause the ulcerative skin disease Buruli ulcer.

Groups of five mice received, with three week intervals, three subcutaneous immunizations with 20 micrograms of target antigen mixed with 10 nMol compound A or SC12.

After the third immunization, all 20 immunized mice had developed IgG responses against the respective target antigens. The performance of compound A and SC12 was comparable. No local side effects, such as swelling or ulcerations were observed. A parallel immunization with a commercial adjuvant approved for use in mice yielded higher antibody titers; but here local reactions were observed.

Figure 19A:
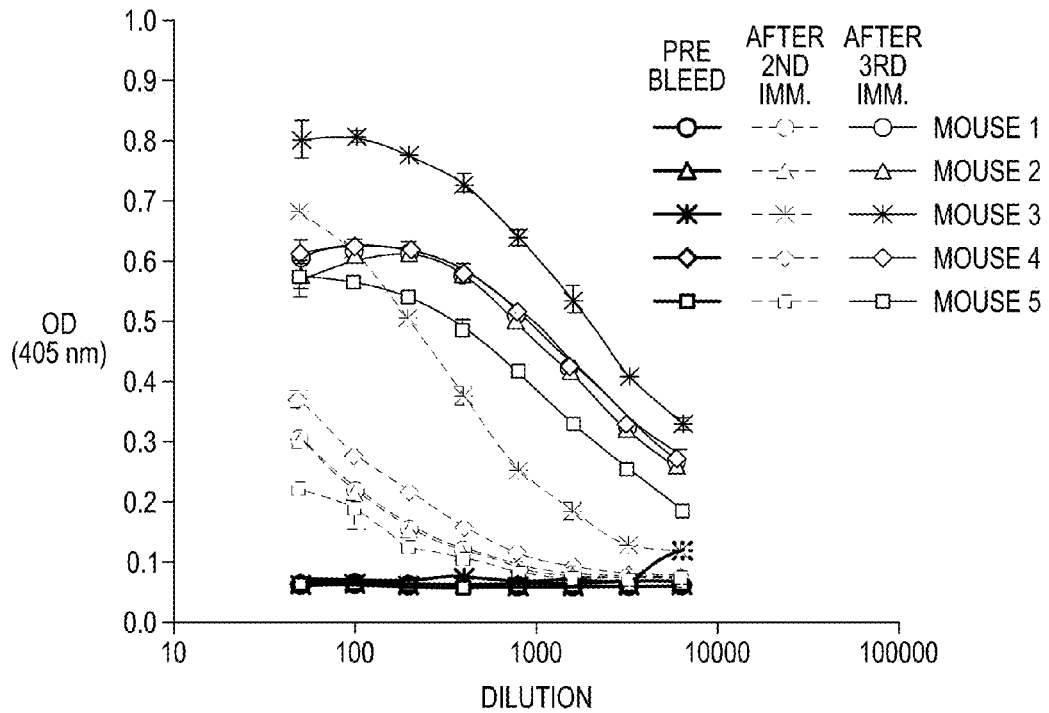
FIGS. 19A and 19B show the development of IgG titers against the *M. ulcerans* antigen, (upper: compound A, lower, SC12).
Figure 19B:
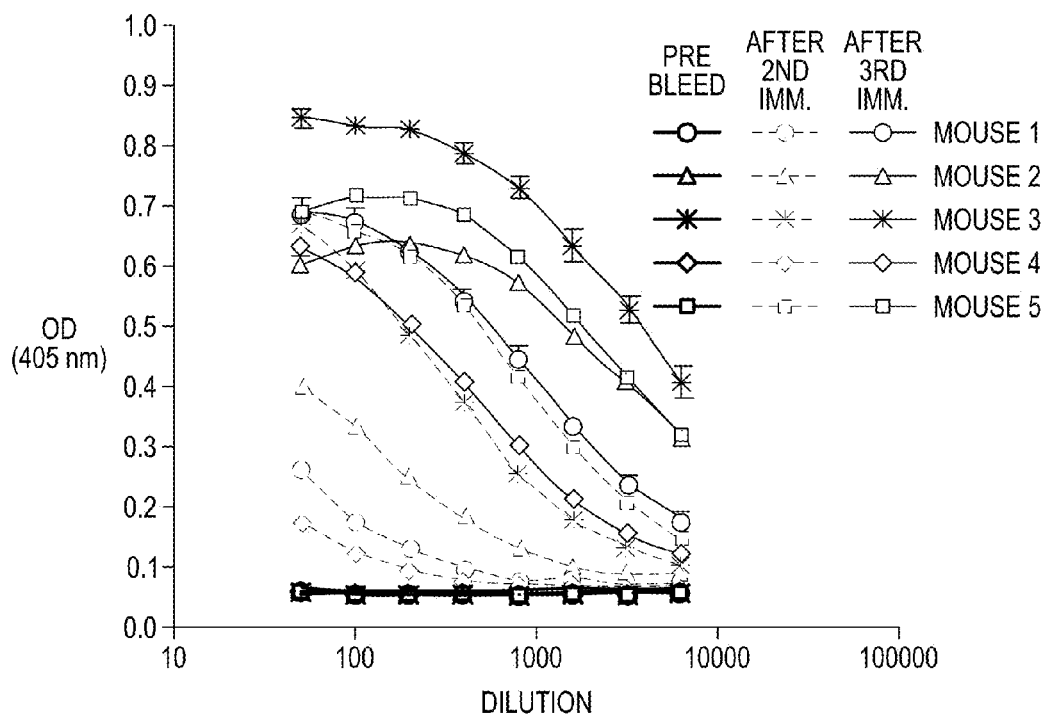

FIG. 19 shows the development of IgG titers against the *M. ulcerans* antigen, (left: compound A, right, SC12).

Example 16

Investigation of the Exposure of Imiquimod and SC12 in Mouse Serum after Intravesical Chronic Treatment Materials and Methods Female 6-8 week old C57BL/6 mice were treated intravesically with either Imiquimod (0.1 w/v % in total 208 nmol) or SC12 (0.38 w/v % in total 206.5 nmol). Serum samples were taken at time points: day 0, 2 hours, day 1, 24 hours, and day 6, 2 hours.

Sample Preparation

Imiquimod: In a Sirocco Filter Plate (Waters), 50 microliters of mouse serum to 195 microliters of acetonitrile/methanol 1:1 spiked with 5 microliters of IS (Imiquimod-D9 100 micrograms/ml).The plate was shaken for 10 minutes and filtered under vacuum (5-10 mm Hg).

SC12: In a Sirocco Filter Plate (Waters), 70 microliters of mouse serum were added to 210 microliters of acetonitrile/methanol 1:1 spiked with 5 microliters of IS (Imiquimod-D9 100 ng/ml).The plate was shaken for 10 minutes and filtered under vacuum (5-10 mm Hg). Samples were evaporated and re-suspended in 70 microliters of acetonitrile/methanol 1:1.

Analytical Method

Imiquimod: LC/MS/MS: Premiere XE, Eluent: (ACN/H2O 95/5 (A)+0.1% HCOOH, 5/95 (B)) flow 0.60 ml/min from 98% A 0-0.20 mins, gradient to 100% B in 0.6 min, then stay to 100% B until 1.1 mins, reconditioning for 0.4 min.

Column: Acquity BEH C18 50×2.1 mm 1.7 micrometers; injection volume 5 microliters, T column 50° C.

SC12: LC/MS/MS: Premiere XE, Eluent: (MeOH/H2O 95/5 (A)+0.1% HCOOH, 5/95 (B)) flow 0.80 ml/min from 85% A 0-0.10 mins, gradient to 100% B in 0.4 min, then stay to 100% B until 1.5 mins, reconditioning for 0.7 min.

Column: Acquity BEH C8 50×2.1 mm 1.7 micrometers injection. volume 10 microliters, T column 50° C.

| | | |
|---|---|---|
| SC12 | Q1/Q3 | 921.5/385.05; CV35, CE33 |
| | | 921.5/439.29; CV35, CE33 |
| Imiquimod | Q1/Q3 | 241.1/113.98; CV30, CE45 |
| | | 241.1/140.9; CV30, CE40 |
| IS: Imiquimod-D9 | Q1/Q3 | 250.1/113.98; CV30, CE45 |

ESI positive, MRM, Extractor 5 V;
Capillary 3.5 kV;
T source 140° C.;
T desolvation 450° C.
LLOQ: 0.5 ng/ml SC12 and 2.5 ng/ml for Imiquimod Results The aim of this study was to evaluate the exposure of serum after intravesical chronic administration of Imiquimod and SC12. Serum levels of SC12 and Imiquimod are reported in Table 33 and Table 34, respectively. Low concentrations were observed for both compounds, in particular for SC12, where the major part of the samples were below the LLOQ, even if the LLOQ obtained for SC12 was five times lower than the LLOQ obtained for Imiquimod (0.5 vs 2.5 ng/ml). Imiquimod was present in the serum up to 2 hours after administration, but no accumulation is occurring resulting below the LLOQ at 24 hours and with values after 6 days of treatment comparable to day 1.

TABLE 33

SC12 levels in serum
Results are expressed as Mean ± S.D., n = 2

| | Mice n° | Day 0, 2 hours | Day 1, 24 hours ng/ml | Day 6, 2 hours |
|---|---|---|---|---|
| SC12, | 9 | 1.0 | <LLOQ | <LLOQ |
| 0.1% | 10 | <LLOQ | <LLOQ | <LLOQ |
| | 11 | 0.5 | <LLOQ | <LLOQ |
| | 12 | <LLOQ | <LLOQ | <LLOQ |
| Vehicle | 13 | <LLOQ | <LLOQ | <LLOQ |
| Mean ± S.D. | | 0.5 ± 0.5 | <LLOQ | <LLOQ |

TABLE 34

Imiquimod levels in serum
Results are expressed as Mean ± S.D., n = 2

| | Mice n° | Day 0, 2 hours | Day 1, 24 hours ng/ml | Day 6, 2 hours |
|---|---|---|---|---|
| Imiquimod | 1 | 6.4 | <LLOQ | 8.7 |
| 0.1% | 2 | 6.8 | <LLOQ | |
| | 3 | 5.3 | <LLOQ | |
| | 1 | | | 2.8 |
| | 2 | | | 8.1 |
| | 3 | | | 16.3 |
| Vehicle | 14 | <LLOQ | <LLOQ | <LLOQ |
| Mean ± S.D. | | 6.2 ± 0.8 | <LLOQ | 8.9 ± 5.6 |

List of abbreviations
Acetonitrile ACN
Collision Energy CE
Cone Voltage CV
Dimethylsulfoxide DMSO
Electron Spray Ionization ESI
Internal Standard IS
Liquid Chromatography/Mass Spectrometry LC-MS/MS
Lowest limit of quantification LLOQ
Methanol MeOH
Multiple Reaction Monitoring MRM
Ultra Performance Liquid Chromatography UPLC Example 17

Intracellular Uptake in RAW.264 Cells

In cellular assays, SC12 rapidly reaches high intracellular concentration. $5 \times 10^6$ RAW.264 cells were adhered overnight in 10 cm tissue culture dishes. The medium was replaced with 10 ml of a new media containing 10 microM compound A and SC12. The cells were incubated for 1, 6, and 18 hours. Supernatant (2 ml) and cells (pellets) were collected by trypsinization and frozen at 20° C. for subsequent analysis by LC-MS. Table 35 shows the results of this analysis.

TABLE 35

Results of intracellular uptake assay

| Compound | Incubation hours | Intracellular Concentration % of total |
|---|---|---|
| Compound A | 1 | 5.50 |
| | 6 | 4.27 |
| | 16 | 1.53 |
| SC12 | 1 | 18.5 |
| | 6 | 20.6 |
| | 18 | 21.4 |

Example 18

Synthesis of SC14

The compound designated as tetradecanoic acid 3-[(2-{4-[6-amino-2-(2-methoxy-ethoxy)-8-oxo-7,8-di hydro-purin-9-ylmethyl]-benzoylamino}-ethoxy)-hydroxy-phosphoryloxy]-2-tetradecanoyloxy-propyl ester (SC14) was synthesized as described below.

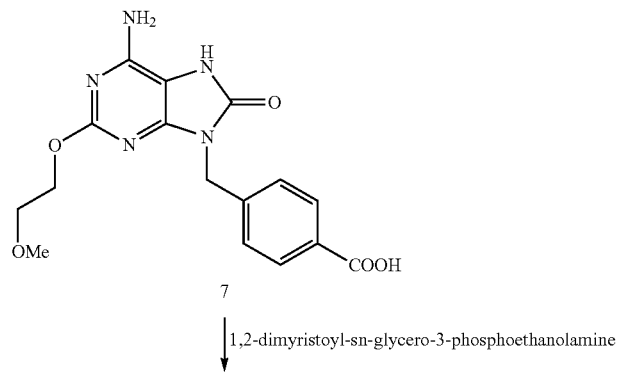

7

↓ 1,2-dimyristoyl-sn-glycero-3-phosphoethanolamine

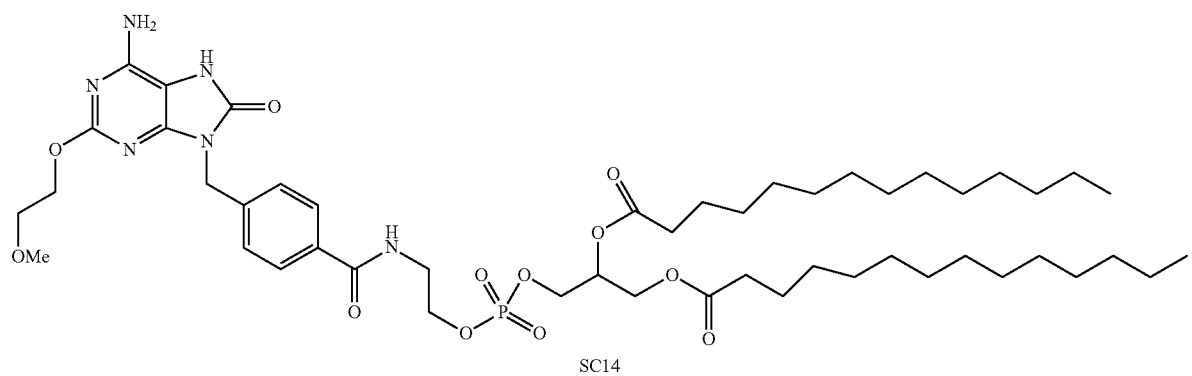

SC14

For preparing SC14, Acid 7 (compound 7) (Chimete, batch CH907/5/7b; 0.3 g, 0.83 mmol) was dissolved in a mixture of dichloromethane and dimethylformamide (DMF) (9/1, 27 mL) at room temperature under an Argon atmosphere. Triethylamine (0.3 mL; 4 mmol) was added, followed by HATU (390 mg; 1.03 mmol). The resulting solution was stirred at room temperature for 10 min, followed by the addition of 1,2-dimyristoyl-sn-glycero-3-phosphoethanolamine (DMPE; Avanti Polar Lipids, Cas Number 998-07-2, 600 mg; 0.94 mmol). The solution was then stirred overnight. The mixture was then diluted with water (100 mL). A solid formed and was isolated by filtering with a Buchner funnel followed by washing with methanol (10 mL). SC14 was obtained as a pale yellow solid designated batch CH957/3/2 with a yield of 600 mg (73%) and a purity 95% as determined by HPLC. The structure was confirmed by $^1$H-NMR and MS.

Example 19

Synthesis of SC6

The SC6 designated as hexanoic acid 3-[(2-{4-[6-amino-2-(2-methoxy-ethoxy)-8-oxo-7,8-dihydro-purin-9-ylm-ethyl]-benzoylamino}-ethoxy)-hydroxy-phosphoryloxy]-2-hexanoyloxy-propyl ester (SC6) was synthesized as described below.

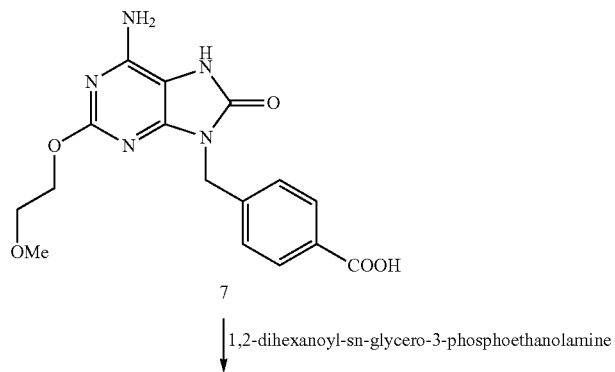

7

↓ 1,2-dihexanoyl-sn-glycero-3-phosphoethanolamine

-continued

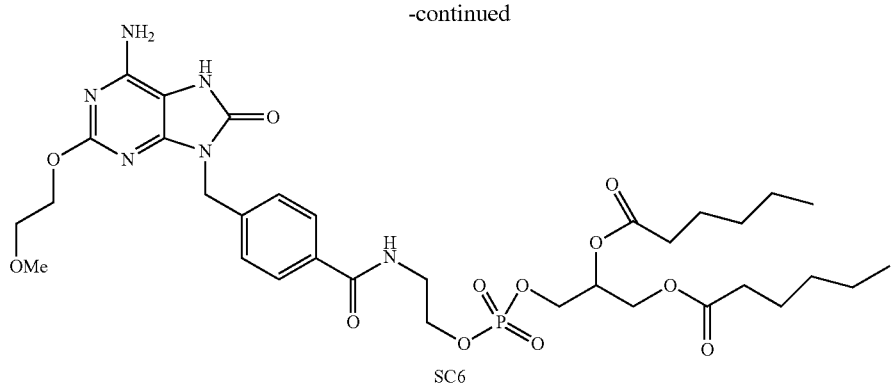
SC6

For preparing SC6, Acid 7 (compound 7) (Chimete, batch CH907/5/7b; 0.5 g, 1.39 mmol) was dissolved in a mixture of acetonitrile (10 mL) and DMSO (4 mL) at room temperature and under Argon atmosphere. Carbonyl diimidazole (Aldrich, batch 0001408017; 270 mg, 1.67 mmol, 1.05 eqv.) was added and the resulting solution was stirred for 1 hr. A solution of 1,2-dihexanoyl-sn-glycero-3-phosphoethanolamine (Avanti Polar Lipids; 600 mg; 1.46 mmol.) was added in one portion. The reaction mixture was stirred for 16 hours, until complete conversion of the reagents. Acetonitrile was removed by distillation in vacuum. Water (50 mL) was added to the residue and a white solid separated. The solid was recovered by centrifugation. The solid was purified by column chromatography and was eluted with ethyl acetate/methanol/formic acid 8/1/1. After drying in a vacuum at 35° C., SC6 was obtained as a white solid desinated batch CH957/2/1B with a yield of 500 mg (47%) and a purity of 96.4% as determined by HPLC. The structure was confirmed by 1H-NMR and MS.

Example 20

Effect of SC14 on PBMC

To determine the effects of SC14 treatment on TNF-alpha and IL-6 release from human PBMC (Peripheral Blood Mononuclear Cells), human PBMC were isolated from buffy coats of human donors (Rho Hospital, Milan, Italy). Briefly, buffy coats from three healthy donors were diluted 1:1 in sterile PBS (phosphate buffered saline). PBMCs were isolated by density gradient centrifugation using Lymphocyte-H solution (Cederlane Laboratories). After two washing steps in PBS pH 7.4, cells were resuspended in RPMI-1640, 10% FCS, L-glutamine ($2\times10^4$ M), penicillin (100 µml) and streptomycin (100 ug/ml). Three milliliters of a $1.6\times10^6$ ml suspension of PBMCs were seeded in six-well tissue culture plates. Wells were treated with either IMIQUIMOD, SC12, SC6 or SC14 at concentrations of 50 uM, 10 uM, 2 uM, 0.4 uM, 0.08 uM and 0.016 uM. LPS (3 ul of a 1 mg/ml solution) was added to an untreated well as a positive control at a final concentration of 1 ug/ml. PBMCs were then incubated for 24 hours. Supernatants were collected by centrifugation at 1200 rpm for 10 minutes and frozen at −20° C. for later cytokine analysis.

Figure 24A:
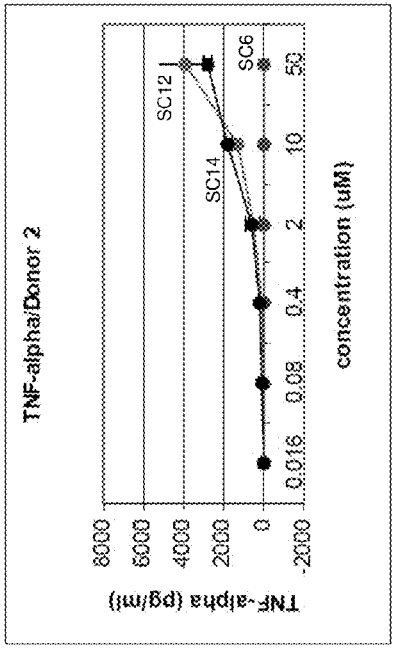
FIGS. 24A, 24B and 24C show SC14 and SC12 inducing TNF-alpha release from human PBMC.
Figure 24B:
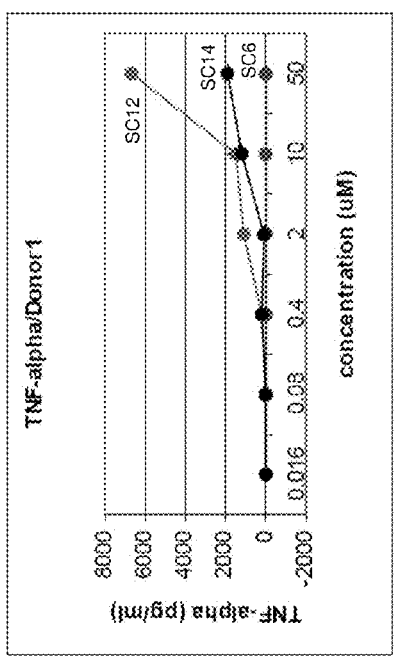
Figure 24C:
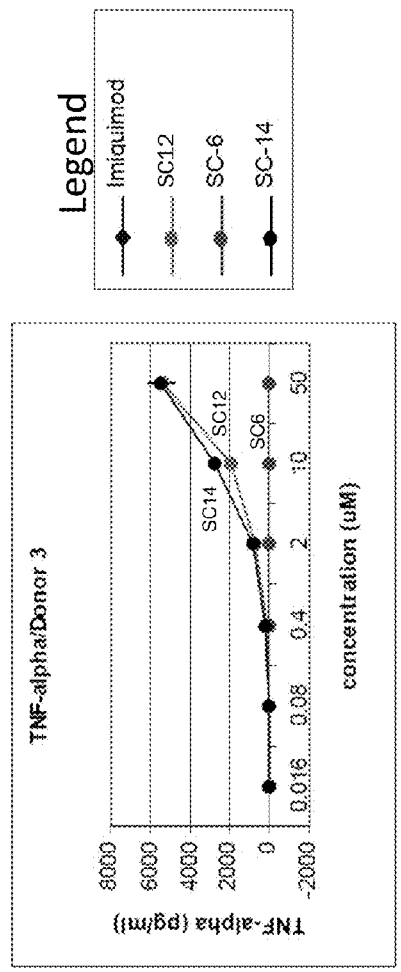
Figure 25A:
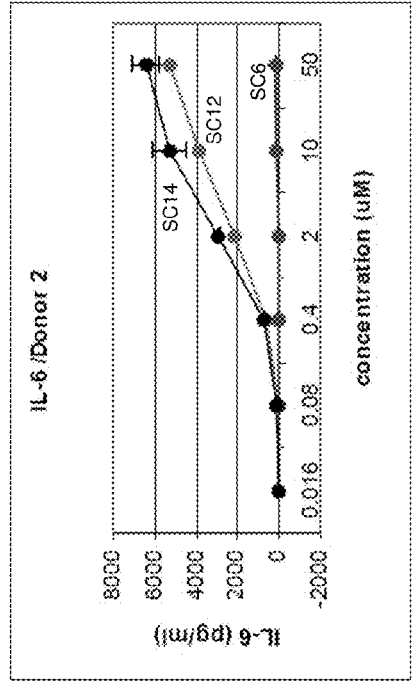
FIGS. 25A, 25B and 25C show SC14 and SC12 inducing IL-6 release from human PBMC.
Figure 25B:
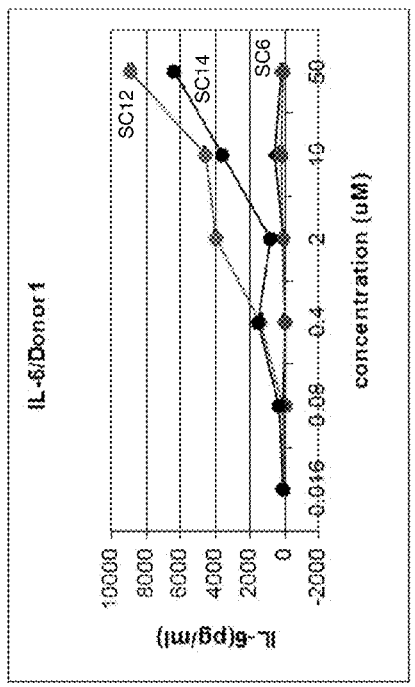
Figure 25C:
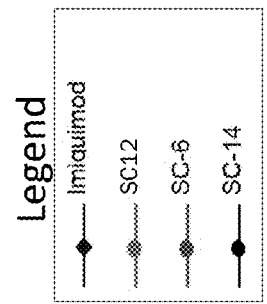
Figure 25C:
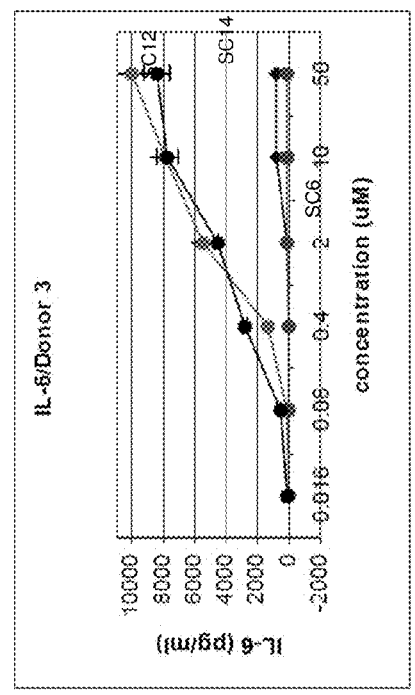

Cytokine concentrations were determined using a commercial Luminex kit (Fluorokine Map Multiplex Kit) for the simultaneous quantitative determination of multiple human cytokine concentrations. Mean TNF-alpha and IL-6 production levels after LPS stimulation are reported in Table 36 as a positive control. TNF-alpha and IL-6 were detected at high levels in the supernatant of PBMCs after treatment for 24 hours with SC12 or SC14, whereas IMIQUIMOD and SC6 did not show a significant stimulatory effect (Table 37 and FIG. 24 (TNF); Table 38 and FIG. 25 (IL-6)).

All cytokine concentrations are presented as the Mean+/−SD (standard deviation, n=2). In Table 37 and Table 38, an * indicates that one or both values were extrapolated beyond the range of the standard. In Table 38, OOR<indicates the data was out of range (i.e., below the range of the standard). Cytokine release was calculated per milliliter of plasma and concentration units are pg/ml of medium.

TABLE 36

| | LPS Positive Control | | | |
|---|---|---|---|---|
| | TNF-α | | IL-6 | |
| | pg/ml | SD | pg/ml | SD |
| Donor 1 | 1167.5 | 42.2 | *11837.9 | 329.2 |
| Donor 2 | 802.7 | 47.4 | *7613.8 | 516.4 |
| Donor 3 | 738.7 | 25.8 | *11387.4 | 577.5 |

TABLE 37

TNF-alpha Release from Human PBMC

| | TNF-α | | | | | | | | | | | |
|---|---|---|---|---|---|---|---|---|---|---|---|---|
| | 0.016 µM | | 0.08 µM | | 0.4 µM | | 2 µM | | 10 µM | | 50 µM | |
| | pg/ml | SD | pg/ml | SD | pg/ml | SD | pg/ml | SD | pg/ml | SD | pg/ml | SD |
| Donor 1 | | | | | | | | | | | | |
| IMIQUIMOD | *3.48 | 0.20 | *1.925 | 0.15 | *0.93 | 0.01 | 15.29 | 0.21 | 31.98 | 2.11 | 11.75 | 0.36 |
| SC12 | *1.34 | 1.89 | *4.89 | 0.47 | 173.46 | 25.69 | 1074.18 | 2.55 | 1471.62 | 442.53 | *6680.36 | 124.32 |

TABLE 37-continued

TNF-alpha Release from Human PBMC

| | TNF-α | | | | | | | | | | | |
|---|---|---|---|---|---|---|---|---|---|---|---|---|
| | 0.016 μM | | 0.08 μM | | 0.4 μM | | 2 μM | | 10 μM | | 50 μM | |
| | pg/ml | SD | pg/ml | SD | pg/ml | SD | pg/ml | SD | pg/ml | SD | pg/ml | SD |
| SC-6 | *1.60 | 0.01 | 1.38 | 0.01 | *1.92 | 0.01 | *4.60 | 0.01 | 6.68 | 0.59 | *5.64 | 0.30 |
| SC-14 | *2.25 | 0.01 | 41.37 | 0.01 | 189.47 | 13.17 | 102.45 | 10.18 | 1244.23 | 7.00 | 1935.68 | 5.35 |
| Donor 2 | | | | | | | | | | | | |
| IMIQUIMOD | *1.71 | 0.16 | *1.81 | 0.30 | *1.49 | 0.47 | 6.88 | 0.53 | 22.36 | 0.63 | 11.91 | 0.71 |
| SC12 | *2.62 | 0.08 | 8.44 | 1.89 | 123.11 | 0.46 | 515.10 | 5.78 | 1250.81 | 102.97 | 3925.96 | 1264.79 |
| SC-6 | *1.54 | 0.08 | *1.10 | 0.08 | *1.28 | 0.45 | 6.31 | 0.45 | 13.38 | 0.60 | 8.84 | 0.31 |
| SC-14 | *4.90 | 0.22 | 59.86 | 2.66 | 197.06 | 28.09 | 559.85 | 339.62 | 1622.42 | 179.86 | 2785.56 | 209.03 |
| Donor 3 | | | | | | | | | | | | |
| IMIQUIMOD | *3.295 | 0.11 | *2.43 | 0.23 | *2.43 | 0.23 | 6.56 | 0.42 | 20.04 | 0.30 | 12.52 | 1.41 |
| SC12 | *4.14 | 0.01 | 8.70 | 0.30 | 83.39 | 3.05 | 736.05 | 28.74 | 1939.86 | 147.50 | *5377.97 | 653.40 |
| SC-6 | *2.59 | 0.45 | *1.95 | 0.01 | *3.83 | 1.30 | 8.91 | 0.01 | 7.15 | 0.42 | 9.36 | 0.21 |
| SC-14 | 5.81 | 0.21 | 21.64 | 0.39 | 201.17 | 16.27 | 783.56 | 22.06 | 2750.70 | 49.60 | *5503.35 | 546.44 |

TABLE 38

IL-6 Release from Human PBMC

| | IL-6 | | | | | | | | | | | |
|---|---|---|---|---|---|---|---|---|---|---|---|---|
| | 0.016 μM | | 0.08 μM | | 0.4 μM | | 2 μM | | 10 μM | | 50 μM | |
| | pg/ml | SD | pg/ml | SD | pg/ml | SD | pg/ml | SD | pg/ml | SD | pg/ml | SD |
| Donor 1 | | | | | | | | | | | | |
| IMIQUIMOD | 23.09 | 2.02 | *1.27 | 0.60 | OOR< | na | 102.57 | 1.56 | 502.60 | 1.17 | 236.16 | 1.12 |
| SC12 | *3.51 | 0.32 | 23.37 | 0.85 | 1377.51 | 65.35 | 3987.04 | 21.12 | 4596.94 | 106.06 | *8902.80 | 113.99 |
| SC-6 | *0.59 | 0.36 | OOR< | — | OOR< | — | 33.90 | 1.59 | 147.16 | 7.90 | 110.90 | 2.48 |
| SC-14 | *0.64 | 0.91 | 287.23 | 12.30 | 1475.62 | 101.17 | 788.67 | 47.82 | 3634.59 | 114.22 | *6308.86 | 24.37 |
| Donor 2 | | | | | | | | | | | | |
| IMIQUIMOD | *1.07 | 0.31 | *1.29 | 0.01 | *0.99 | 1.00 | 17.05 | 1.60 | 164.50 | 8.42 | 189.53 | 7.83 |
| SC12 | *4.52 | 0.93 | 34.53 | 2.47 | 673.18 | 26.18 | 2118.17 | 265.54 | 3637.74 | 65.08 | *5282.86 | 351.33 |
| SC-6 | *2.47 | 0.01 | *0.34 | 0.01 | 5.86 | 0.26 | 29.93 | 1.29 | 103.33 | 1.73 | 89.52 | 2.72 |
| SC-14 | 16.47 | 0.01 | 100.74 | 3.69 | 742.72 | 12.20 | 2910.82 | 43.96 | 5261.94 | 832.16 | *6404.48 | 668.12 |
| Donor 3 | | | | | | | | | | | | |
| IMIQUIMOD | 18.62 | 0.66 | 6.84 | 0.84 | 6.62 | 1.67 | 149.38 | 13.16 | 749.26 | 67.39 | 785.68 | 26.79 |
| SC12 | 33.53 | 0.25 | 152.81 | 13.79 | 1377.26 | 71.76 | *5461.65 | 769.39 | *7928.53 | 862.58 | *10081.99 | 795.83 |
| SC-6 | 9.99 | 0.27 | 8.13 | 0.42 | 19.54 | 2.76 | 137.54 | 2.60 | 145.17 | 8.68 | 173.86 | 18.22 |
| SC-14 | 91.80 | 0.49 | 497.46 | 14.06 | 2829.73 | 124.13 | *4542.78 | 33.15 | *7825.40 | 649.58 | *8462.40 | 763.51 |

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A composition comprising a compound having a structure:

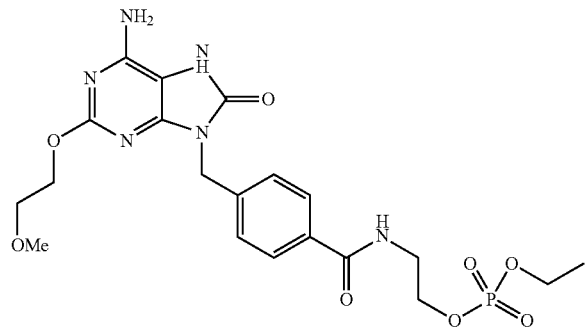

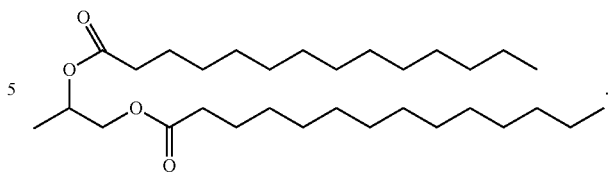

2. The composition of claim 1, which further comprises an antigen.

3. The composition of claim 1, which comprises a vaccine.

4. A method for inducing an immune response in a subject, comprising administering to the subject a composition of claim 1.

* * * * *

UNITED STATES PATENT AND TRADEMARK OFFICE
CERTIFICATE OF CORRECTION

| | | |
|---|---|---|
| PATENT NO. | : 9,050,319 B2 | |
| APPLICATION NO. | : 13/775924 | |
| DATED | : June 9, 2015 | |
| INVENTOR(S) | : Roberto Maj et al. | |

It is certified that error appears in the above-identified patent and that said Letters Patent is hereby corrected as shown below:

Column 95, line 9 – Column 96, line 8, should read

1. A composition comprising a compound having a structure:

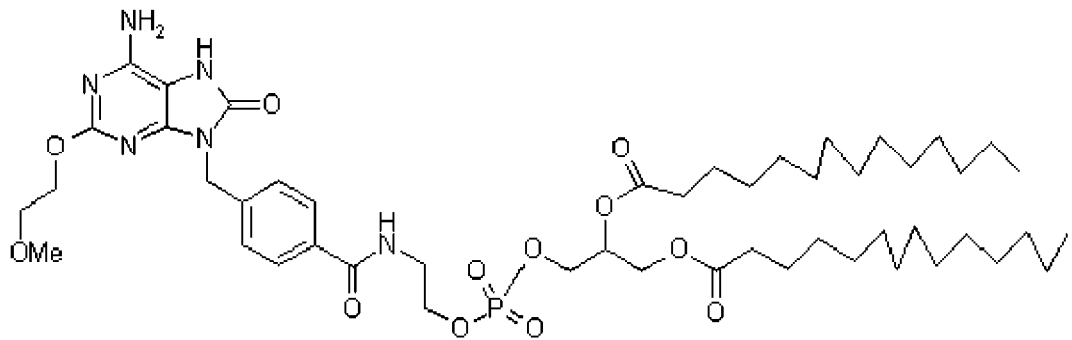

Signed and Sealed this
Twenty-sixth Day of January, 2016

Michelle K. Lee
*Director of the United States Patent and Trademark Office*